US011692019B2

(12) United States Patent
Kim et al.

(10) Patent No.: US 11,692,019 B2
(45) Date of Patent: Jul. 4, 2023

(54) HETERODIMERIC FC-FUSED CYTOKINE AND PHARMACEUTICAL COMPOSITION COMPRISING THE SAME

(71) Applicant: Ajou University Industry-Academic Cooperation Foundation, Suwon (KR)

(72) Inventors: Yong Sung Kim, Suwon (KR); Keunok Jung, Suwon (KR); Ji Hee Ha, Daegu (KR); Dong Ki Choi, Daejeon (KR); Hye Ji Choi, Suwon (KR); Ye Jin Kim, Usan (KR)

(73) Assignee: Ajou University Industry-Academic Cooperation Foundation, Suwon-si (KR)

(*) Notice: Subject to any disclaimer, the term of this patent is extended or adjusted under 35 U.S.C. 154(b) by 44 days.

(21) Appl. No.: 16/886,184

(22) Filed: May 28, 2020

(65) Prior Publication Data

US 2020/0362005 A1 Nov. 19, 2020

Related U.S. Application Data

(62) Division of application No. 16/323,839, filed as application No. PCT/KR2017/008676 on Aug. 10, 2017, now Pat. No. 10,696,722.

(30) Foreign Application Priority Data

Aug. 10, 2016 (KR) .................. 10-2016-0101823
Aug. 10, 2017 (KR) .................. 10-2017-0101594

(51) Int. Cl.
| | |
|---|---|
| *C12N 15/62* | (2006.01) |
| *C12N 5/00* | (2006.01) |
| *C07K 14/54* | (2006.01) |
| *A61K 38/20* | (2006.01) |
| *C07K 14/59* | (2006.01) |
| *A61K 38/00* | (2006.01) |

(52) U.S. Cl.
CPC ........ *C07K 14/5434* (2013.01); *A61K 38/208* (2013.01); *C07K 14/54* (2013.01); *C07K 14/59* (2013.01); *A61K 38/00* (2013.01); *C07K 2319/30* (2013.01)

(58) Field of Classification Search
CPC .................................. C12N 15/62; C12N 5/00
See application file for complete search history.

(56) References Cited

U.S. PATENT DOCUMENTS

| | | | |
|---|---|---|---|
| 4,722,848 A | 2/1988 | Paoletti et al. | |
| 5,173,414 A | 12/1992 | Lebkowski et al. | |
| 5,624,821 A | 4/1997 | Winter et al. | |
| 5,648,260 A | 7/1997 | Winter et al. | |
| 5,807,706 A | 9/1998 | Carter et al. | |
| 6,194,551 B1 | 2/2001 | Idusogie et al. | |
| 6,737,056 B1 | 5/2004 | Presta | |
| 6,838,260 B2 | 1/2005 | Gillies et al. | |
| 6,864,235 B1 | 3/2005 | Turley et al. | |
| 7,226,998 B2 | 6/2007 | Gillies et al. | |
| 7,576,193 B2 | 8/2009 | Gillies et al. | |
| 7,695,936 B2 | 4/2010 | Carter et al. | |
| 7,879,319 B2 | 2/2011 | Gillies et al. | |
| 7,943,743 B2 | 5/2011 | Korman et al. | |
| 7,951,917 B1 | 5/2011 | Arathoon et al. | |
| 8,034,630 B2 | 10/2011 | Terashima et al. | |

(Continued)

FOREIGN PATENT DOCUMENTS

| | | |
|---|---|---|
| EP | 2691417 | 8/2018 |
| JP | 2001-525423 A | 12/2021 |

(Continued)

OTHER PUBLICATIONS

Brekke et al., (1994) "Human IgG isotype-specific amino acid residues affecting complement-mediated cell lysis and phagocytosis," Eur. J. Immunol. 24: 2542-47.
GenBank Accession No. NP_002178.2.
GenBank Accession No. NP_000873.2.
Idusogie et al., 2000, "Mappig of the C1q Binding Site on Rituxan, a Chimeric antibody with a human IgG1 Fc," Journal of Immunology, 164:4178-84.

(Continued)

*Primary Examiner* — Prema M Mertz
(74) *Attorney, Agent, or Firm* — Goodwin Procter LLP

(57) ABSTRACT

The present invention relates to a heterodimeric Fc-fused protein comprising a first Fc region and a second Fc region of an immunoglobulin Fc pair and a physiologically active protein composed of two or more different subunits, wherein one or more subunits of the physiologically active protein are linked separately to one or more ends of the N-terminus or C-terminus of the first Fc region and/or the second Fc region, and CH3 domains of the first Fc region and the second Fc region are mutated so as to promote the heterodimeric Fc formation. Moreover, the present invention relates to a pharmaceutical composition comprising the heterodimeric Fc-fused protein. The heterodimeric Fc-fused protein according to the present invention has an advantage in that it can retain the activity of a naturally occurring physiologically active protein whose two or more different subunits exhibit physiological activity by forming a protein complex, because the physiologically active protein can be linked to an immunoglobulin heterodimeric Fc such that the naturally occurring form and structure of the fused protein thereof can be maintained. When the heterodimeric Fc-fused protein according to the present invention is used, there is an advantage in that the in vivo half-life of the physiologically active protein contained in the heterodimeric Fc-fused protein can be significantly increased due to the Fc-mediated long half-life such that various physiological activities thereof in vivo can be long-lasting.

20 Claims, 24 Drawing Sheets

Specification includes a Sequence Listing.

(56) References Cited

U.S. PATENT DOCUMENTS

| | | | |
|---|---|---|---|
| 8,044,022 B2 | 10/2011 | Kolodka et al. | |
| 8,163,498 B2 | 4/2012 | Fujita | |
| 8,192,744 B2 | 6/2012 | Stromblad et al. | |
| 8,592,562 B2 | 11/2013 | Kannan et al. | |
| 8,674,083 B2 | 3/2014 | Presta | |
| 8,679,785 B2 | 3/2014 | Carter et al. | |
| 8,765,412 B2 | 7/2014 | Arathoon et al. | |
| 8,802,093 B2 | 8/2014 | Johnson et al. | |
| 8,871,912 B2 | 10/2014 | Davis et al. | |
| 8,945,571 B2 | 2/2015 | Mössner et al. | |
| 8,969,526 B2 | 3/2015 | Baehner et al. | |
| 9,217,016 B2 | 12/2015 | Panitch et al. | |
| 9,248,182 B2 | 2/2016 | De Kruif et al. | |
| 9,447,159 B2 | 9/2016 | Ast et al. | |
| 9,493,578 B2 | 11/2016 | Lazar et al. | |
| 9,505,848 B2 | 11/2016 | Davis et al. | |
| 9,562,109 B2 | 2/2017 | Von Kreudenstein et al. | |
| 9,637,557 B2 | 5/2017 | Scheer et al. | |
| 9,751,919 B2 | 9/2017 | Saward et al. | |
| 9,795,686 B2 | 10/2017 | Lee et al. | |
| 9,951,145 B2 | 4/2018 | Kim et al. | |
| 10,011,644 B2 | 7/2018 | Rueger et al. | |
| 10,047,167 B2 | 8/2018 | Demarest et al. | |
| 10,696,722 B2 | 6/2020 | Kim et al. | |
| 10,767,760 B2 | 9/2020 | Ando | |
| 11,078,249 B2 | 8/2021 | Kim et al. | |
| 2002/0055488 A1 | 5/2002 | Wessels et al. | |
| 2007/0259380 A1 | 11/2007 | Sumida et al. | |
| 2010/0015089 A1 | 1/2010 | Gillies et al. | |
| 2010/0256339 A1 | 10/2010 | Bossenmaier et al. | |
| 2010/0286374 A1 | 11/2010 | Kannan et al. | |
| 2011/0054151 A1 | 3/2011 | Lazar et al. | |
| 2012/0149876 A1 | 6/2012 | Von Kreudenstein et al. | |
| 2013/0039913 A1 | 2/2013 | Labrijn et al. | |
| 2014/0072579 A1 | 3/2014 | De Kruif et al. | |
| 2014/0079689 A1 | 3/2014 | Elliott et al. | |
| 2016/0046727 A1 | 2/2016 | Labrijn et al. | |
| 2016/0194389 A1 | 7/2016 | Regula et al. | |
| 2017/0056522 A1 | 3/2017 | Gerdes et al. | |
| 2017/0198038 A1 | 7/2017 | Gauthier et al. | |
| 2017/0260252 A1 | 9/2017 | Scheer et al. | |
| 2017/0342128 A1 | 11/2017 | Auer et al. | |
| 2017/0342167 A1 | 11/2017 | Moessner et al. | |
| 2017/0342168 A1 | 11/2017 | Schlothauer | |
| 2018/0237541 A1 | 8/2018 | Kim et al. | |
| 2018/0258386 A1 | 9/2018 | Rafii et al. | |
| 2018/0282386 A1 | 10/2018 | Vallera et al. | |
| 2018/0346600 A1 | 12/2018 | Kim et al. | |
| 2019/0185584 A1 | 6/2019 | Scheer et al. | |
| 2019/0218282 A1 | 7/2019 | Dengl et al. | |
| 2020/0362005 A1 | 11/2020 | Kim et al. | |

FOREIGN PATENT DOCUMENTS

| | | | |
|---|---|---|---|
| KR | 10-2015-0008012 A | 1/2015 | |
| WO | WO 1996/027011 A1 | 9/1996 | |
| WO | WO 1999/029732 A2 | 6/1999 | |
| WO | WO 2009/089004 A1 | 7/2009 | |
| WO | WO 2011/131746 A2 | 10/2011 | |
| WO | WO 2012/025530 A1 | 3/2012 | |
| WO | WO 2012/032080 A | 3/2012 | |
| WO | WO 2014/084607 A1 | 6/2014 | |
| WO | WO 2014/145907 A1 | 9/2014 | |
| WO | WO 2015/150447 A1 | 10/2015 | |
| WO | WO 2017/027422 A1 | 2/2017 | |
| WO | WO 2017/065484 A1 | 4/2017 | |
| WO | WO 2018/030806 A1 | 2/2018 | |
| WO | WO 2018/071919 A1 | 4/2018 | |
| WO | WO 2019/077092 A1 | 4/2019 | |
| WO | WO 2020/086758 | 4/2020 | |

OTHER PUBLICATIONS

Isaacs et al., 1998, "Therapy with Monoclonal Antibodies. II. The Contribution of Fcγ Receptor Binding and the Influence of CH1 and CH3 Domains on In Vivo Effector Function," Journal of Immunology, 161: 3862-69.

Tao et al., 1993, "Structural Features of Human Immunoglobulin G that Determine Isotype-specific Differences in Complement Activation," J. Exp. Med., 178:661-667.

Wang et al., (2018) "IgG Fc engineering to modulate antibody effector functions," Protein Cell 9(1): 63-73.

Atwell et al., 1997, "Stable heterodimers from remodeling the domain interface of a homodimer using a phage display library", J. Mol. Biol., 270(1):26-35.

Baek et al., 2014, "Construction of a large synthetic human Fab antibody library on yeast cell surface by optimized yeast mating", Journal of Microbiology and Biotechnology, 24(3):408-420.

Brar et al., 2014, "Genomic Evolution of Porcine Reproductive and Respiratory Syndrome Virus (PRRSV) Isolates Revealed by Deep Sequencing," PLOSone 9(4): e88807.

Chan et al., 2010, "Therapeutic antibodies for autoimmunity and inflammation," Nat Rev. Immunol 10(5):301-316.

Choi et al., 2015, "Crystal structures of immunoglobulin Fc heterodimers reveal the molecular basis for heterodimer formation," Mol Immunol 65(2):377-383.

Choi et al., 2015, "Engineering of immunoglobin Fc heterodimers using yeast surface-displayed combinatorial Fc library screening", PloS One, vol. 10, article No. 30145349:1-20.

Choi et al., 2013, "A Heterodimeric Fc-Based Bispecific Antibody Simultaneously Targeting VEGFR-2 and Met Exhibits Potent Antitumor Activity," Mol Cancer Ther, 12(12):2748-2759.

Cunningham et al., 1969, "Subgroups of Amino Acid Sequences in the Variable Regions of Immunoglobulin Heaw Chains," Proc. Natl. Acad. Sci. USA 64(3):997-1003.

Davis et al., 2010, "SEEDbodies: fusion proteins based on strand-exchange engineered domain (SEED) CH3 heterodimers in an Fc analogue platform for asymmetric binders or immunofusions and bispecific antibodies," Protein Engineering Design and Selection, 23(4):195-202.

Doctoral Thesis of Heyji-Choi at Ajou University, "Development of heterodimetic Fc variants for bispecific antibody platform technology," 2015.

Extended European Search Report, European Application No. 17839824.4, dated Feb. 18, 2020.

Feng et al., 2011, "Design, Expression and Characterization of a Soluble Single-Chain Functional Human Neonatal Fc Receptor," Protein Expression and Purification 79(1):66-71.

Gafner et al., 2006, "An engineered antibody-interleukin-12 fusion protein with enhanced tumor vascular targeting properties," International Journal of Cancer, John Wiley & Sons, Inc., 119(9):2205-2212.

Gillies et al., 1998. "Antibody-IL-12 fusioin proteins are effective in SCID mouse models of prostate and colon carcinoma metastases," Journal of Immunology, 160(12): 6195-6203.

Gunasekaran et al., 2010, "Enhancing antibody Fc heterodimer formation through electrostatic steering effects: applications to bispecific molecules and monovalent IgG (manuscript)," JBC Papers in Press, pp. 1-20.

Ha et al., 2016, "Immunoglobulin Fc Heterodimer Platform Technology: from Design to Applications in Therapeutic Antibodies and Proteins," Frontiers in Immunology, 7(394): 1-16.

Holliger et al., 2005, "Engineered antibody fragments and the rise of single domains," Nat. Biotechnol 23(9):1126-1136.

Hu et al., 2013, "Porcine Reproductive and Respiratory Syndrome Virus Vaccines: Current Status and Strategies to a Universal Vaccine," Transboundary and Emerging Diseases (2): 109-120.

International Search Report, PCT/KR2017/008676, dated Nov. 15, 2017.

Jung et al., 2018, "Heterodimeric Fc-fused IL12 shows potent antitumor activity by generating memory CD8 + T cells," Oncolmmunology, 7(7):e1438800.

Kim et al., 2007, "Comparative Analyses of Complex Formation and Binding Sites Between Human Tumor Necrosis Factor-Alpha and Its Three Antagonists Elucidate Their Different Neutralizing Mechanisms," J Mol Biol 374:1374-88.

(56) References Cited

OTHER PUBLICATIONS

Klein et al., 2012, "Progress in overcoming the chain association issue in bispecific heterodimeric IgG antibodies," MaBs 4(6):653-663.

Low et al., 2005, "Oral and pulmonary Delivery of FSH-Fc Fusion Proteins via Neonatal Fc Receptor-mediated Transcytosis," Human Reproduction, 20(7):1805-1813.

Lu et al., 2004, "Simultaneous Blockade of Both the Epidermal Growth Factor Receptor and the Insulin-Like Growth Factor Receptor Signaling Pathways in Cancer Cells with a Fully Human Recombinant Bispecific Antibody," J Biol Chem 279(4):2856-2865.

McBurney et al., 2009, "Human immunodeficiency virus-like particles with consensus envelopes elicited broader cell-mediated peripheral and mucosa I immune responses than polyvalent and monovalent Env vaccines," Vaccine 27(32):4337-4349.

Merchant et al., 1998, "An efficient route to human bispecific IgG", Nature Biotechnology 16: 677-681.

Miller et al., 2003, "Design, Construction, and in Vitro Analyses of Multivalent Antibodies," J. Immunol 170(9):4854-4861.

Milstein et al., 1983, "Hybrid Hybridomas and Their Use in immunohistochemistry," Nature 305: 537-540.

Moore et al., 2011, "A novel bispecific antibody format enables simultaneous bivalent and monovalent co-cngagemcnt of distinct target antigens," mAbs 3(6):546-557.

Muller et al., 2013, "High-resolution structures of the IgM Fc domains reveal principles of its hexamer formation," PNAS, 110(25):10183-10188.

Renukaradhya et al., 2015, "Live porcine reproductive and respiratory syndrome virus vaccines: Current status and future direction," Vaccine 33:4069-4080.

Ridgway et al., 2014, "Knobs-into-Holes' engineering of antibody Ch3 domains for heavy chain heterodimerization," Protein Engineering 9(7):617-621.

Schlothauer et al., 2016, "Novel human IgG1 and IgG4 Fc-engineered antibodies with completely abolished immune effector funtions," Protein Engineering, Design and Selection, 29(10): 10.

Strop et al., 2012, "Generating Bispecific Human IgG1 and 1gG2 Antibodies from Any Antibody Pair," J Mol Biol 420:204-219.

Von Kreudenstein et al., 2013, "Improving Biophysical Properties of a Bispecific Antibody Scaffold to Aid Developability: Quality by Molecular Design," mAbs 5:646-654.

Von Kreudenstein et al., 2014, "Protein Engineering and the Use of Molecular Modeling and Simulation: The Case of Heterodimeric Fe Engineering," Methods 65:77-94.

Vu et al., 2015, "A Synthetic Porcine Reproductive and Respiratory Syndrome Virus Strain Confers Unprecedented Levels of Heterologous Protection," J. Virology 89(23):12070-12083.

Xie et al., 2005, "A new format of bispecific antibody: highly efficient heterodimerization, expression and tumor cell lysis," Journal of Immunological Methods 296(1):95-101.

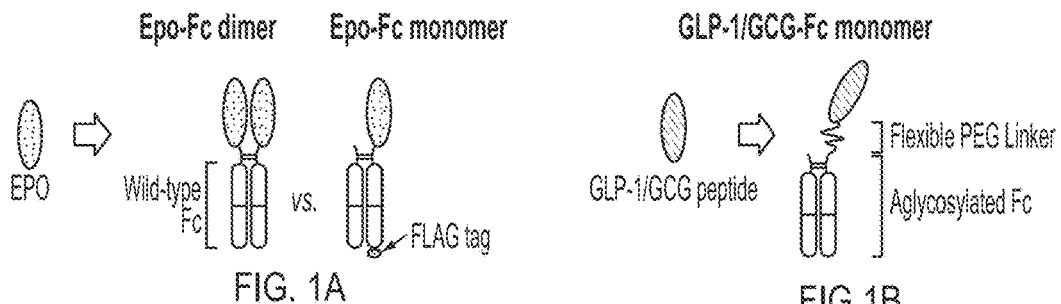
FIG. 1A
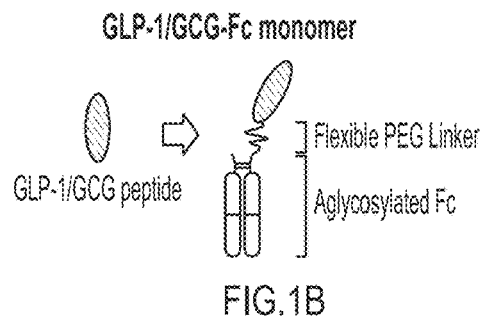
FIG. 1B
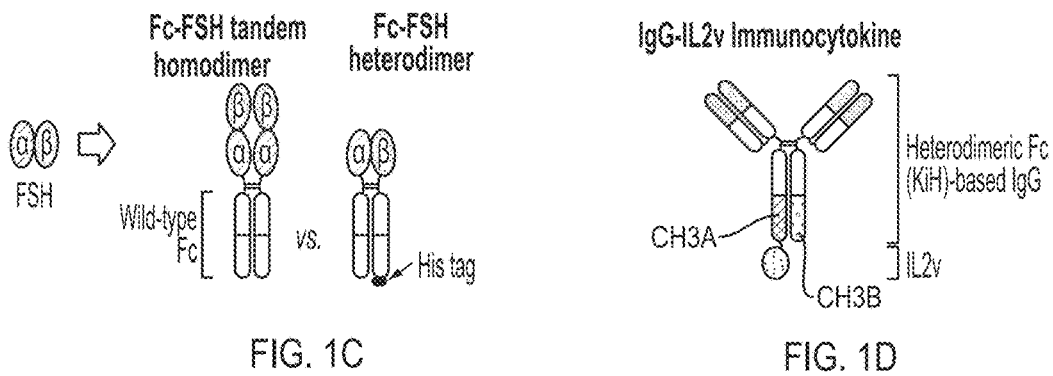
FIG. 1C
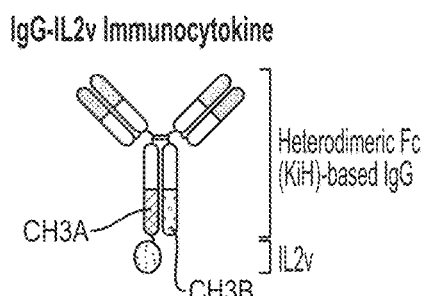
FIG. 1D
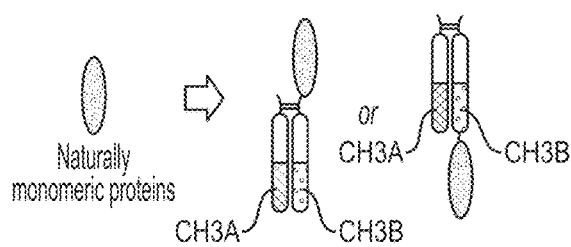
FIG. 2A  Heterodimeric Fc-based monomeric protein
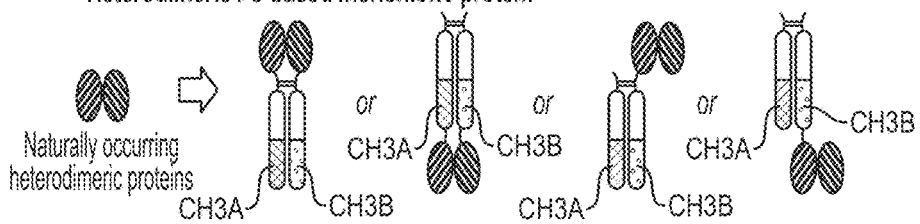
FIG. 2B  Heterodimer Fc-based heterodimeric protein
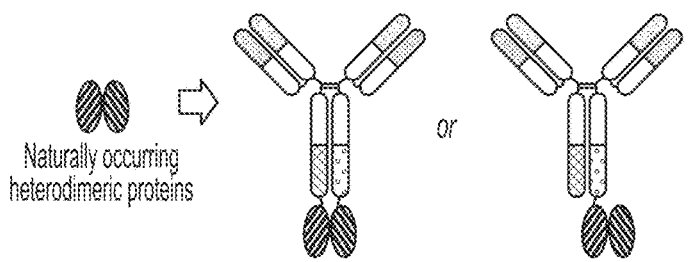
FIG. 2C  Heterodimer Fc-based heterodimeric antibody

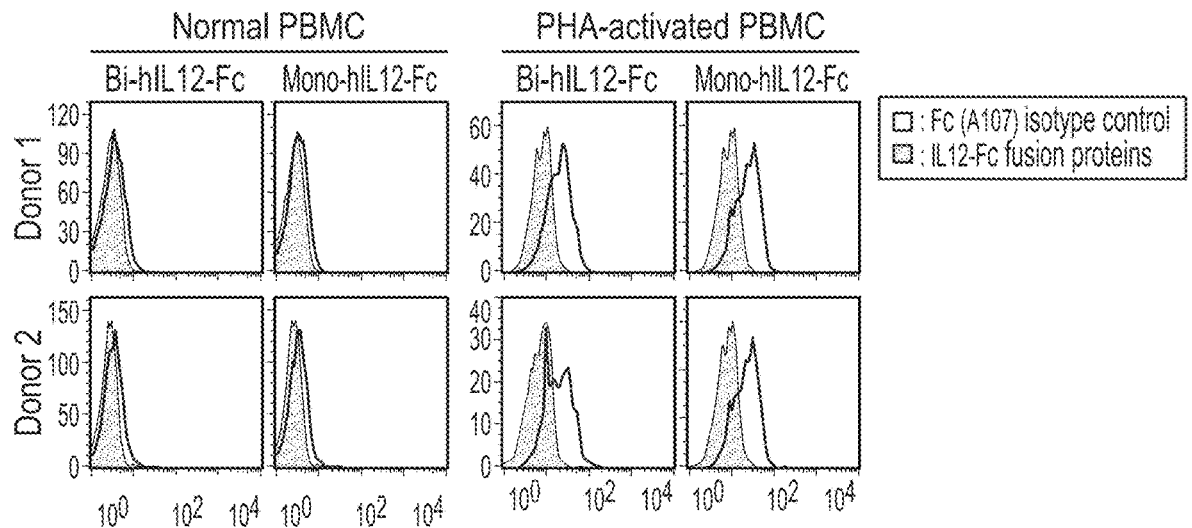
FIG. 15A  FIG. 15B
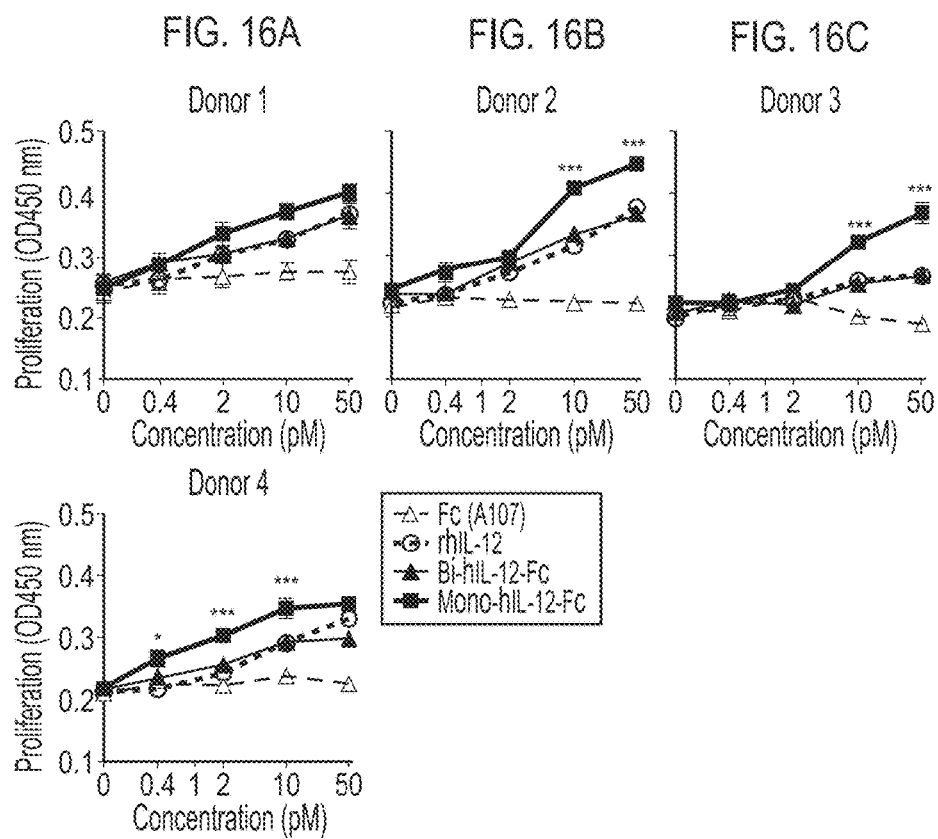
FIG. 16A  FIG. 16B  FIG. 16C
FIG. 16D

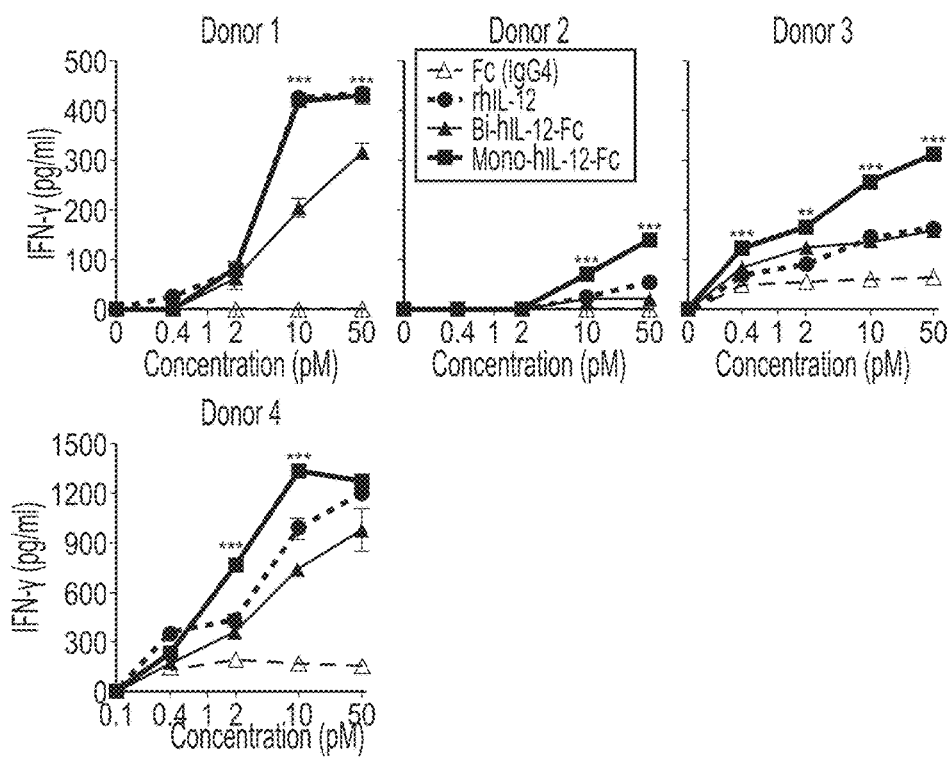
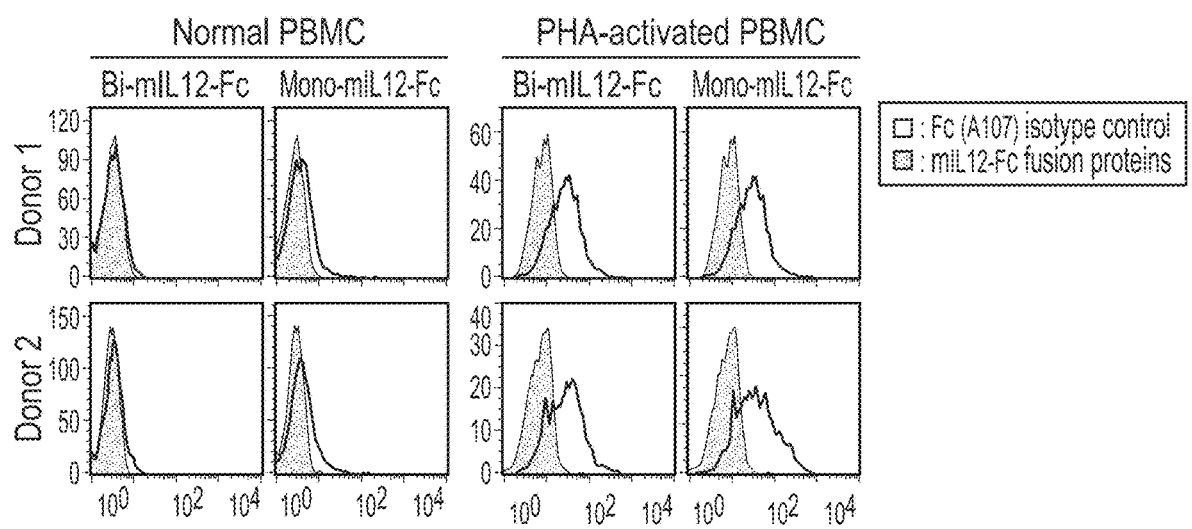

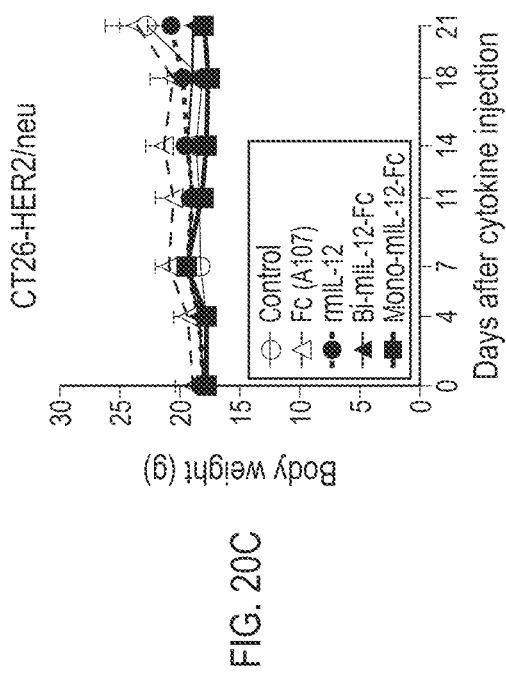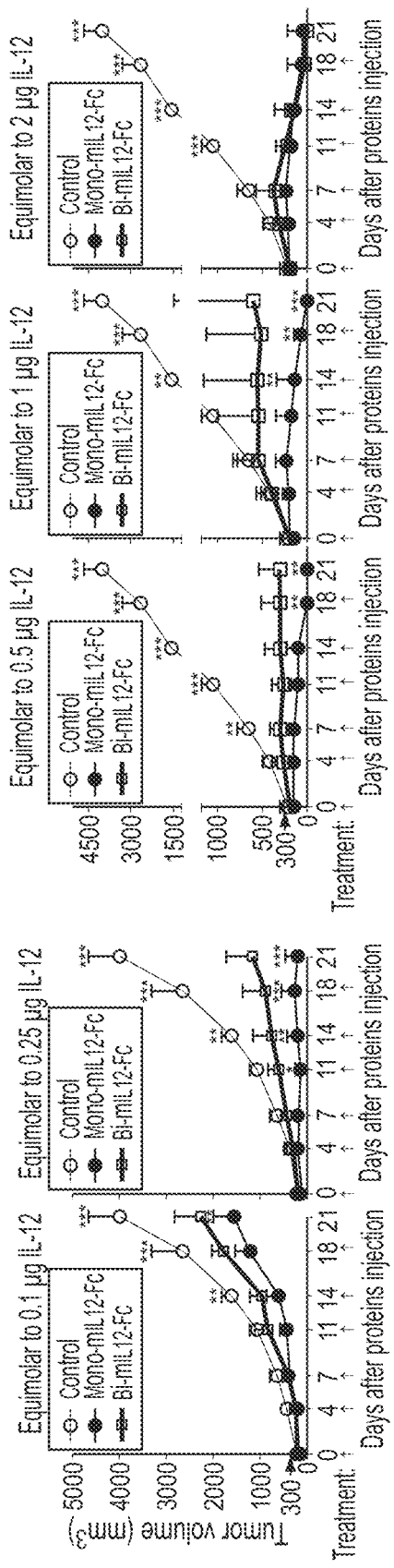

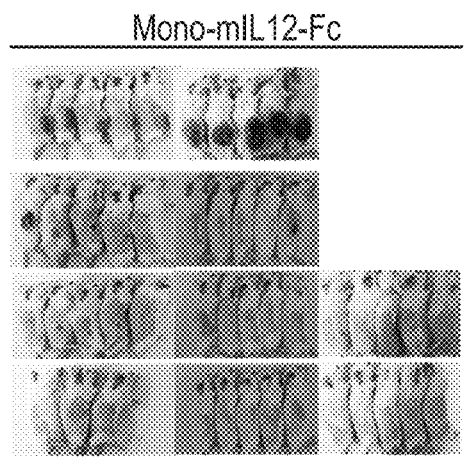 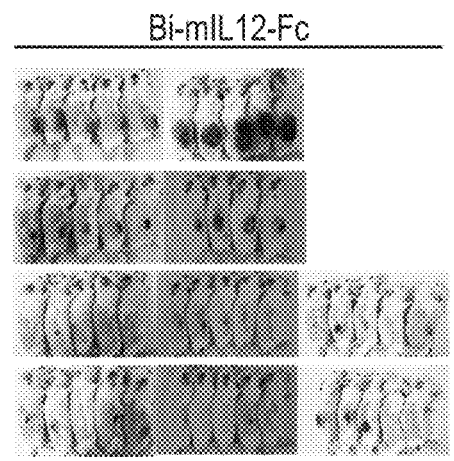 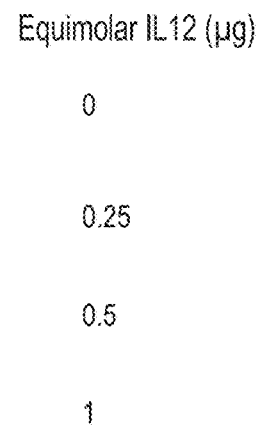
FIG. 21M    FIG. 21N
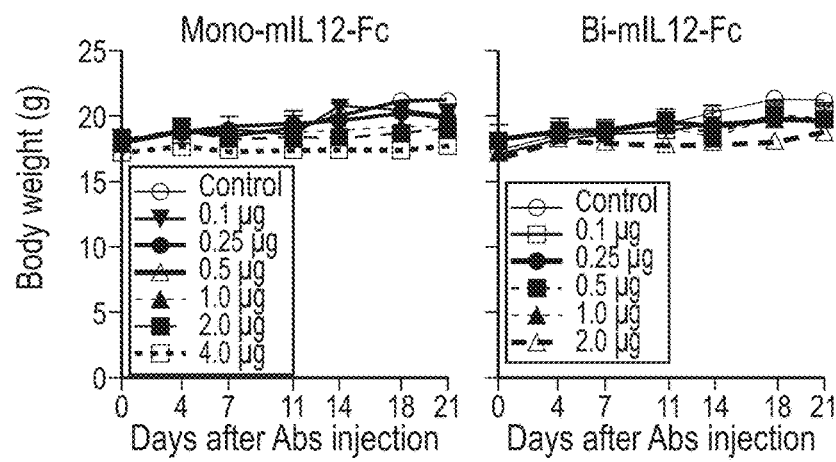
FIG. 21O    FIG. 21P

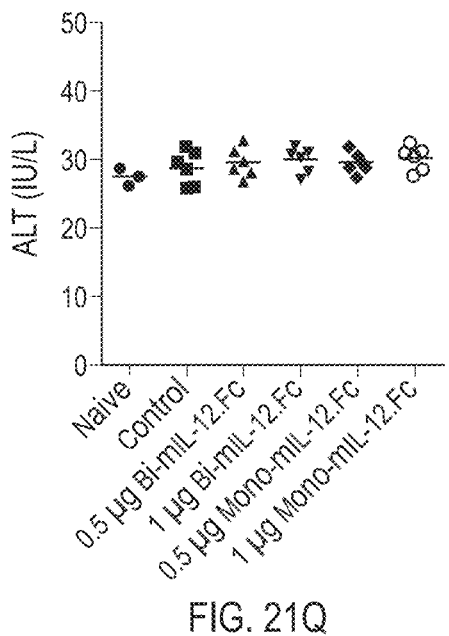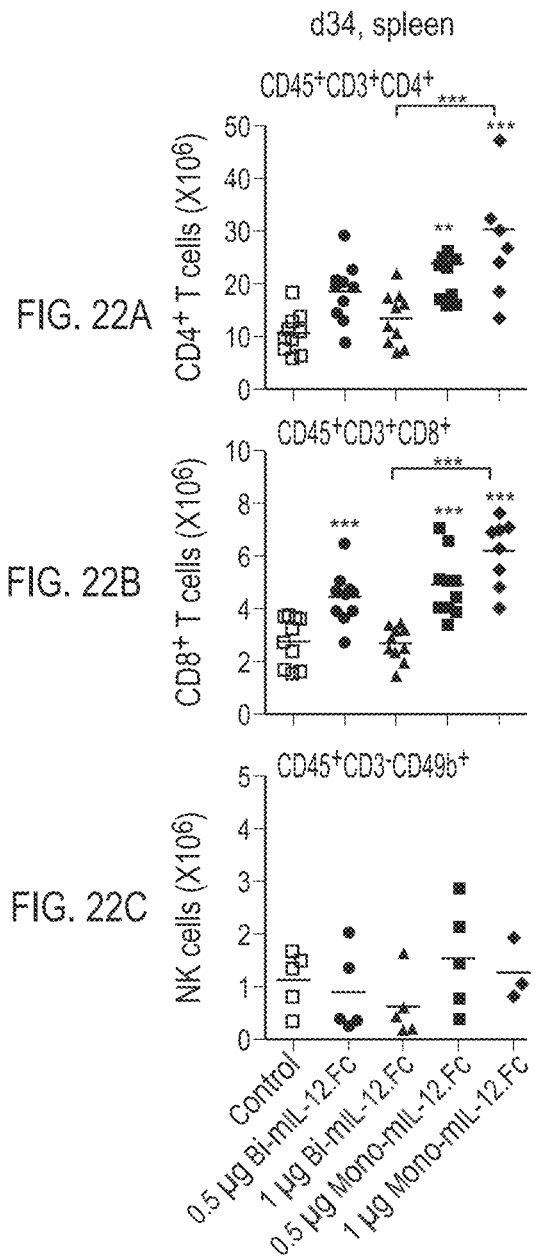

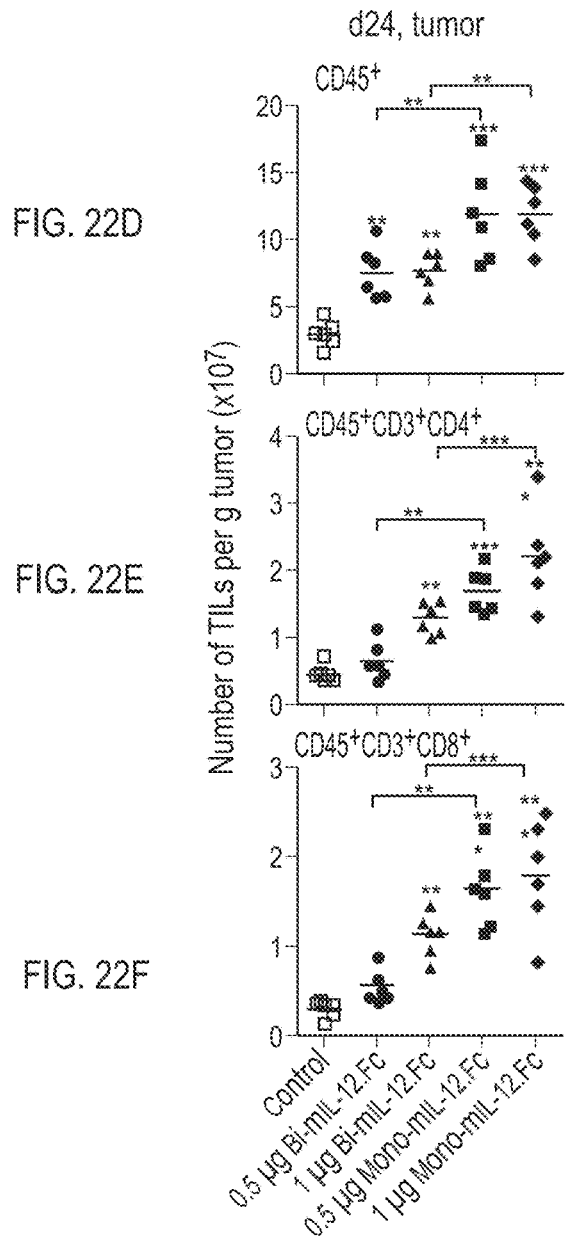
FIG. 22D
FIG. 22E
FIG. 22F
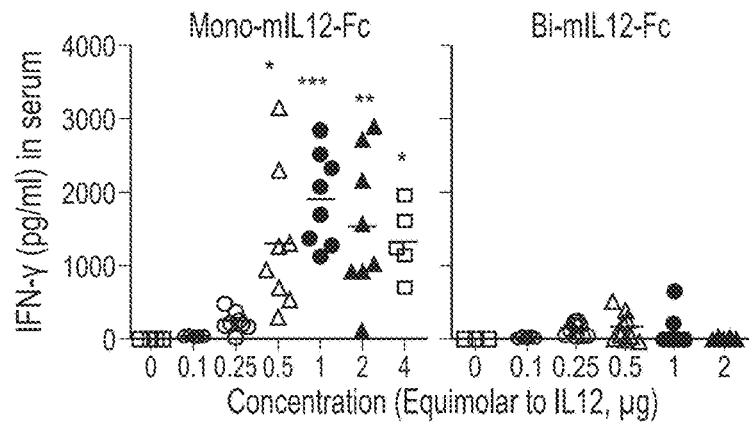
FIG. 23A   FIG. 23B

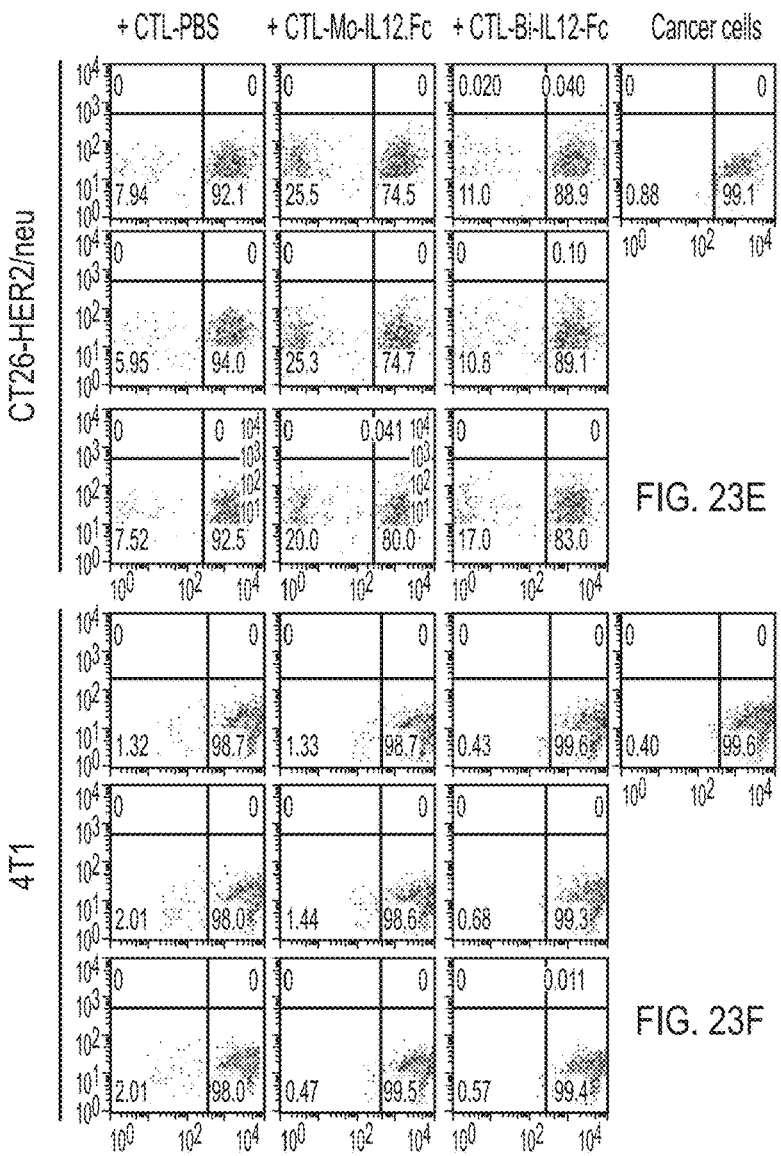
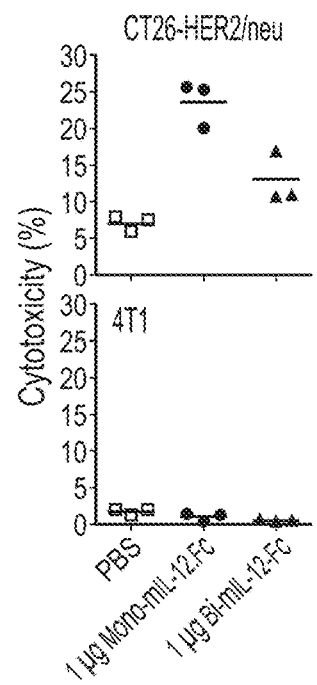
FIG. 23E
FIG. 23F
FIG. 23G
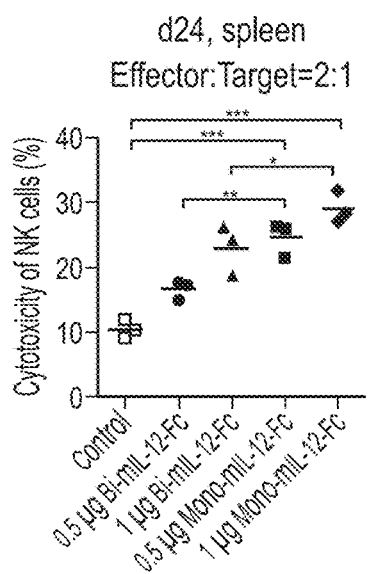
FIG. 23H

SEQUENCE LISTING

```
<160> NUMBER OF SEQ ID NOS: 20

<210> SEQ ID NO 1
<211> LENGTH: 107
<212> TYPE: PRT
<213> ORGANISM: Artificial Sequence
<220> FEATURE:
<223> OTHER INFORMATION: gamma4-EWRVT

<400> SEQUENCE: 1

Gly Gln Pro Arg Glu Pro Gln Val Tyr Thr Leu Pro Pro Ser Gln Glu
1               5                   10                  15

Glu Met Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

-continued

```
Asn Asn Tyr Lys Thr Thr Pro Pro Val Leu Asp Ser Asp Gly Ser Phe
        50                  55                  60

Phe Leu Tyr Ser Trp Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: gamma4-EWRVT

<400> SEQUENCE: 2

Gly Gln Pro Arg Glu Pro Arg Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
        50                  55                  60

Thr Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: gamma4-EWRVTs-s

<400> SEQUENCE: 3

Gly Gln Pro Arg Glu Pro Gln Val Cys Thr Leu Pro Pro Ser Gln Glu
1               5                   10                  15

Glu Met Thr Glu Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Trp Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 4
<211> LENGTH: 107
<212> TYPE: PRT
<213> ORGANISM: Artificial Sequence
```

```
<220> FEATURE:
<223> OTHER INFORMATION: gamma4-EWRVTs-s

<400> SEQUENCE: 4

Gly Gln Pro Arg Glu Pro Arg Val Tyr Thr Leu Pro Pro Cys Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: gamma4-A107

<400> SEQUENCE: 5

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: gamma4-A107

<400> SEQUENCE: 6

Gly Gln Pro Arg Glu Pro Gln Val Tyr Thr Leu Pro Pro Ser Gln Glu
1               5                   10                  15

Asn Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60
```

Thr Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
                100                 105

<210> SEQ ID NO 7
<211> LENGTH: 107
<212> TYPE: PRT
<213> ORGANISM: Artificial Sequence
<220> FEATURE:
<223> OTHER INFORMATION: IgG1

<400> SEQUENCE: 7

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 8
<211> LENGTH: 107
<212> TYPE: PRT
<213> ORGANISM: Artificial Sequence
<220> FEATURE:
<223> OTHER INFORMATION: gamma1-A107

<400> SEQUENCE: 8

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Glu Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 9
<211> LENGTH: 107
<212> TYPE: PRT
<213> ORGANISM: Artificial Sequence
<220> FEATURE:
<223> OTHER INFORMATION: gamma1-A107

-continued

<400> SEQUENCE: 9

Gly Gln Pro Arg Glu Pro Gln Val Tyr Thr Leu Pro Pro Ser Arg Asp
1               5                   10                  15

Asn Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: IgG2

<400> SEQUENCE: 10

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: gamma2-A107

<400> SEQUENCE: 11

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Glu Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: gamma2-A107

<400> SEQUENCE: 12

Gly Gln Pro Arg Glu Pro Gln Val Tyr Thr Leu Pro Pro Ser Arg Glu
1               5                   10                  15

Asn Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: IgG3

<400> SEQUENCE: 13

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Met Glu Trp Glu Ser Ser Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: gamma3-A107

<400> SEQUENCE: 14

Gly Gln Pro Arg Glu Pro Gln Val Tyr Thr Leu Pro Pro Ser Arg Glu

```
            1               5                  10                 15
Glu Met Thr Lys Asn Gln Val Ser Leu Thr Cys Leu Val Glu Gly Phe
                20                 25                 30

Tyr Pro Ser Asp Ile Ala Met Glu Trp Glu Ser Ser Gly Gln Pro Glu
            35                 40                 45

Asn Asn Tyr Lys Thr Thr Pro Pro Val Leu Asp Ser Asp Gly Ser Phe
        50                 55                 60

Phe Leu Tyr Ser Trp Leu Thr Val Asp Lys Ser Arg Trp Gln Gln Gly
65                  70                 75                 80

Asn Ile Phe Ser Cys Ser Val Met His Glu Ala Leu His Asn His Tyr
                85                 90                 95

Thr Gln Lys Ser Leu Ser Leu Ser Pro Gly Lys
                100                105

<210> SEQ ID NO 15
<211> LENGTH: 107
<212> TYPE: PRT
<213> ORGANISM: Artificial Sequence
<220> FEATURE:
<223> OTHER INFORMATION: gamma3-A107

<400> SEQUENCE: 15

Gly Gln Pro Arg Glu Pro Gln Val Tyr Thr Leu Pro Pro Ser Arg Glu
1               5                  10                 15

Asn Met Thr Lys Asn Gln Val Ser Leu Thr Cys Leu Val Lys Gly Phe
                20                 25                 30

Tyr Pro Ser Asp Ile Ala Met Glu Trp Glu Ser Ser Gly Gln Pro Glu
            35                 40                 45

Asn Asn Tyr Lys Thr Thr Pro Pro Val Leu Val Ser Asp Gly Ser Phe
        50                 55                 60

Thr Leu Tyr Ser Lys Leu Thr Val Asp Lys Ser Arg Trp Gln Gln Gly
65                  70                 75                 80

Asn Ile Phe Ser Cys Ser Val Met His Glu Ala Leu His Asn His Tyr
                85                 90                 95

Thr Gln Lys Ser Leu Ser Leu Ser Pro Gly Lys
                100                105

<210> SEQ ID NO 16
<211> LENGTH: 107
<212> TYPE: PRT
<213> ORGANISM: Artificial Sequence
<220> FEATURE:
<223> OTHER INFORMATION: IgG4

<400> SEQUENCE: 16

Gly Gln Pro Arg Glu Pro Gln Val Tyr Thr Leu Pro Pro Ser Gln Glu
1               5                  10                 15

Glu Met Thr Lys Asn Gln Val Ser Leu Thr Cys Leu Val Lys Gly Phe
                20                 25                 30

Tyr Pro Ser Asp Ile Ala Val Glu Trp Glu Ser Asn Gly Gln Pro Glu
            35                 40                 45

Asn Asn Tyr Lys Thr Thr Pro Pro Val Leu Asp Ser Asp Gly Ser Phe
        50                 55                 60

Phe Leu Tyr Ser Arg Leu Thr Val Asp Lys Ser Arg Trp Gln Glu Gly
65                  70                 75                 80

Asn Val Phe Ser Cys Ser Val Met His Glu Ala Leu His Asn His Tyr
                85                 90                 95
```

Thr Gln Lys Ser Leu Ser Leu Ser Leu Gly Lys
            100                 105

<210> SEQ ID NO 17
<211> LENGTH: 306
<212> TYPE: PRT
<213> ORGANISM: Artificial Sequence
<220> FEATURE:
<223> OTHER INFORMATION: Mature human IL-12

<400> SEQUENCE: 17

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Arg Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 18
<211> LENGTH: 197
<212> TYPE: PRT
<213> ORGANISM: Artificial Sequence
<220> FEATURE:

<223> OTHER INFORMATION: Mature human IL-12

<400> SEQUENCE: 18

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Val Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 19
<211> LENGTH: 313
<212> TYPE: PRT
<213> ORGANISM: Artificial Sequence
<220> FEATURE:
<223> OTHER INFORMATION: Mature mouse IL-12

<400> SEQUENCE: 19

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Pro Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Lys Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310

<210> SEQ ID NO 20
<211> LENGTH: 193
<212> TYPE: PRT
<213> ORGANISM: Artificial Sequence
<220> FEATURE:
<223> OTHER INFORMATION: Mature mouse IL-12

<400> SEQUENCE: 20

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

```
Asp Pro Tyr Arg Val Lys Met Lys Leu Cys Ile Leu Leu His Ala Phe
            165                 170                 175
Ser Thr Arg Val Val Thr Ile Asn Arg Val Met Gly Tyr Leu Ser Ser
            180                 185                 190
Ala
```

HETERODIMERIC FC-FUSED CYTOKINE AND PHARMACEUTICAL COMPOSITION COMPRISING THE SAME

CROSS-REFERENCE TO RELATED APPLICATIONS

This application is a divisional patent application under 35 U.S.C. § 120 of U.S. patent application Ser. No. 16/323,839, filed on Feb. 7, 2019 (now U.S. Pat. No. 10,696,722), which application is a U.S. national stage application under 35 U.S.C. § 371 of International Application No. PCT/KR2017/008676, filed on Aug. 10, 2017, which claims priority to and the benefit of Korean Patent Application No. 10-2016-0101823, filed on Aug. 10, 2016 and Korean Patent Application No. 10-2017-0101594, filed on Aug. 10, 2017, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on May 26, 2020, is named DFY-300D1_SL.txt and is 25,787 bytes in size.

TECHNICAL FIELD

The present invention relates to a heterodimeric Fc-fused protein comprising a first Fc region and a second Fc region of an immunoglobulin Fc pair and a physiologically active protein, wherein one or more subunits of the physiologically active protein are linked to one or more ends of the N-terminus or C-terminus of the first Fc region and/or the second Fc region, and CH3 domains of the first Fc region and the second Fc region are mutated so as to promote Fc heterodimer formation, and a pharmaceutical composition comprising the heterodimeric Fc-fused protein.

The heterodimeric Fc-fused protein according to the present invention has an advantage in that it can retain the activity of a naturally occurring physiologically active protein, which is composed of two or more different subunit proteins and thereby exhibit the intact biological activity by forming a assembled protein, because each subunit of the protein can be separately fused to each chain of heterodimeric Fc of immunoglobulin such that the fused protein can maintain the naturally occurring form and structure to the highest possible degree.

When the heterodimeric Fc-fused protein according to the present invention is used, there is an advantage in that the in vivo half-life of the physiologically active protein contained in the heterodimeric Fc-fused protein can be significantly increased due to the Fc-mediated long half-life such that the physiological activities thereof in vivo can be long-lasting.

In addition, the heterodimeric Fc-fused protein according to the present invention has a structure in which one or more subunits of the physiologically active protein are fused to the N-terminus or C-terminus of an immunoglobulin heterodimeric Fc, and the heterodimeric Fc-fused protein is easily purified after its expression, compared to a wild-type Fc-based fusion protein.

BACKGROUND ART

Naturally occurring human antibodies (immunoglobulin G (IgG), IgM, IgD, IgE, and IgA) are each present as an assembly of two heavy chains having the same amino acid sequence and two light chains having the same sequence. In this regard, homodimerization between the two identical heavy chains is induced by the non-covalent interactions between the constant region terminal domains (CH3 domains in IgG, IgD and IgA, CH4 domains in IgM, and CH2 and CH4 domains in IgE) and the disulfide bond between hinge domains.

Antibody heterodimeric Fc technology is a technology that makes heterodimeric fragment crystallizable (Fc) of immunoglobulin heavy chain constant regions by modifications to the CH3 domain interface, with different mutations on each domain such that the engineered Fc fragments, carrying the CH3 variant pair, preferentially form Fc heterodimers in naturally occurring antibodies (IgG, IgM, IgA, IgD, and IgE) rather than the Fc homodimers. More specifically, it is a technology that induces mutations in two different CH3 domains of Fc by genetic engineering, such that the two Fc fragments form a heterodimer with minimal sequence variations while they have tertiary structures very similar to those of naturally occurring antibodies (U.S. Pat. No. 7,695,936; and Korean Patent No. 1,522,954). The heterodimeric Fc technology is a platform technology for making bispecific antibodies, and CH3 domain mutants that induce Fc heterodimer formation known so far were mostly generated by introducing an asymmetric mutation pair into the CH3 domain interface by the structure-based rational design of antibody (Spreter Von Kreudenstein et al., 2014). Pioneering studies include knob-into-hole technology (Ridgway et al., 1996) from Genentech, and many multinational pharmaceutical companies, including Zymeworks (ZW1; Von Kreudenstein et al., 2013), Xencor (HA-TF; Moore G L et al., 2011) and EMD Serono (SEEDbody; Davis J H et al., 2010), have developed and reported the platform technology.

Above all, the A107 variant used in the present invention is a high-yield Fc heterodimer screened from a human antibody heterodimeric Fc library constructed using a yeast cell surface display system, and is a heterodimeric Fc variant which promotes the heterodimeric formation by inducing mutations at charged amino acids to form sterically complementary hydrophobic interactions (K409W$_{CH3A}$-D399V/F405T$_{CH3B}$) and forming hydrogen bonds (K370E$_{CH3A}$-E357N$_{CH3B}$), while retaining hydrophobic core integrity at the CH3 domain interface (Choi et al. 2016; Korean Patent Application No. 2015-0142181).

Heterodimeric Fc variants reported so far, including the A107 variant, are all based on IgG1 occupying the largest proportion of human antibody isotypes, and variants of isotypes (IgG2, IgG3, IgG4, IgA, IgM, and IgE) other than IgG1 have not been reported yet.

This is because therapeutic antibodies that are being marketed under approval of the U.S. Food and Drug Administration (FDA) mostly adopt the IgG1 isotype (Irani et al. 2015). In recent years, for immune-modulating antibodies or receptor agonist fusion proteins that do not need to have great antibody effector functions such as antibody-dependent cellular cytotoxicity (ADCC) or complement-dependent cellular cytotoxicity (CDC), the development of therapeutic proteins based on IgG2 or IgG4 whose effector functions are significantly lower than those of IgG1 have been made.

Meanwhile, physiologically active proteins mostly have small sizes, and thus have the disadvantage of having a short in vivo half-life. In order to solve this disadvantage, there has been an attempt to conjugate PEG (polyethylene glycol) or the like, or fusion to an antibody Fc (crystallizable fragment) region. However, it has not yet been possible to develop physiologically active proteins whose activity is efficiently and sufficiently maintained for a long period of time.

In particular, for proteins composed of two or more different subunits, wherein the two or more different subunits form a protein complex to exhibit physiological activity, it has never been possible to develop Fc-fused proteins which are formed to have naturally occurring original protein complex structures with wild type Fc because wild type Fc-fused protein forms homodimer due to the homodimeric nature of Fc. Thus, wild type Fc is not suitable for Fc fusion for heterodimeric or heterooligomeric proteins to properly exhibit the activity of the original proteins and sufficiently maintain their activity for a long period of time.

Under this technical background, the present inventors have constructed heterodimer variants comprising Fc regions derived not only from IgG1, but also from other isotype antibodies such as IgG2, IgG3 and IgG4, which were previously not reported, and have used these heterodimer variants to develop a novel therapeutic fusion protein in the form of a heterodimeric Fc-fused protein wherein one or more subunits of a protein, which is composed of two or more different subunits and in which two or more subunits exhibit physiological activity by forming a protein complex, are genetically fused to the terminus of the Fc region, thereby completing the present invention.

In particular, in the present invention, preferably, interleukin-12 (IL-12) can be used as the protein which is composed of two different subunits, p35 and p40, wherein the two subunits exhibit physiological activity by forming the IL-12 protein.

IL-12 can directly kill tumors by increasing the activity of immune cells such as cytotoxic T lymphocytes (CTLs) or natural killer cells (NKs) among immune cells, or can inhibit tumorigenesis by activating immune responses through secretion of pro-inflammatory cytokines such as interferon-gamma (IFN-y) in tumor microenvironments where the immune responses are inhibited. Thus, IL-12 has been much studied as an anti-cancer cytokine (Lasek et al., 2014). However, in the development of therapeutic methods using IL-12, the short half-life of the cytokine itself necessitates frequent administration which can lead to toxicity. For this reason, studies have been conducted to fuse IL-12 with an antibody or Fc in order to use it as long-acting IL-12 (Tugues et al., 2015). However, in these studies, a problem arises in that, due to the fusion of a wild-type Fc-based antibody that forms a homodimer by the interaction between CH3 domains, the fused IL12 protein is bivalent, unlike an endogenous monovalent form of IL-12, and for this reason, the wild type Fc-based antibody fused IL-12 shows poor physiological activity than endogenous IL-12, or unwanted localization appears due to avidity-driven increased binding of IL-12 to immune cells (Tzeng et al., 2015; Dumont et al., 2006).

Therefore, in an effort to make a monovalent fusion protein using a wild-type antibody or an Fc region, as shown in FIGS. 1(A) to 1(C), there has been used a method of constructing a fusion protein through a strategy such as fusing a selective tag for additional purification only to the C-terminus of a single Fc region or fusing an Fc region and a protein to each other after separately purifying them with high purity. However, this method is not only very costly to produce a large amount of protein, but also requires research to optimize an additional purification process.

However, the use of a heterodimeric Fc-fused protein according to the present invention makes it possible to easily produce a monovalent heterodimeric Fc-fused protein as shown in FIGS. 2A-2C without needing to optimize an additional purification process.

DISCLOSURE OF INVENTION

Technical Problem

It is an object of the present invention to provide a novel heterodimeric Fc-fused protein, the protein of which is composed of one, two, or more different subunits and thereby exhibits the intact biological activity by forming the assembled protein, and thus can maintain the natural physiological activity of the fused protein thereof in vivo for a long period of time.

In particular, the heterodimeric Fc-fused protein according to the present invention is formed such that it can retain the activity of a naturally occurring physiologically active protein, in which two or more subunits assemble together to form a protein to exhibit physiological activity, such that the fused protein can maintain the naturally occurring form and structure to the highest possible degree.

Further, the heterodimeric Fc-fused protein according to the present invention has an advantage in that the in vivo half-life of the physiologically active protein contained in the heterodimeric Fc-fused protein can be significantly increased due to the Fc-mediated long half-life such that the physiological activities thereof in vivo can be long-lasting.

Another object of the present invention is to provide a pharmaceutical composition comprising the above-described heterodimeric Fc-fused protein, and a composition and a therapeutic method for treating diseases, particularly cancer, using the same.

Technical Solution

To achieve the above object, the present invention provides a heterodimeric Fc-fused protein comprising a first Fc region and a second Fc region of an immunoglobulin Fc pair and a physiologically active protein, wherein the physiologically active protein is composed of two or more different subunits, wherein the two or more different subunits exhibit physiological activity by forming a protein complex, wherein the subunits of a physiologically active protein are linked or genetically fused to one or more ends of the N-terminus or C-terminus of the first Fc region and/or the second Fc region, wherein the CH3 domains of the first Fc region and the second Fc region are mutated so as to promote Fc heterodimer formation.

The present invention also provides a pharmaceutical composition comprising the above-described heterodimeric Fc-fused protein, and a composition and a therapeutic method for treating diseases, particularly cancer, using the same.

BRIEF DESCRIPTION OF THE DRAWINGS

FIGS. 1A to 1C illustrate conventional strategies for obtaining monomeric and heterodimeric fusion proteins using wild-type Fc of human IgG antibody. FIG. 1A is an illustrative diagram of a wild-type Fc-based Epo-Fc dimer and a wild-type Fc-based Epo-Fc monomer. FIG. 1B is an illustrative diagram of an aglycosylated Fc-fused GLP-1/GCG monomeric peptide, generated by the LAPScovery technology. FIG. 1C is an illustrative diagram of a wild-type Fc-based Fc-FSH tandem homodimer and a wild-type Fc-based Fc-FSH heterodimer. Epo, erythropoietin; GLP-1/GCG, glucagon-like peptide-1/glucagon; FSH, Follicle-stimulating hormone.

FIG. 1D is an illustrative diagram of an exemplary antibody-cytokine (immunocytokine) constructed by fusing a monomeric cytokine (IL2) to an IgG type antibody comprising a knob-into-hole (KiH) heterodimeric Fc variant according to previous literature.

FIG. 2A illustrates monomeric fusion protein forms which may be constructed using a heterodimeric Fc. The Fc-fused monomer can easily be generated by the fusion of monomeric protein to the N- or C-terminus of one heterodimeric Fc chain. FIG. 2B illustrates heterodimeric fusion protein forms which may be constructed using a heterodimeric Fc. Potential use of heterodimeric Fc for the generation of Fc-fused monomeric or heterodimeric proteins to present the fusion partner in its naturally occurring form.

FIG. 2C illustrates a fusion protein formed by fusing a heterodimer to an IgG type human antibody comprising a heterodimeric Fc. The Fc-fused heterodimer can be generated by separate fusion of the two subunits of heterodimeric proteins to each chain of the heterodimeric Fc at the N- or C-terminus.

FIG. 15A are flow-cytometry histograms showing the results of FACS analysis performed to analyze the binding affinities of mono-hIL-12-Fc and wild-type bi-hIL-12-Fc on normal PBMCs having no IL-12 receptor. FIG. 15B are flow-cytometry histograms showing the results of FACS analysis performed to analyze the binding affinities of mono-hIL-12-Fc and wild-type bi-hIL-12-Fc on phytohaemagglutinin (PHA)-activated PBMCs in which the IL-12 receptor was induced by treatment with the mitogen PHA.

FIGS. 16A-16D show the results of a WST-1 cell proliferation assay performed using cells from donor 1 (FIG. 16A), donor 2 (FIG. 16B), donor 3 (FIG. 16C), or donor 4 (FIG. 16D) to measure the effect of various concentrations of Fc (A107), recombinant human IL-12 (rhIL-12), bi-hIL-12-Fc and mono-hIL-12-Fc on the proliferation of PHA-activated PBMCs in which the IL-12 receptor was induced by treatment with the mitogen PHA.

FIGS. 17A-17D show the results of an ELISA performed using cells from donor 1 (FIG. 17A), donor 2 (FIG. 17B), donor 3 (FIG. 17C), or donor 4 (FIG. 17D) to measure the concentration of IFN-γ in culture supernatants obtained as shown in FIG. 16.

FIG. 18A are histograms showing the results of flow cytometry analysis performed to measure the binding affinities of mono-mIL-12-Fc and bi-mIL-12-Fc on normal PBMCs having no IL-12 receptor. FIG. 18B are histograms showing the results of flow cytometry analysis performed to measure the binding affinities of mono-mIL-12-Fc and bi-mIL-12-Fc on PHA-activated PBMCs in which the IL-12 receptor was induced by treatment with the mitogen PHA, because mIL-12 cross-reacts with human IL-12R on activated human T cells and NK cells.

FIG. 20C is a graph showing the changes of mouse body weight measured at indicated time points in the experimental procedure shown in FIG. 20A.

FIGS. 21A-21E are graphs showing the results of measuring mouse tumor volume changes measured while intraperitoneally administering various concentrations (0.1 μg (FIG. 21A), 0.25 μg (FIG. 21B), 0.5 μg (FIG. 21C), 1 μg (FIG. 21D), or 2 μg (FIG. 21E)) of bi-mIL-12-Fc and mono-mIL-12-Fc, twice a week, when the tumor volume in Balb/c mice transplanted with CT26$^{HER2/Neu}$ reached 300 mm$^3$.

FIG. 21M shows pictures of tumor-bearing mice 3 days after the last administration of mono-mIL-12-Fc as described in Example 14.

FIG. 21N shows pictures of tumor-bearing mice 3 days after the last administration of bi-mIL-12-Fc as described in Example 14.

FIG. 21O is a graph showing the changes in body weight of mono-mIL 12-Fc-administered mice measured at indicated time points in the experimental procedure shown in FIGS. 21A-21E.

FIG. 21P is a graph showing the changes in body weight of bi-mIL 12-Fc-administered mice measured at indicated time points in the experimental procedure shown in FIGS. 21A-21E.

FIG. 21Q is a graph showing the results of measuring alanine aminotransferase (ALT) (which is a hepatotoxicity marker) in the blood which was collected from mouse facial veins 1 day after the last administration in FIGS. 21A-21E.

FIGS. 22A-22C are graphs showing the results of measuring increases in the number of CD4$^+$ T cells (FIG. 22A), CD8$^+$ T cells (FIG. 22B), and NK cells (FIG. 22C) in the spleens of mice sacrificed 3 days after the last administration in FIGS. 21A-21E.

FIGS. 22D-22F are graphs showing the number of total immune cells (FIG. 22D), CD4$^+$ T cells (FIG. 22E) and CD8$^+$ T cells (FIG. 22F) that infiltrated the tumor in mice sacrificed 3 days after the third administration in FIGS. 21A-21E.

FIGS. 23A-23B show the results of an ELISA performed to measure the serum levels of IFN-γ in CT26$^{HER2/neu}$ tumor bearing mice treated with mIL-12-Fc proteins. FIG. 23A shows the results of an ELISA performed to measure the serum levels of IFN-γ in CT26$^{HER2/neu}$ tumor bearing mice treated with mono-mIL-12-Fc. FIG. 23B shows the results of an ELISA performed to measure the serum levels of IFN-γ in CT26$^{HER2/neu}$ tumor bearing mice treated with bi-mIL-12-Fc. Mouse serum was separated after clotting blood collected from mouse facial veins at 24 hours after the last administration in FIGS. 21A-21E.

FIGS. 23E-23F are flow cytometry dot plots showing the cytotoxic activity of splenic CD8$^+$ T cells isolated from CT26-HER2/neu tumor-bearing mice treated with mIL-12-Fc proteins, analyzed 3 days after the third administration in FIGS. 21A-21E, followed by 4 h of culture with CT26$^{HERS/Neu}$ cancer cells expressing tumor antigen and 4T1 cells not expressing tumor antigen.

FIG. 23G are graphs showing the cytotoxic activity of splenic CD8$^+$ T cells isolated from CT26-HER2/neu tumor-bearing mice treated with mIL-12-Fc proteins, analyzed 3 days after the third administration in FIGS. 21A-21E, followed by 4 h of culture with CT26$^{HERS/Neu}$ cancer cells expressing tumor antigen and 4T1 cells not expressing tumor antigen.

FIG. 23H is a graph showing the results of measuring the cytotoxic effect of natural killer cells, isolated from the spleen of mice sacrificed 3 days after the third administration in FIGS. 21A-21E, against CT26$^{HERS/Neu}$ cancer cells.

BEST MODE FOR CARRYING OUT THE INVENTION

Figure 3:
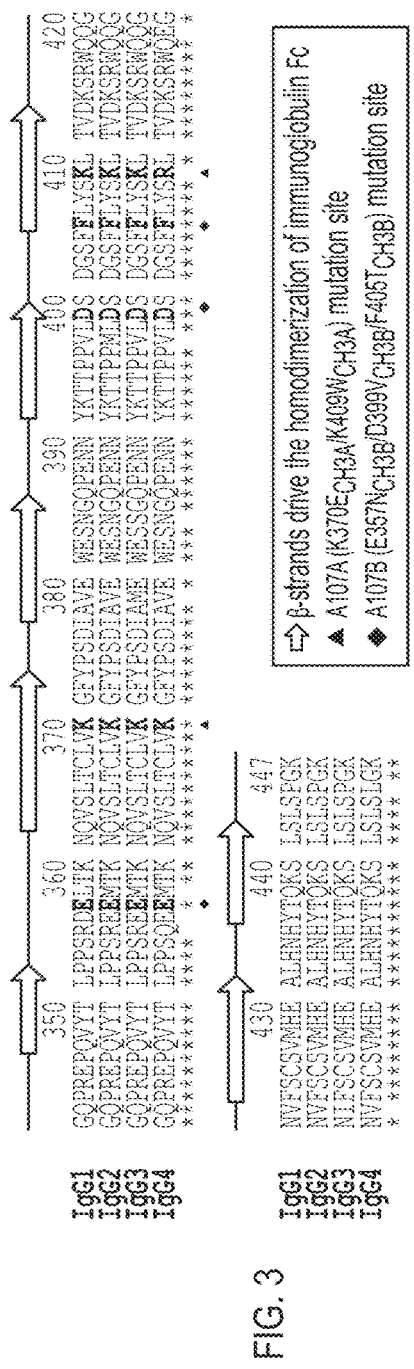
FIG. 3 shows the sequence alignment of CH3 domain of human IgG isotype antibodies (hIgG1, hIgG2, hIgG3, hIgG4) with highlights of the mutated residues in A107 heterodimeric Fc variant (K370E/K409W$_{CH3A}$-E357N/D399V/F405T$_{CH3B}$).

Unless defined otherwise, all the technical and scientific terms used herein have the same meaning as those generally understood by one of ordinary skill in the art to which the invention pertains. Generally, the nomenclature used herein and the experiment methods, which will be described below, are those well-known and commonly employed in the art.

In one aspect, the present invention relates to a heterodimeric Fc-fused protein comprising a first Fc region and a second Fc region of an immunoglobulin Fc pair and a physiologically active protein, wherein the physiologically active protein is composed of two or more different subunits, wherein the two or more different subunits exhibit physiological activity by forming a protein complex, wherein one or more subunits of a physiologically active protein are linked to one or more ends of the N-terminus or C-terminus of the first Fc region and/or the second Fc region, wherein CH3 domains of the first Fc region and the second Fc region are mutated so as to promote heterodimer formation.

As used herein, the term "Fc region" or "heavy chain constant region" means a region comprising an immunoglobulin CH2 domain, a CH3 domain and a hinge domain. However, for IgE, the term means a region comprising a CH2 domain, a CH3 domain, a CH4 domain and a hinge domain.

As used herein, the expression "the first Fc region and the second Fc region are mutated so as to promote heterodimer formation" means that a naturally occurring antibody has a homodimeric form in which two Fc regions have the same sequence, and a portion of these Fc region sequences is mutated, so that heterodimer formation can be promoted through a specific non-covalent interaction between the first Fc region and the second Fc region, or homodimer formation can be reduced, or preferably can hardly occur.

Preferably, "the first Fc region and the second Fc region are mutated so as to promote heterodimer formation" may include "each of CH3 domains contained in the first Fc region and second Fc region from immunoglobulin is mutated so as to promoter Fc heterodimer formation".

In the present invention, "heterodimeric Fc or Fc heterodimer" comprises the first Fc region and the second Fc region, and the first Fc region and the second Fc region mean heterodimers in which CH3 domains of the first Fc region and the second Fc region are mutated so as to promote Fc heterodimer formation.

In the present invention, each of the first Fc region and the second Fc region may be derived from an Fc region selected from the group consisting of human IgG1, IgG2, IgG3, IgG4, IgM, IgA, IgD and IgE, and preferably each of the first Fc region and the second Fc region is derived from IgG1, IgG2, IgG3 or IgG4.

In addition, the first Fc region and the second Fc region may be derived from an isotype antibody.

In another aspect, the mutation of CH3 domain may include one or more mutations selected from the following group (wherein all mutation positions in the present invention are numbered according to the EU index): (1) substitution of the amino acid residue at position K370 in the CH3 domain of the first Fc region; and substitution of the amino acid residue at position(s) E357 and/or S364 in the CH3 domain of the second Fc region; and/or (2) substitution of the amino acid residue at position K409 in the CH3 domain of the first Fc region; and substitution of the amino acid residue at position(s) F405 and/or D399 in the CH3 domain of the second Fc region.

Preferably, the substitution of amino acid residue at position K370 in the CH3 domain of the first Fc region may be K370E, K370R, K370M, K370D or K370H, substitution of the amino acid residue at position E357 in the CH3 domain of the second Fc region may be E357N, E357D, E357A, E357I, E357G or E357M, and substitution of the amino acid residue at position S364 in the CH3 domain of the second Fc region may be S364T or S364W.

In addition, substitution of the amino acid residue at position K409 in the CH3 domain of the first Fc region may be K409W, substitution of the amino acid residue at position F405 in the CH3 domain of the second Fc region may be F405T, and substitution of the amino acid residue at position D399 in the CH3 domain of the second Fc region may be D399V.

The amino acid residue mutation such as K370E means that K at position 370 is mutated to E, and the mutation of all amino acid residues in the present invention is used as the same meaning as described above.

Most preferably, the mutation of the CH3 domain of the first Fc region or the second Fc region may include one or more mutations selected from the following group (wherein mutation positions are numbered according to the EU index.): (1) a substitution K370E, K370R, K370M, K370D or K370H of the amino acid residue at position K370 in the CH3 domain of the first Fc region; (2) a substitution E357N, E357D, E357A, E357I, E357G or E357M of the amino acid residue at position E357 in the CH3 domain of the second Fc region, and substitution S364T or S364W of the amino acid residue at position S364 in the CH3 domain of the second Fc region; (3) a substitution K409W of the amino acid residue at position K409 in the CH3 domain of the first Fc region; and (4) a substitution F405T of the amino acid residue at position F405 in the CH3 domain of the second Fc region, and substitution D399V of the amino acid residue at position D399 in the CH3 domain of the second Fc region.

The CH3 domains in the first Fc region and the second Fc region may further include the following residue: (i) cysteine (C) substituted at position Y349 in the CH3 domain of the first Fc region; and (ii) cysteine (C) substituted at position S354 in the CH3 domain of the second Fc region.

In still another aspect, mutation of the CH3 domain may include one or more mutations selected from the following group: (1) a substitution of the amino acid residue at position K360 in the CH3 domain of the first Fc region; and substitution of the amino acid residue at position E347 in the CH3 domain of the second Fc region; and/or (2) a substitution of the amino acid residue at position K409 in the CH3 domain of the first Fc region; and substitution of the amino acid residue at position(s) F405 and D399 in the CH3 domain of the second Fc region.

Preferably, the substitution of the amino acid residue at position K360 in the CH3 domain of the first Fc region may be K360E, and substitution of the amino acid residue at position E347 in the CH3 domain of the second Fc region may be E347R.

Substitution of the amino acid residue at position K409 in the CH3 domain of the first Fc region may be K409W, substitution of the amino acid residue at position F405 in the CH3 domain of the second Fc region may be F405T, and substitution of the amino acid residue at position D399 in the CH3 domain of the second Fc region may be D399V.

Most preferably, the mutation of the CH3 domain of the first Fc region or the second Fc region may include one or more mutations selected from the following group (wherein mutation positions are numbered according to the EU index): (1) a substitution K360E of the amino acid residue at position K360 in the CH3 domain of the first Fc region; (2) a substitution E347R of the amino acid residue at position E347 in the CH3 domain of the second Fc region; (3) a substitution K409W of the amino acid residue at position K409 in the CH3 domain of the first Fc region; and (4) a substitution F405T of the amino acid residue at position F405 in the CH3 domain of the second Fc region, and substitution D399V of the amino acid residue at position D399 in the CH3 domain of the second Fc region.

The CH3 domains in the first Fc region and the second Fc region may further include the following residue: (i) cysteine (C) substituted at position Y349 in the CH3 domain of the first Fc region; and (ii) cysteine (C) substituted at position S354 in the CH3 domain of the second Fc region.

Preferably, each of the CH3 domains contained in the first Fc region and the second Fc region from immunoglobulin according to the present invention may have an amino acid sequence selected from the group consisting of the amino acid sequences represented by the following SEQ ID NOS: (1) SEQ ID NO: 1 and SEQ ID NO: 2; (2) SEQ ID NO: 3 and SEQ ID NO: 4; (3) SEQ ID NO: 5 and SEQ ID NO: 6; (4) SEQ ID NO: 8 and SEQ ID NO: 9; (5) SEQ ID NO: 11 and SEQ ID NO: 12; and (6) SEQ ID NO: 14 and SEQ ID NO: 15.

In particular, the first Fc region and second Fc region from immunoglobulin according to the present invention preferably have the sequences of IgG4 CH3 domains shown in Table 1 below.

TABLE 1

| con-figur-ation | CH3 sequence of first Fc region (EU number 341 to 447) | CH3 sequence of second Fc region (EU number 341 to 447) |
|---|---|---|
| γ4-EWRVT | GQPREPQVYTLPPSQEEMT ENQVSLTCLVKGFYPSDIA VEWESNGQPENNYKTTPPV LDSDGSFFLYSWLTVDKSR WQEGNVFSCSVMHEALHNH YTQKSLSLSLGK (SEQ ID NO: 1) | GQPREPRVYTLPPSQEEMTKNQ VSLTCLVKGFYPSDIAVEWESN GQPENNYKTTPPVLVSDGSFTL YSRLTVDKSRWQEGNVFSCSVM HEALHNHYTQKSLSLSLGK (SEQ ID NO: 2) |
| γ4-EWRVT$_{s-s}$ | GQPREPQVCTLPPSQEEMT ENQVSLTCLVKGFYPSDIA VEWESNGQPENNYKTTPPV LDSDGSFFLYSWLTVDKSR WQEGNVFSCSVMHEALHNH YTQKSLSLSLGK (SEQ ID NO: 3) | GQPREPRVYTLPPCQEEMTKNQ VSLTCLVKGFYPSDIAVEWESN GQPENNYKTTPPVLVSDGSFTL YSRLTVDKSRWQEGNVFSCSVM HEALHNHYTQKSLSLSLGK (SEQ ID NO: 4) |
| γ4-A107 | GQPREPQVYTLPPSQEEMT KNQVSLTCLVEGFYPSDIA VEWESNGQPENNYKTTPPV LDSDGSFFLYSWLTVDKSR WQEGNVFSCSVMHEALHNH YTQKSLSLSLGK (SEQ ID NO: 5) | GQPREPQVYTLPPSQENMTKNQ VSLTCLVKGFYPSDIAVEWESN GQPENNYKTTPPVLVSDGSFTL YSRLTVDKSRWQEGNVFSCSVM HEALHNHYTQKSLSLSLGK (SEQ ID NO: 6) |

In the heterodimeric Fc-fused protein according to the present invention, a subunit of the physiologically active protein may be linked only to any one end of the N-terminus or C-terminus of the first Fc region or the second Fc region, and one or more different subunits of a single physiologically active protein may be linked to each of the N-terminus and C-terminus of each of the first Fc region and the second Fc region (see FIGS. 2B and 2C).

"A subunit of the physiologically active protein is linked only to any one end of the N-terminus or C-terminus of the first Fc region or the second Fc region" means that one of the subunits of the physiologically active protein is linked only to any one of four ends of the N-terminus or C-terminus of the first Fc region or the second Fc region, and the remaining subunit(s) of the physiologically active protein is(are) linked by a linker to the subunit of physiologically active protein, which is linked to any one end of the N-terminus or C-terminus of the first Fc region or the second Fc region. The linker is preferably an amino acid linker, but is not limited thereto.

In addition, "one or more different subunits of a single physiologically active protein are linked to each of the N-terminus and C-terminus of each of the first Fc region and the second Fc region" means that one or more different subunits of a single physiologically active protein are linked to the N-terminus of each of the first Fc region and the second Fc region, one or more different subunits of a single physiologically active protein are linked to the C-terminus of each of the first Fc region and the second Fc region, or one or more different subunits of a single physiologically active protein are respectively linked to the N-terminus and C-terminus of each of the first Fc region and the second Fc region.

In the heterodimeric Fc-fused protein according to the present invention, the subunit of the physiologically active protein may be linked to the N-terminus and/or C-terminus of the first Fc region and/or the second Fc region by genetic fusion.

In still another aspect, the subunit of the physiologically active protein may be linked to the first Fc region and the second Fc region through a linker. The linker is preferably an amino acid linker, but is not limited thereto.

In yet another aspect, in the heterodimeric Fc-fused protein according to the present invention, the physiologically active protein is characterized in that it is composed of two or more different subunits, wherein the two or more different subunits exhibit physiological activity by forming a protein complex.

"The physiologically active protein is composed of two or more different subunits, wherein the two or more different subunits exhibit physiological activity by forming a protein complex" means that the physiologically active protein exhibits desired physiological activity when two or more subunits form a protein complex.

The physiologically active protein is selected from the group consisting of interleukin-12 (IL-12), interleukin-23 (IL-23), interleukin-27 (IL-27), interleukin-35 (IL-35), and follicle stimulating hormone (FSH), but is not limited thereto. Besides, it will be obvious to those skilled in the art that any physiologically active protein suitable for the purpose of the present invention may be used in the present invention.

Most preferably, the physiologically active protein according to the present invention is IL-12. A protein which is composed of two or more two different subunits, wherein the two or more different subunits exhibit physiological activity by forming a protein complex according to the present invention will now be described in detail by way of example of IL-12 which is a preferred physiologically active protein.

IL-12 is composed of two subunits, p35 (IL-12A) and p40 (IL-12B), and the physiologically active form of IL-12 is p70 which is a heterodimer of p35 and p40. IL-12 should be present in the form of p70 which is the heterodimer of p35 and p40 in order for IL-12 to exhibit the activity thereof in nature systems.

In the present invention, in order to mimic the form of naturally occurring IL-12 to the greatest possible extent, the form of a heterodimeric Fc-fused protein according to the present invention was embodied.

Specifically, as described above, in the heterodimeric Fc-fused protein comprising a first Fc region and a second Fc region according to the present invention, wherein one or more subunits of a physiologically active protein are linked to one or more ends of the N-terminus or C-terminus of the first Fc region and the second Fc region, (i) one or more subunits constituting a physiologically active protein may be linked only to any one end of the N-terminus or C-terminus of the first Fc region or the second Fc region, and the remaining subunit(s) of the physiologically active protein may be linked by a linker, or (ii) one or more different subunits of a single physiologically active protein may be respectively linked to the N-terminus and/or C-terminus of each of the first Fc region and the second Fc region".

In the above case, an example of IL-12 will be described hereinafter.

In the case of (i), the p35 or p40 subunit of IL-12 may be linked only to any one end of the N-terminus or C-terminus of the first Fc region or the second Fc region, and the remaining subunit may be linked by a linker to the p35 or p40 subunit linked to any one end of the N-terminus or C-terminus of the first Fc region or the second Fc region to form the heterodimeric Fc-fused protein (see FIGS. 2B, and 2C).

In the case of (ii), any one selected from the p35 and p40 subunits of IL-12 may be linked only to the N-terminus or C-terminus of the first Fc region, and the other subunit may be linked only to the N-terminus or C-terminus of the second Fc region to form the heterodimeric Fc-fused protein (see FIGS. 2B, and 2C).

Figures 10A, 10B, 10C:
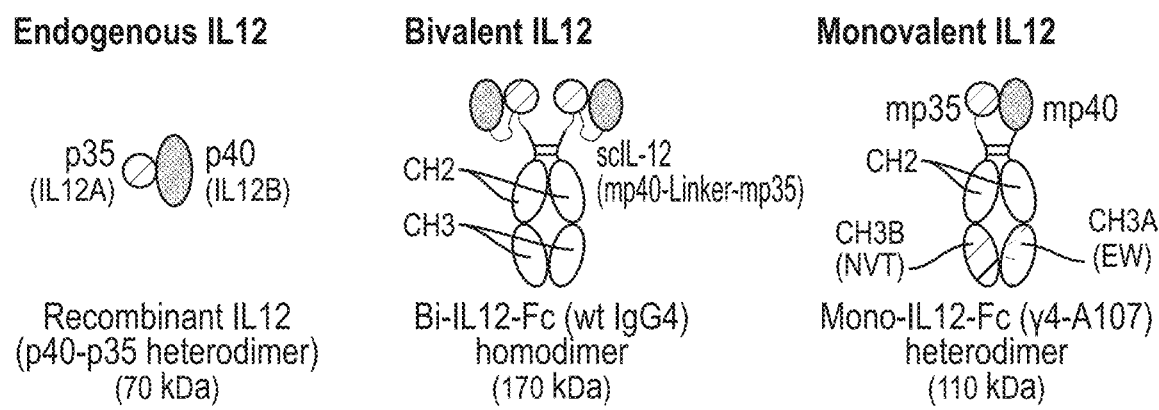
FIG. 10A is a schematic view showing the form of endogenous IL-12 cytokine to which Fc was not fused and which is used as a control in the present invention.
FIG. 10B is a schematic view showing the form of a bi-IL-12-Fc fusion protein which was obtained by fusing IL-12 cytokine to wild-type IgG4 Fc by an amino acid linker and which is used as a comparative example in the present invention.
FIG. 10C is a schematic view showing the form of a mono-IL-12-Fc fusion protein obtained by fusing IL-12 cytokine to an IgG4-based γ4-A107 variant among heterodimeric Fc variants for each isotype according to the present invention.

It was found that this form showed in vitro physiological activity similar to that of a conventional recombinant IL-12 protein while maintaining the naturally occurring original heterodimeric form (see FIGS. 2B, 2C, and 10C).

Accordingly, a preferable immunoglobulin heterodimeric Fc-fused protein according to the present invention is characterized in that the physiologically active protein is IL-12, and in that the p35 or p40 subunit of IL-12 is linked only to any one end of the N-terminus or C-terminus of the first Fc region or the second Fc region, and the remaining subunit is linked by a linker to the subunit linked to any one end of the N-terminus or C-terminus of the first Fc region or the second Fc region, or in that the p35 and p40 subunits of IL-12 are linked to each of the N-terminus and C-terminus of each of the first Fc region and the second Fc region.

In another aspect, in the heterodimeric Fc-fused protein according to the present invention, the hinge domain included in the N-terminus of each of the first Fc region and the second Fc region may be characterized in that the cysteine residues contained in the hinge domain is mutated.

Preferably, mutation of the cysteine residues in the hinge domain may be characterized in that cysteine residues in an upper hinge region, other than cysteine residues in a core hinge domain for heterodimer formation, are all substituted with serine residues, but the scope of the present invention is not limited thereto.

In addition, on the present invention, the first Fc region and the second Fc region may be included in a whole antibody form consisting of human IgG1, IgG2, IgG3, IgG4, IgM, IgA, IgD and IgE.

In the present invention, the term "whole antibody form" means an intact antibody further comprising a CH1 domain, a VH domain, a CL domain and a VL domain, in addition to the CH2 domain, CH3 domain and hinge domain (also comprising CH4 domain for IgE) in the Fc region for IgG, IgA and IgD.

In still another aspect, the present invention relates to a pharmaceutical composition comprising the heterodimeric Fc-fused protein according to the present invention. The use of the pharmaceutical composition according to the present invention may depend on the use of a physiologically active protein contained in the heterodimeric Fc-fused protein.

Preferably, the physiologically active protein contained in the heterodimeric Fc-fused protein according to the present invention may be IL-12 or one or more subunits thereof. Therefore, the present invention provides a pharmaceutical composition for treating cancer, which comprises a heterodimeric Fc-fused protein comprising IL-12 as a physiologically active protein.

A cancer that can be treated with the pharmaceutical composition for treating cancer, which comprises a heterodimeric Fc-fused protein comprising IL-12 or one or more subunits as the physiologically active protein may be selected from the group consisting of colorectal cancer, melanoma, breast cancer, pancreatic cancer, kidney cancer, prostate cancer, ovarian cancer, small intestine cancer, esophageal cancer, cervical cancer, lung cancer, lymphoma, and blood cancer, but not limited thereto.

A pharmaceutical composition according to the present invention may further comprise a pharmaceutically acceptable carrier. The term "pharmaceutically acceptable carrier" refers to a substance which can be added to the active ingredient to help formulate or stabilize the preparation and causes no significant adverse toxicological effects to the patient.

As used herein, the term "pharmaceutically acceptable carrier" refers to a carrier or diluent that does not impair the biological activity and characteristics of a heterodimeric Fc-fused protein according to the present invention without irritating a patient. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets. Other carriers are described in a literature [Remington's Pharmaceutical Sciences (E. W. Martin)].

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. The composition is preferably formulated for parenteral injection. The composition can be formulated as a solid, a solution, a microemulsion, a liposome, or other ordered structures suitable to high drug concentration. The carrier may be a solvent or dispersion medium containing, for example, water, ethanol, polyol (e.g., glycerol, propylene glycol and liquid polyethylene glycol), and suitable mixtures thereof. In some cases, the composition may contain an isotonic agent, for example, sugar, polyalcohol, for example, sorbitol or sodium chloride. Sterile injectable solutions can be prepared by the heterodimeric Fc-fused protein in the required amount in an appropriate solvent with one or a combination of ingredients enumerated above, as required, followed by sterile microfiltration. Generally, dispersions are prepared by incorporating an active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient and any additional desired ingredient from a previously sterile-filtered solution thereof.

In addition, the pharmaceutical composition according to the present invention may be orally or parenterally administered to suffering patients at a dosage and frequency that may vary with the severity of the suffering patients. The compositions may be administered to patients in need as a bolus or by continuous infusion. In another example, the pharmaceutical composition according to the present invention may be administered rectally, intravenously, subcutaneously, intrauterinely, or intracerebrovascularly, but is not limited thereto.

In addition, a pharmaceutical composition for cancer treatment, comprising an immunoglobulin heterodimeric Fc-fused protein including IL-12 can be used for combination therapy with other anticancer drugs. Other anticancer drugs are preferably cytotoxic T cells and/or natural killer (NK) cells, but not limited thereto, and all the anticancer drugs that can be used in the art to which the present invention pertains can be used for the combination therapy.

In particular, when a pharmaceutical composition for cancer treatment, comprising an immunoglobulin heterodimeric Fc-fused protein including IL-12, is used for combination therapy with cytotoxic T cells and/or natural killer (NK) cells, it may induce: (1) an increase in cytokine secretion by stimulation of the T cells or natural killer (NK) cells; (2) an increase in antibody-dependent cell-mediated cytotoxicity (ADCC) or cytotoxic T lymphocyte (CTL) response; (3) an increase in the number of cytotoxic T lymphocytes (CTLs) and/or natural killer cells; (3) an increase in lymphocyte introduction around a tumor; or (4) an increase in the IL-12R beta1 and IL-12R beta2 signaling of lymphocytes in vivo.

In yet another aspect, the present invention relates to a method for treating or preventing diseases, comprising administering, to a patient in need of treatment, a pharmaceutical composition comprising the heterodimeric Fc-fused protein according to the present invention.

Similar to the case of the composition, a disease that can be treated or prevented depends on the use of a physiologically active protein contained in the heterodimeric Fc-fused protein. Preferably, when one or more subunits of a physiologically active protein contained in the heterodimeric Fc-fused protein according to the present invention are one or more subunits of IL-12, the present invention provides a cancer treatment or prevention method for a patient suffering from a cancer, particularly a cancer selected from the group consisting of colorectal cancer, melanoma, breast cancer, pancreatic cancer, kidney cancer, prostate cancer, ovarian cancer, small intestine cancer, esophageal cancer, cervical cancer, lung cancer, lymphoma, and blood cancer.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1

Design of Antibody Fc CH3 Domain Variants for Heterodimer Formation for Each Human Immunoglobulin Isotype (Sequencing)

In order to make heterodimeric Fc fragments for each human immunoglobulin isotype by introducing CH3 domain mutations that flavor heterodimer formation, the amino acid sequence similarity between CH3 domains playing a major role in interactions for heterodimer formation was first analyzed as described below. In this regard, the heterodimeric Fc variant (A107) was generated by introducing asymmetric mutations into the CH3 homodimeric interface to generate heterodimeric CH3A:CH3B pair (in the present invention, CH3A and CH3B mean the CH3 domain of the first Fc region and the CH3 region of the second Fc region, respectively) by a strategy as published in previous literature or patent documents (Choi et al. 2016; Korean Patent Application No. 2015-0142181), such that the heterodimerization of CH3A:CH3B drive the Fc variant to form the heterodimer in high yield. FIG. 3 aligns and compares the sequences of CH3 domains for each human antibody immunoglobulin G (IgG) isotype. Each amino acid sequence was obtained from the International ImMunoGeneTics information system (IMGT; URL: http://www.imgt.org/). In particular, among various allotypes, the sequence of G3m(s,t) whose serum half-life was reported to be maintained at levels similar to those of other IgG isotypes was used for IgG3 (Stapleton N M et al., 2011).

The results of sequencing indicated that IgG4 has a sequence conserved in all isotypes, except that the amino acid at position 409 among positions into which the A107 mutation is introduced is arginine, unlike those in IgG1, IgG2 and IgG3. Accordingly, positions having the same amino acid sequence number were selected as positions for introducing the A107 mutation pair into isotypes other than IgG1. All amino acid positions in the present invention are numbered according to the EU index.

Example 2

Design of Immunoglobulin Fc CH3 Domain Variants for Heterodimer Formation for Each Human Immunoglobulin Isotype (Structural Modeling)

Figure 4:
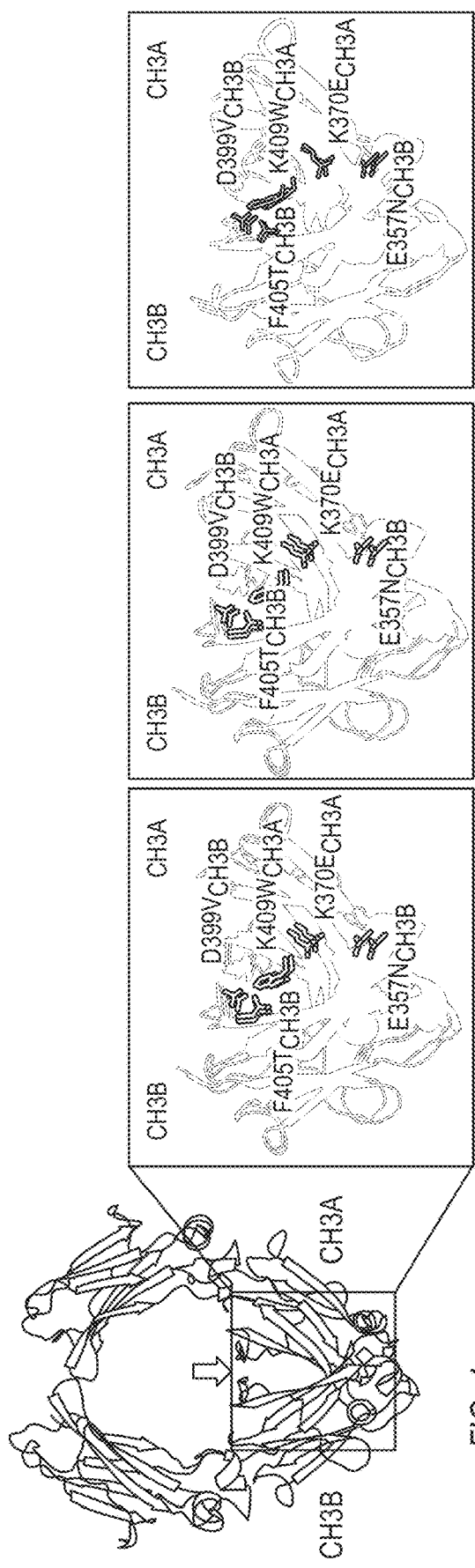
FIG. 4 shows the results of performing structural modeling of heterodimeric Fc variants for each isotype by use of sequences having induced mutations at the positions selected in FIG. 3 and analyzing the resulting modeling structures comparatively with wild-type IgG1-based A107 variants.

Before CH3 domain variants for each isotype were actually constructed, whether the A107 mutation pair could be stably introduced into the positions selected in Example 1 so as to form heterodimers was predicted through structural modeling using the variant sequences introduced with each mutation as shown in FIG. 3. Structural modeling was predicted through an online modeling server (URL: https://swissmodel.expasy.org/; Biasini M et al., 2014) using an already known immunoglobulin Fc heterodimer variant structure (PDB ID: 4X98) as a template. Each of the obtained structures was overlapped using the Pymol software, which could visualize protein structures, in order to observe the structural change of the CH3 domain and the position of the A107 mutation after introduction of the mutation. On the overlapping structure, it was seen that, even when the A107 mutation was introduced into each isotype, the structures were maintained without great changes, compared to the modeled structure of conventional A107 variants constructed based on IgG1 isotypes and forming CH3A:CH3B Fc heterodimers. In particular, it was shown that the directions of the introduced A107 mutation amino acid residues were almost consistent and that the distances for interaction between the mutated amino acids were also maintained at similar levels (see FIG. 4).

Example 3

Figure 5:
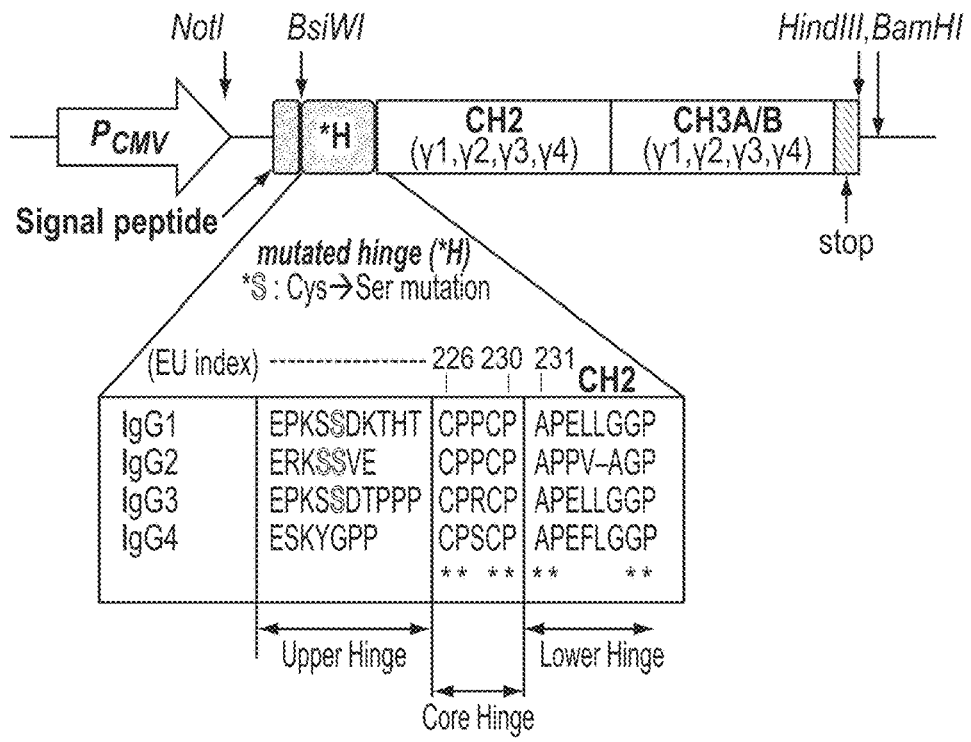
FIG. 5 is a schematic view of a vector for expressing a heterodimeric Fc for each isotype, constructed by sequence and structure analysis, in animal cells. The heterodimeric Fc variant for each isotype, which comprises a mutated hinge region, was cloned into the vector by use of restriction enzymes (NotI/HindIII).

Construction of A107 Heterodimeric Fc Isotype Variants for Each Human Immunoglobulin Isotype The A107 heterodimeric Fc isotype variants designed through the sequencing in Example 1 and the structural modeling in Example 2 were cloned in-frame into the animal cell expression vector pcDNA3.1(+)(Invitrogen, USA) to have signal sequence-hinge-CH2-CH3 using NotI/HindIII restriction enzymes and synthetic oligonucleotides (Macrogen, Korea) by a site-directed mutagenesis method which is performed by those skilled in the art (see FIG. 5).

In the hinge domain used, the cysteine residues in the upper hinge region, other than the cysteine residues in the core hinge region for heterodimer formation, were substituted with serine residues in order to prevent disulfide bonds from being produced during protein fusion. In particular, for IgG3, it was found in the literature that the high antibody effector functions (ADCC and CDC) of IgG3 are maintained even by only the C-terminal 15 amino acids of the core hinge domain among the 47 amino acids of the hinge domain of the G3m(s,t) allotype (Dall'Acqua W F et al., 2006). Accordingly, only the C-terminal 15 amino acids of the sequence shown in FIG. 5 were used.

Table 2 below shows the amino acid sequence information of the CH3 regions in the wild-type and A107 heterodimeric Fc variant pairs of the present invention.

TABLE 2

| configuration | CH3A chain (CH3 sequence of first Fc region) (EU number 341 to 447) | CH3B chain (CH3 sequence of second Fc region) (EU number 341 to 447) |
|---|---|---|
| IgG1 Wild type | GQPREPQVYTLPPSRDELTKN QVSLTCLVKGFYPSDIAVEWE SNGQPENNYKTTPPVLDSDGS FFLYSKLTVDKSRWQQGNVFS CSVMHEALHNHYTQKSLSLSP GK (SEQ ID NO: 7) | Same as SEQ ID NO: 7 |
| γ1-A107 | GQPREPQVYTLPPSRDELTKN QVSLTCLVEGFYPSDIAVEWE SNGQPENNYKTTPPVLDSDGS FFLYSWLTVDKSRWQQGNVFS CSVMHEALHNHYTQKSLSLSP GK (SEQ ID NO: 8) | GQPREPQVYTLPPSRDNLTKN QVSLTCLVKGFYPSDIAVEWE SNGQPENNYKTTPPVLVSDGS FTLYSKLTVDKSRWQQGNVFS CSVMHEALHNHYTQKSLSLSP GK (SEQ ID NO: 9) |
| IgG2 Wild type | GQPREPQVYTLPPSREEMTKN QVSLTCLVKGFYPSDIAVEWE SNGQPENNYKTTPPMLDSDGS FFLYSKLTVDKSRWQQGNVFS CSVMHEALHNHYTQKSLSLSP GK (SEQ ID NO: 10) | Same as SEQ ID NO: 10 |
| γ2-A107 | GQPREPQVYTLPPSREEMTKN QVSLTCLVEGFYPSDIAVEWE SNGQPENNYKTTPPMLDSDGS FFLYSWLTVDKSRWQQGNVFS CSVMHEALHNHYTQKSLSLSP GK (SEQ ID NO: 11) | GQPREPQVYTLPPSRENMTKN QVSLTCLVKGFYPSDIAVEWE SNGQPENNYKTTPPMLVSDGS FTLYSKLTVDKSRWQQGNVFS CSVMHEALHNHYTQKSLSLSP GK (SEQ ID NO: 12) |
| IgG3 Wild type | GQPREPQVYTLPPSREEMTKN QVSLTCLVKGFYPSDIAMEWE SSGQPENNYKTTPPVLDSDGS FFLYSKLTVDKSRWQQGNIFS CSVMHEALHNHYTQKSLSLSP GK (SEQ ID NO: 13) | Same as SEQ ID NO: 13 |
| γ3-A107 | GQPREPQVYTLPPSREEMTKN QVSLTCLVEGFYPSDIAMEWE SSGQPENNYKTTPPVLDSDGS FFLYSWLTVDKSRWQQGNIFS CSVMHEALHNHYTQKSLSLSP GK (SEQ ID NO: 14) | GQPREPQVYTLPPSRENMTKN QVSLTCLVKGFYPSDIAMEWE SSGQPENNYKTTPPVLVSDGS FTLYSKLTVDKSRWQQGNIFS CSVMHEALHNHYTQKSLSLSP GK (SEQ ID NO: 15) |
| IgG4 Wild type | GQPREPQVYTLPPSQEEMTKN QVSLTCLVKGFYPSDIAVEWE SNGQPENNYKTTPPVLDSDGS FFLYSRLTVDKSRWQEGNVFS CSVMHEALHNHYTQKSLSLSL GK (SEQ ID NO: 16) | Same as SEQ ID NO: 16 |

TABLE 2-continued

| con-figur-ation | CH3A chain (CH3 sequence of first Fc region) (EU number 341 to 447) | CH3B chain (CH3 sequence of second Fc region) (EU number 341 to 447) |
|---|---|---|
| γ4-A107 | GQPREPQVYTLPPSQEEMTKN QVSLTCLVEGFYPSDIAVEWE SNGQPENNYKTTPPVLDSDGS FFLYSWLTVDKSRWQEGNVFS CSVMHEALHNHYTQKSLSLSL GK (SEQ ID NO: 5) | GQPREPQVYTLPPSQENMTKN QVSLTCLVKGFYPSDIAVEWE SNGQPENNYKTTPPVLSDGS FTLYSRLTVDKSRWQEGNVFS CSVMHEALHNHYTQKSLSLSL GK (SEQ ID NO: 6) |

Example 4

Figure 6:
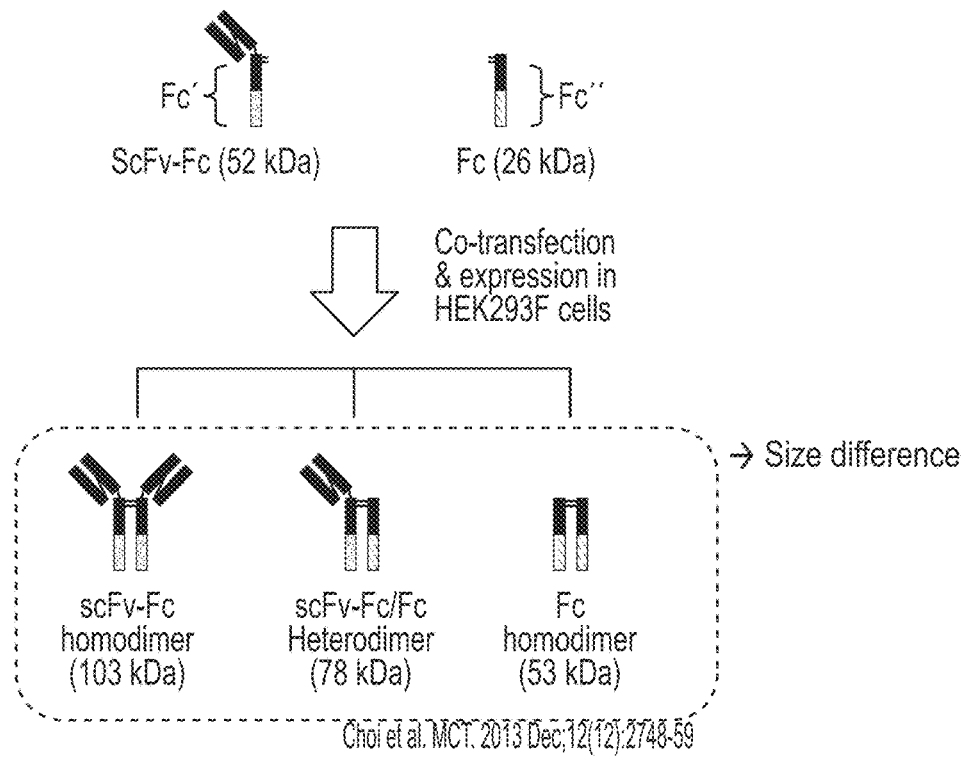
FIG. 6 schematically shows a scFv-Fc$_{CS3A}$/Fc$_{CH3B}$ expression system for evaluating the ability of heterodimeric Fc variants to form a heterodimer, by the dimer size difference between expressed proteins.

Evaluation of the Heterodimerization Ability of A107 Heterodimeric Fc Variants for Each Human Immunoglobulin Isotype In order to examine whether the A107 heterodimeric Fc isotype variants constructed in Example 3 actually have heterodimerization ability similar to those of wild-type A107 variants, a scFv-Fc$_{CH3A}$/Fc$_{CH3B}$ expression system which is mainly used to evaluate heterodimerization ability of Fc variants in the same kind of studies was used (Choi et al., 2013). FIG. 6 is a schematic view showing the scFv-Fc$_{CH3A}$/Fc$_{CH3B}$ expression system. Since antibodies purified in the scFv-Fc$_{CH3A}$/Fc$_{CH3B}$ expression system show molecular weights different between an scFv-Fc$_{CH3A}$ homodimer (103 kDa), an scFv-Fc$_{CH3A}$/Fc$_{CH3B}$ heterodimer (78 kDa) and an Fc$_{CH3B}$ homodimer (53 kDa), the degree of formation of the heterodimer can be compared on SDS-PAGE.

Figure 7:
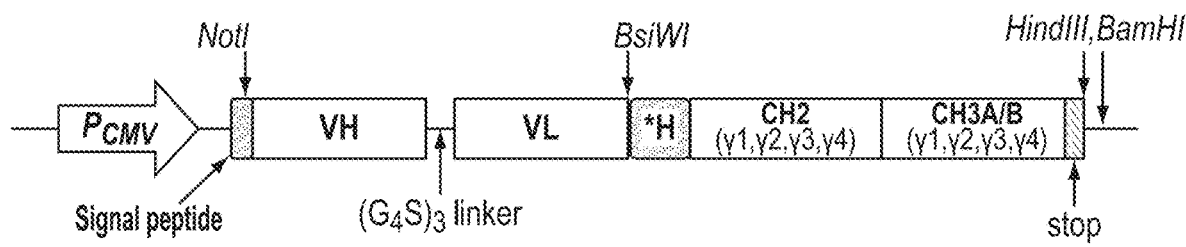
FIG. 7 is a schematic view for cloning scFv-Fc fused to a single-chain variable fragment (scFv), constructed to evaluate the heterodimerization formation yield of an antibody Fc by a CH3 mutant pairs as shown in FIG. 6, into a pcDNA3.1 vector which is an animal cell expression vector.

As the Fc$_{CH3B}$ vector, the vector constructed in Example 3 was used. Additionally, a vector was cloned by introducing scFv only into the N-terminus of Fc$_{CH3A}$, that is, providing a format of pcDNA3.1(+)-scFv-hinge-CH2-CH3A (scFv-Fc$_{CH3A}$). FIG. 7 is a schematic view of the animal cell expression vector pcDNA3.1(+)-scFv-hinge-CH2-CH3A (scFv-Fc$_{CH3A}$) used in the scFv-Fc$_{CH3A}$/Fc$_{CH3B}$ expression system. The scFv antibody used is an antibody obtained by linking the VH and VL regions of hAY4a which is an affinity-enhanced version of the humanized antibody hAY4 that binds specifically to DR4 (Lee, Park et al. 2010). Cloning was performed using NotI restriction enzyme and the BsiWI restriction enzyme located immediately before the hinge domain. As a control for the variant, wild-type Fc was constructed in the same format (scFv-Fc/Fc).

Example 5

Expression and Purification of Antibodies Comprising A107 Heterodimeric Fc Variants for Each Human Immunoglobulin Isotype Co-expression of the constructed scFv-Fc$_{CH3A}$ and Fc$_{CH3B}$ was performed by transiently transfecting a mixture of expression vectors (1:1 ratio) and polyethylenimine (PEI) (Polyscience) into HEK293-F cells (Invitrogen) and culturing the cells in a shake flask containing serum-free FreeStyle 293 expression medium. The detailed method is as follows.

For 200 mL transfection in a shake flask (Corning), HEK293-F cells were seeded into 100 ml of medium at a density of 2.0×10⁶ cells/ml, and cultured at 150 rpm under 8% CO$_2$. To produce each humanized antibody, heavy chain and light-chain plasmids for each antibody were diluted in 10 ml of FreeStyle 293 expression medium (Invitrogen) in a total amount of 250m (2.5 μg/ml) (125 μg for the light chain and 125 μg for the heavy chain), and the medium was mixed with 10 ml of medium (7.5m/ml) containing 750 m of PEI diluted therein. The medium mixture was incubated at room temperature for 10 minutes. Next, the incubated medium mixture was added to 100 ml of the seeded cells and incubated for 4 hours at 150 rpm under 8% CO$_2$, after which the remaining 100 ml of FreeStyle 293 expression medium was added thereto, followed by incubation for 5 to 7 days. During this incubation, the protein produced by the cells, that is, an antibody comprising the Fc variant, was secreted out of the cells and accumulated in the medium. For this reason, the protein was purified using the protein A Sepharose column (GE Healthcare) from the cell culture supernatant collected by 20 minutes of centrifugation at 2500 rpm after cell culturing. In this case, the purification process was performed with reference to the standard protocol provided by the protein A column company. The purified protein was quantified by measuring the absorbance at a wavelength of 562 nm using the solution in the BCA protein assay kit (Thermo) and determining the amount thereof according to the prepared standard curve.

Example 6

Figure 8:
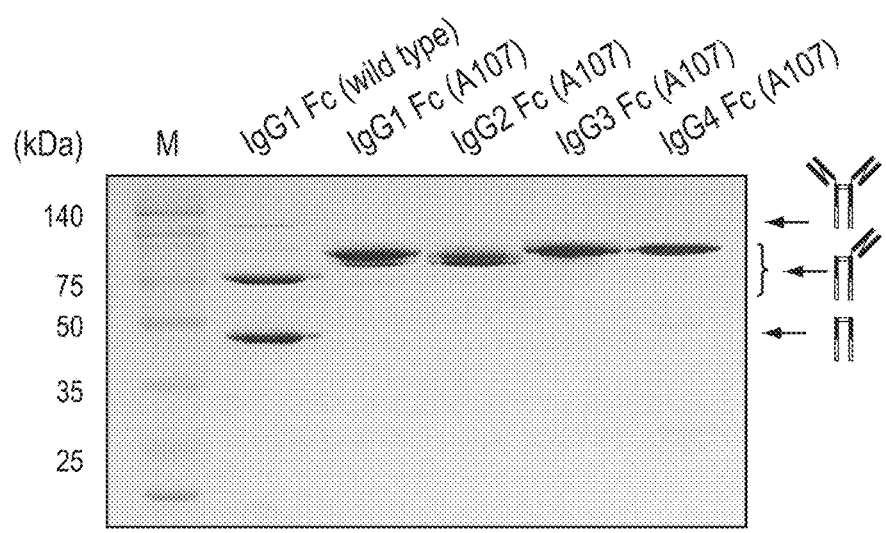
FIG. 8 shows the results of co-transfecting CH3 mutant pairs-introduced animal cell expression vectors, constructed according to the expression systems shown in FIGS. 5 and 7, into HEK293F cells in order to evaluate the heterodimerization formation as shown in FIG. 6, transiently expressing and purifying the vectors, and then separating 5 µg of protein on SDS-PAGE under non-reducing conditions in order to evaluate the heterodimerization formation, and analyzing the protein according to size and combination by Coomassie blue staining. As a negative control, a wild-type Fc with wild-type CH3 was used.

Evaluation of the Heterodimerization Ability of A107 Heterodimeric Fc Variants for Each Human Immunoglobulin Isotype 5 μg of the antibody, purified in Example 5 and comprising the A107 heterodimeric Fc variant for each isotype, was analyzed on 12% SDS-PAGE under non-reducing conditions (FIG. 8). A homodimer of the CH3A variant was observed at 103 kD; a homodimer of the CH3B variant was observed at 53kD; a monomer of the CH3B variant was observed at 25 kD; and a heterodimer of the CH3A variant and the CH3B variant was observed at 78 kD. To more accurately examine the degree of homodimerization, Western blotting was also performed. Western blotting was performed by isolating 0.1 μg of protein, which was smaller than that in 12% SDS-PAGE analysis, under non-reducing conditions, and then treating the protein with anti-human IgG-AP conjugated antibody (Sigma) according to a conventional method known in the art (FIG. 9).

Figure 9:
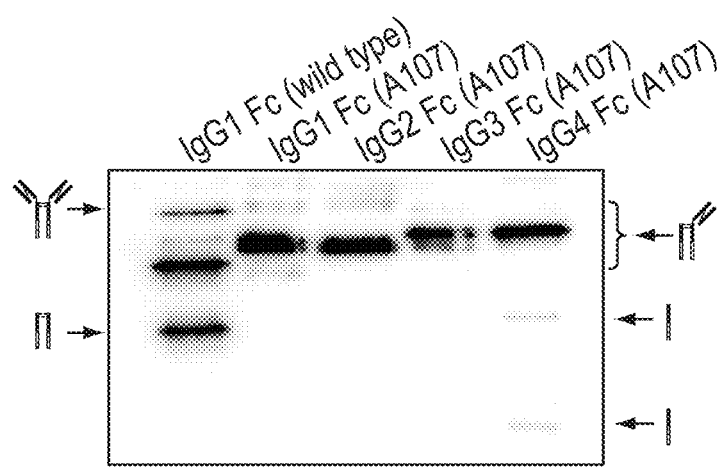
FIG. 9 shows the results of separating protein by SDS-PAGE according to the method shown in FIG. 8, and then performing Western blotting using anti-human IgG-AP conjugated antibody.

As can be seen in FIGS. 8 and 9, for the IgG1 heterodimers introduced with the wild-type CH3 domain which is a control, a homodimer of each of CH3A and CH3B and a CH3A:CH3B heterodimer were all observed on SDS-PAGE, whereas the A107 heterodimeric Fc variants for each human immunoglobulin isotype, obtained by introducing the A107 heterodimerization mutation into IgG2, IgG3 and IgG4, except for IgG1, all formed heterodimers in yields similar to or higher than those of previously reported IgG1-based A107 variants. At this time, for the IgG4 variant, an Fc monomer (half Fc) comprising CH3A or CH3B was also observed, which is one of the properties of naturally occurring IgG4 and results from the property of forming half Fc with respect to the hinge domain (particularly, serine at position 228 in the core hinge region) before the occurrence of Fab-arm exchange in blood (Liu H et al., 2012).

Example 7

Construction of Human/Mouse IL-12 Fusion Protein

The isotype variants in Examples 1 to 6 were found to retain their heterodimerization ability at a level similar to that of the previously reported IgG1-based A107 heterodimeric Fc variant. Among these isotype variants, the IgG4-based variant (γ4-A107) was used to construct a long-lasting IL-12 fusion protein. Naturally occurring IL-12 is composed of two subunits, a p35 subunit (p35; IL-12A) and a p40 subunit (p40; IL-12B), and the two subunits interact to form a heterodimer having activity. Formation of this heterodimer is achieved because the two subunits are more strongly and stably coupled by a single disulfide bond present between the two subunits. Accordingly, the two subunits (p35 and p40) of IL12 were genetically fused to the N-terminus of each heterodimeric Fc chain in order to maintain the heterodimeric form of the naturally occurring cytokine.

As a heterodimeric Fc variant for construction of a fusion protein, γ4-A107 was used, which was based on IgG4 and would form a heterodimer by introduction of the A107 mutation. As previously reported, in construction of an immunocytokine which is a fusion of an antibody and a cytokine, the antibody effector function (such as ADCC/CDC) of IgG1 rather promotes in vivo clearance. For this reason, a fusion protein was constructed using an IgG4 isotype which hardly shows the ADCC/CDC function, compared to IgG1 (Gillies S D et al., 1999).

Figure 11A:
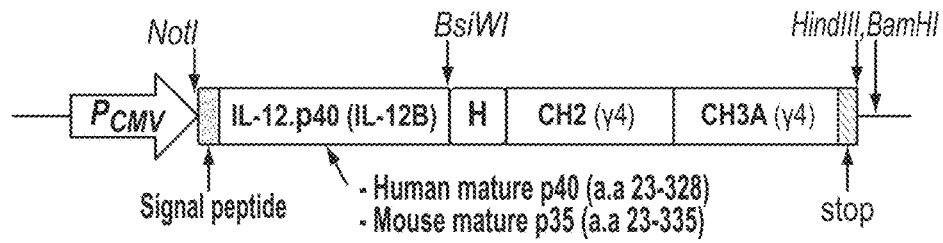
FIG. 11A shows a schematic view of a vector for expressing and purifying an IL-12 p40 fusion protein of an example of the present invention (FIG. 10C) in animal cells.
Figure 11B:
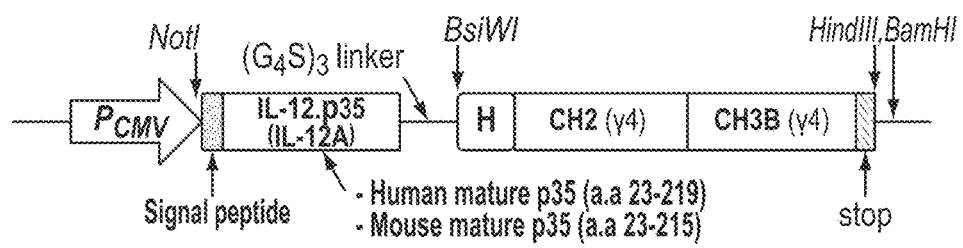
FIG. 11B shows a schematic view of a vector for expressing and purifying an IL-12 p35 fusion protein of an example of the present invention (FIG. 10C) in animal cells.
Figure 12:
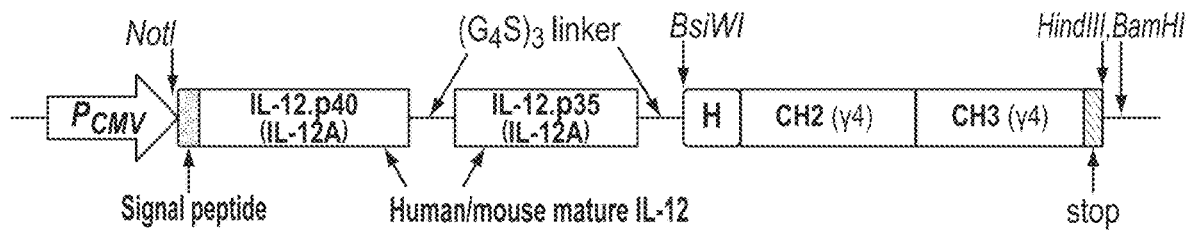
FIG. 12 is a schematic view of a vector for expressing and purifying a fusion protein of an example of the present invention (FIG. 10B) in animal cells.

FIGS. 10A-10C show schematic views of an IL-12 recombinant protein (FIG. 10A), a monovalent IL-12 fusion protein (mono-IL-12-Fc) obtained using γ4-A107 (FIG. 10C), and a bivalent IL-12 fusion protein (bi-IL-12-Fc) obtained using wild-type Fc (FIG. 10B) in the present invention. In particular, FIG. 10C shows a fusion protein constructed by introducing the CH3 variant pair in the present invention. The DNA sequence of each of human IL-12 (hIL-12, Uniprot entry name P29460, P29459; SEQ ID NO: 17-18) and mouse IL-12 (mIL-12, Uniprot entry name P43432, P43431; SEQ ID NO: 19-20), which encodes a mature form excluding a signal sequence, was amplified, and each amplification product was cloned in-frame into an animal cell expression vector containing the γ4-A107 variant by use of NotI/B siWI restriction enzymes as shown in FIGS. 11A and 11B. The resulting proteins were named mono-hIL-12-Fc and mono-mIL-12-Fc, respectively. In particular, a flexible peptide linker consisting of 15 amino acids was added between the p35 subunit and the hinge domain so that the human/mouse p35 subunit could sufficiently interact with the p40 subunit (flexible $(G_4S)_3$ Linker). As comparative examples for the protein shown in FIG. 10C, bi-hIL-12-Fc and bi-mIL-12-Fc were constructed by fusing each of human IL-12 (hIL-12) and mouse IL-12 (mIL-12) to wild-type IgG4 Fc (wt IgG4). In order to fuse a single Fc with IL-12 which have activity only in a heterodimeric form, the two subunits of IL-12 were linked to each other by the 15-amino-acid peptide linker, and then cloned in-frame into an animal cell expression vector containing the γ4-A107 variant by use of NotI/BsiWI restriction enzymes as shown in FIG. 12. The comparative examples are fusion proteins used in previous studies to make IL-12 fusion proteins (Lisan S. Peng et al., 1999).

Table 3 below shows the amino acid sequences for a mature form of the subunits of the human and mouse IL-12 used for construction of the fusion proteins.

TABLE 3

| configuration | CH3A chain (p40 subunit) | CH3B chain (p35 subunit) |
|---|---|---|
| Mature human IL-12 | IWELKKDVYVVELDWYPDA PGEMVVLTCDTPEEDGITW TLDQSSEVLGSGKTLTIRV KEFGDAGQYTCHKGGEVLS HSLLLLHKKEDGIWSTDIL KDQKEPKNKTFLRCEAKNY SGRFTCWWLTTISTDLTFS VKSSRGSSDPQGVTCGAAT LSAERVRGDNKEYEYSVEC QEDSACPAAEESLPIEVMV DAVHKLKYENYTSSFFIRD IIKPDPPKNLQLKPLKNSR QVEVSWEYPDTWSTPHSYF SLTFCVQVQGKSKREKKDR VFTDKTSATVICRKNASIS VRAQDRYYSSSWSEWASVP CS (SEQ ID NO: 17) | RNLPVATPDPGMFPCLHHSQN LLRAVSNMLQKARQTLEFYPC TSEEIDHVDITKDKTSTVEAC LPLELTKNESCLNSRETSFIT NGSCLASRKTSFMMALCLSSI YEDLKMYQVEFKTMNAKLLMD PKRQIFLDQNMLAVIDELMQA LNFNSETVPQKSSLEEPDFYK TKIKLCILLHAFRIRAVTIDR VMSYLNAS (SEQ ID NO: 18) |
| Mature mouse IL-12 | MWELEKDVYVVEVDWTPDA PGETVNLTCDTPEEDDITW TSDQRHGVIGSGKTLTITV KEFLDAGQYTCHKGGETLS HSHLLLHKKENGIWSTEIL KNFKNKTFLKCEAPNYSGR FTCSWLVQRNMDLKFNIKS SSSPPPDSRAVTCGMASLSA EKVTLDQRDYEKYSVSCQE DVTCPTAEETLPIELALEA RQQNKYENYSTSFFIRDII KPDPPKNLQMKPLKNSQVE VSWEYPDSWSTPHSYFSLK FFVRIQRKKEKMKETKEGC NQKGAFLVEKTSTEVQCKG GNVCVQAQDRYYNSSCSKW ACVPCRVRS (SEQ ID NO: 19) | RVIPVSGPARCLSQSRNLLKTTD DMVKTAREKLKHYSCTAEDIDHE DITRDQTSTLKTCLPLELHKNES CLATRETSSTTRGSCLPPQKTSL MMTLCLGSIYEDLKMYQTEFQAI NAALQNHNHQQIILDKGMLVAID ELMQSLNHNGETLRQKPPVGEAD PYRVKMKLCILLHAFSTRVVTIN RVMGYLSSA (SEQ ID NO: 20) |

Example 8

Expression/Purification of IL-12 Fusion Protein

The mono-IL-12-Fc fusion protein in FIG. 10C was expressed/purified from the human/mouse IL-12.p40-γ4-A107A and human/mouse IL-12.p35-γ4-A107B expression vectors (1:1 ratio) according to the method described in Example 5. The bi-IL-12-Fc fusion protein in FIG. 10B was expressed/purified through single transfection of the human/mouse scIL-12-IgG4 Fc(wt) expression vector. All the fusion proteins were expressed/purified in an amount of 12 to 13 mg per 100 ml of the HEK293F cell culture.

Figure 13:
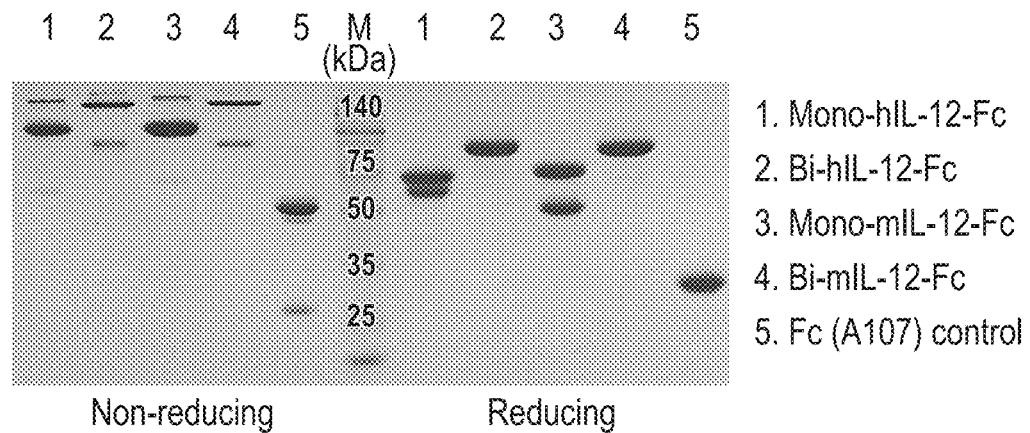
FIG. 13 shows the results of co-transfecting the animal cell expression vectors of FIGS. 11A and 11B, constructed using human and mouse interleukin genes, into HEK293F cells, transiently expressing and purifying the genes, and then separating 5 µg of protein on SDS-PAGE under non-reducing conditions, and analyzing the protein according to size and combination by Coomassie blue staining.

5 μg of each of the purified mono-IL-12-Fc and bi-IL-12-Fc fusion proteins was analyzed on 12% SDS-PAGE under non-reducing conditions (FIG. 13). A monomer of the IL-12.p40-CH3A variant was observed at 60 kD; a homodimer of the IL-12.p40-CH3A variant was observed at 120 kD; a monomer of the IL-12.p35-CH3B variant was observed at 50 kD; a homodimer of the IL-12.p35-CH3B variant was observed at 100 kD; and a heterodimer of the IL-12.p40-CH3A variant and the IL-12.p35-CH3B variant was observed at 110 kD. However, for the proteins obtained by linking the human and mouse interleukin subunits, bands were observed at slightly different sizes, and it was found in the literature that these bands result from different glycosylation patterns (Lo et al., 2007). In addition, in the same manner as described in Example 6 above, a monomer was observed in all the IL-12 fusion proteins based on IgG4. Similar to the previous report that the p35 subunit is not naturally expressed in a monomeric form without the aid of the p40 subunit, only a p40 subunit-linked CH3A monomer was observed in the mono-IL-12-Fc fusion protein obtained using the heterodimeric Fc variant (Gillies et al., 1998b).

Figure 14:
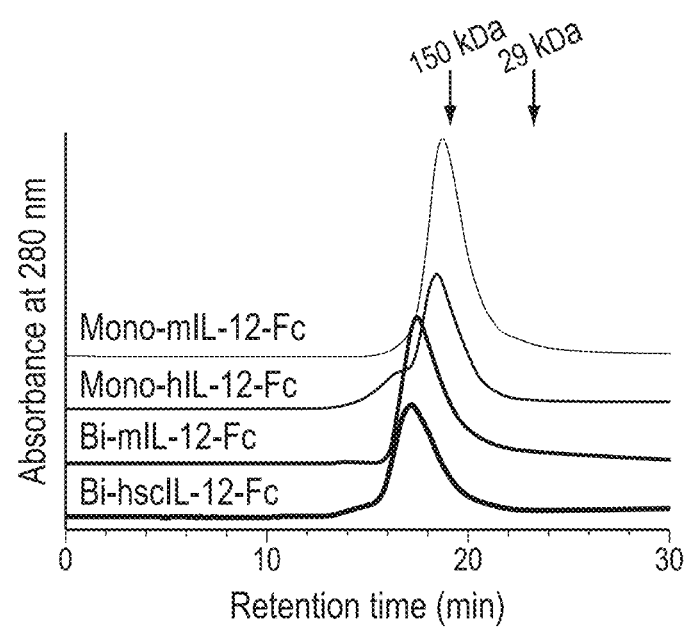
FIG. 14 shows the results of analyzing the fusion proteins of FIG. 13 by size-exclusion chromatography (SEC).

FIG. 14 shows the results of analyzing the fusion proteins by size-exclusion chromatography (SEC). An oligomer was partially observed from the Mono-hIL-12-Fc fusion protein.

Example 9

Evaluation of the Binding Affinity of Mono-hIL-12-Fc Fusion Protein for IL-12 Receptor The binding affinity of the mono-hIL-12-Fc, expressed and purified in Example 8, for the IL-12 receptor, was analyzed comparatively with that of bi-hIL-12-Fc.

FIG. 15A and FIG. 15B show the results of FACS-Calibur (BD Biosciences) analysis performed to determine that the constructed mono-hIL-12-Fc would show binding affinity for the IL-12 receptor, in comparison with bi-hIL-12-Fc.

Specifically, in order to isolate immune cells (PBMCs) from human peripheral blood, 5 ml of Ficoll (GE Healthcare) was filled in a 15-ml test tube. Sampled blood was mixed with PBS (pH 7.4) at 1:1 and shaken, and then 10 ml of the blood was taken and centrifuged in the Ficoll-containing test tube in a "no break" state at 750 g for 20 minutes so as not to mix with Ficoll. Next, the buffy coat formed on the Ficoll was recovered and washed twice with PBS (pH 7.4), and then PBMCs, including T cells, B cells, NK cells and monocytes, were obtained. The isolated normal PBMCs did not express IL-12R in such large amounts that the binding of IL-12 could be observed (FIG. 15A). For this reason, the cells were stimulated by treatment with the mitogen PHA (Sigma-Aldrich) for 72 hours so that T cells and NK cells could be activated. It was reported that when cells are treated with PHA, the IL-12 receptor is expressed in T cells and NK cells while immune cells divide. PBMCs were added to 10% FBS-containing RPMI1640 medium at a density of $1\times10^6$ cells/ml, and the mitogen PHA was added thereto at a concentration of 10 µg/ml, after which the cells were cultured in a 5% $CO_2$ incubator at 37° C. for 72 hours. Normal PBMCs and PHA-activated PBMCs were washed with cold PBS (pH 7.4), and $5\times10^5$ cells per sample were prepared. Each of Fc (A107), bi-hIL-12-Fc and mono-hIL-12-Fc was added to each sample at a concentration of 1 µM, incubated at 4° C. for 30 minutes, and then washed with cold PBS (pH 7.4). Each sample was incubated with FITC-conjugated human anti-IgG4 secondary antibody (Sigma-Aldrich) at 4° C. for 30 minutes, washed with PBS (pH 7.4), and then analyzed by flow cytometry (FACS Calibur, BD Bioscience). After analysis, a histogram graph for each sample was obtained, and the binding affinity of mono-hIL-12-Fc for the IL-12 receptor was evaluated.

The results of the analysis indicated that bi-hIL-12-Fc and mono-hIL-12-Fc did not bind to normal PBMCs expressing no IL-12 receptor (FIG. 15A) and did bind only to PHA-activated PBMCs expressing the IL-12 receptor (FIG. 15B). Thus, it was found that the binding affinity of mono-hIL-12-Fc for the IL-12 receptor was equal to that of bi-hIL-12-Fc.

Example 10

Evaluation of the Ability of Mono-hIL-12-Fc Fusion Protein to Induce PBMC Proliferation Whether the IL-12 moiety in the IL-12 fusion protein would retain physiological activity comparable to that actual recombinant IL-12 (rIL-12) by its binding to the IL-12 receptor was examined using recombinant human IL-12 (rhIL-12, Thermo Fisher Scientific) as a control.

FIGS. 16(A)-16(D) show the results of a WST-1 cell proliferation assay performed to examine the cell proliferation abilities of Fc (A107), rhIL-12, bi-hIL-12-Fc and mono-hIL-12-Fc in PHA-activated PBMCs.

Specifically, PBMCs ($2\times10^4$ cells, 50 µl) activated by PHA in the same manner as described in Example 9 were added to a 96-well plate (SPL, Korea), followed by addition of 50 µl of each of 50-0.4 pM Fc (A107), rhIL-12, bi-hIL-12-Fc and mono-hIL-12-Fc diluted serially with 10% FBS-containing RPMI1640 medium. Next, the cells were cultured at 37° C. under 5% $CO_2$ for 72 hours. For a cell proliferation assay, 10 µl of WST-1 (Water-soluble Tetrazolium salts, Sigma-aldrich) reagent was then added to each well and incubated at 37° C. for 4 hours, and the absorbance at 570 nm was measured using a microplate reader (Molecular Devices).

As a result, it was shown that mono-hIL-12-Fc had a PBMC proliferation ability similar to or higher than that of rhIL-12.

Example 11

Evaluation of the Ability of Mono-hIL-12-Fc Fusion Protein to Induce IFN-y Secretion from PBMCs FIGS. 17(A)-17(D) show the results of an ELISA performed to measure the amount of IFN-γ secreted from PHA-activated PBMCs by Fc (A107), rhIL-12, bi-hIL-12-Fc and mono-hIL-12-Fc.

Specifically, in order to measure the concentration of IFN-γ in the culture supernatant cultured for 72 hours in Example 10, a 96-well plate (Thermo Fisher Scientific, Korea) for ELISA was coated with human IFN-γ capture antibody (Thermo Fisher Scientific) for 12 hours, washed with PBST, and then blocked with 1% BSA (PBS with 1% bovine serum albumin) at room temperature for 1 hour. After washing with PBST (PBS with 0.1% Tween-20), the culture supernatant obtained in Example 2 was diluted 5-fold with 1% BSA, and 100 µl of the dilution was added to each well and incubated at room temperature for 2 hour. After washing with PBST, each well was incubated with biotin-conjugated IFN-γ detection antibody (Thermo Fisher Scientific) at room temperature for 1 hour. After washing with PBST (PBS with 0.1% Tween-20), each well was incubated with avidin-conjugated horse radish peroxidase (HRP) (Thermo Fisher Scientific) at room temperature for 30 minutes, washed with PBST (PBS with 0.1% Tween-20), and then treated with 3,3',5,5'-tetramethylbenzidine substrate (TMB, sigma-aldrich). The absorbance at 405 nm was measured using a microplate reader.

As a result, it was shown that the ability of mono-hIL-12-Fc to induce IFN-y secretion from PBMCs was similar to or higher than that of rhIL-12.

Example 12

Evaluation of the Binding Affinity of Mono-mIL-12-Fc for IL-12 Receptor

The binding affinity of mono-mIL-12-Fc, expressed/purified in Example 8, for the IL-12 receptor, was analyzed comparatively with that of bi-mIL-12-Fc.

FIGS. 18(A) and 18(B) show the results of flow cytometry performed to determine that the constructed mono-mIL-12-Fc shows a binding affinity for the IL-12 receptor, in comparison with bi-mIL-12-Fc.

Specifically, it was reported that mouse IL-12 binds not only to the mouse IL-12 receptor, but also to the human IL-12 receptor. Thus, analysis was performed in the same manner as described in Example 9. The results of the analysis indicated that bi-mIL-12-Fc and mono-mIL-12-Fc did not bind to normal PBMCs expressing no IL-12 receptor (FIG. 18A) and did bind only to PHA-activated PBMCs expressing the IL-12 receptor (FIG. 18B). Thus, it was shown that the binding affinity of mono-mIL-12-Fc for the IL-12 receptor was the same as that of bi-mIL-12-Fc.

Example 13

Evaluation of the Ability of Mono-mIL-12-Fc to Induce PBMC Proliferation

Figures 19A, 19B:
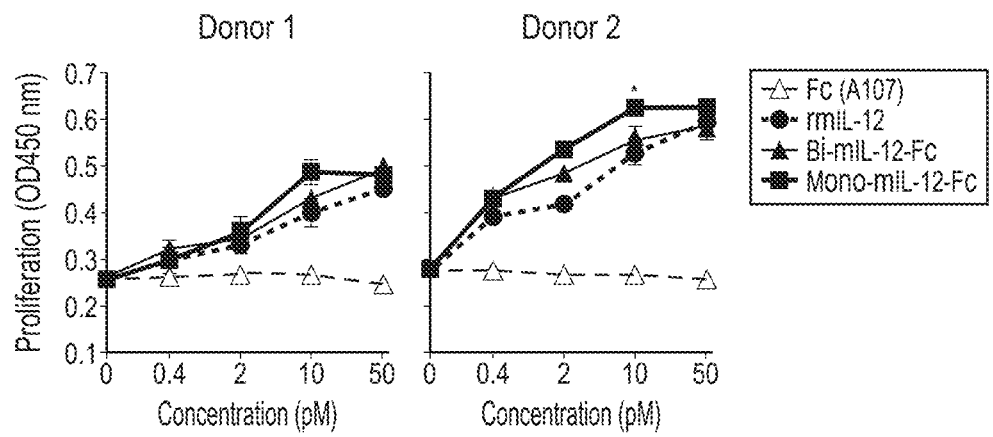
FIGS. 19A and 19B show the results of a WST-1 cell proliferation assay performed using cells from donor 1 (FIG. 19A) or donor 2 (FIG. 19B) to measure the effect of various concentrations of Fc (A107), recombinant mouse IL-12 (rmIL-12), bi-mIL-12-Fc and mono-mIL-12-Fc on the proliferation of PHA-activated PBMCs in which the IL-12 receptor was induced by treatment with the mitogen PHA.

FIGS. 19(A) and 19(B) show the results of a WST-1 cell proliferation assay performed to examine effects of abilities of Fc (A107), recombinant mouse IL-12(rmIL-12), bi-mIL-12-Fc, and mono-mIL-12-Fc on the cell proliferation of PHA-activated PBMCs.

Specifically, PBMCs ($2 \times 10^4$ cells, 50 µl) activated by PHA in the same manner as described in Example 9 were added to a 96-well plate, followed by addition of 50 µl of each of 50-0.4 pM Fc (A107), rmIL-12, bi-mIL-12-Fc and mono-mIL-12-Fc diluted serially with 10% FBS-containing RPMI1640 medium. Next, the cells were cultured at 37° C. under 5% $CO_2$ for 72 hours, and then a WST assay was performed in the same manner as described in Example 10. As a result, it was shown that mono-mIL-12-Fc had the ability to induce PBMC proliferation, similar to rmIL-12.

Example 14

Evaluation of the Ability of Mono-mIL-12-Fc to Inhibit In Vivo Tumor Growth

In Example 13, the ability of mono-mIL-12-Fc to induce the proliferation of PHA-activated PBMCs was evaluated. Whether the same effect of mono-mIL-12-Fc would also appear in vivo was examined.

Figures 20A, 20B:
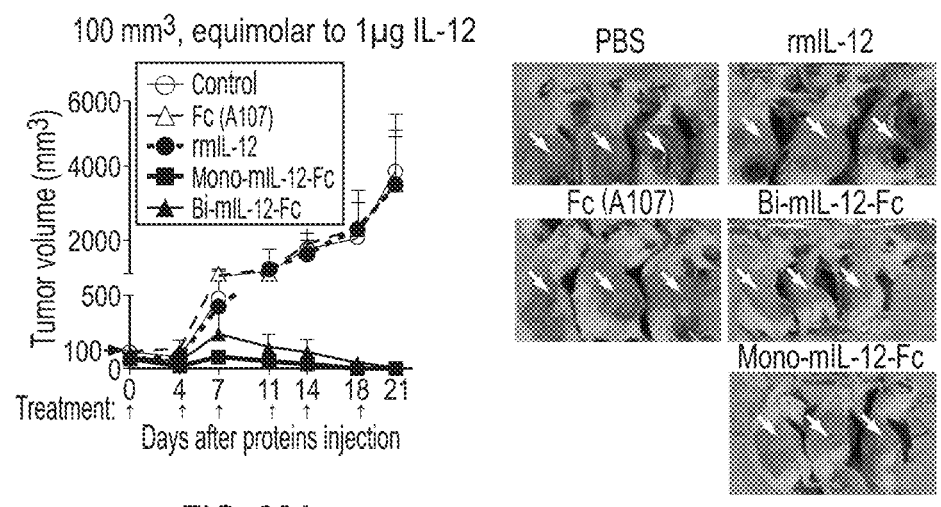
FIG. 20A is a graph showing the changes of tumor volume in Balb/c mice transplanted with CT26$^{HER2}$/Neu tumors during the intraperitoneal administration of Fc (A107), rmIL-12, bi-mIL-12-Fc and mono-mIL-12-Fc.
FIG. 20B shows pictures of the tumor-bearing mice after sacrifice at the end of administration. Injection of mIL12-Fc proteins was initiated 11 days after tumor cell inoculation when the tumor volume reached 100 mm3.

FIGS. 20A-20C show the results of measuring the tumor growth inhibitory activity of mono-mIL-12-Fc on 100 mm³ tumors in living mice.

Specifically, 4-week-old female Balb/c mice (NARA Biotech, Korea) were shaved, and CT26$^{HERS/Neu}$ colorectal cancer cells ($1 \times 10^6$ cells/mouse) diluted in 150 µL of PBS were transplanted subcutaneously into the mice. Mice having similar tumor volumes (average volume: 100 to 120 mm³) were randomly grouped, and each of Fc (A107), rmIL-12 (Thermo Fisher Scientific), bi-mIL-12-Fc and mono-mIL-12-Fc was intraperitoneally injected a total of six times (twice a week) into each mouse at the dose corresponding to an equivalent molar amount of 1 µg IL-12. The tumor was measured twice a week, and the tumor volume (V) was calculated using the following equation: V=length×width²/2.

As shown in FIG. 20A, in comparison with the control, administration of 1 µg of rmIL-12 had no effect on the inhibition of tumor growth, but the equimolar concentrations of mono-mIL-12-Fc and bi-mIL-12-Fc inhibited tumor growth. In addition, as shown in FIG. 20C, administration of mono-mIL-12-Fc and bi-mIL-12-Fc showed little or no changes of mouse body weight compared to the control, indicating that mono-mIL-12-Fc and bi-mIL-12-Fc are not toxic.

Figures 21F, 21G, 21H, 21I, 21J, 21K, 21L:
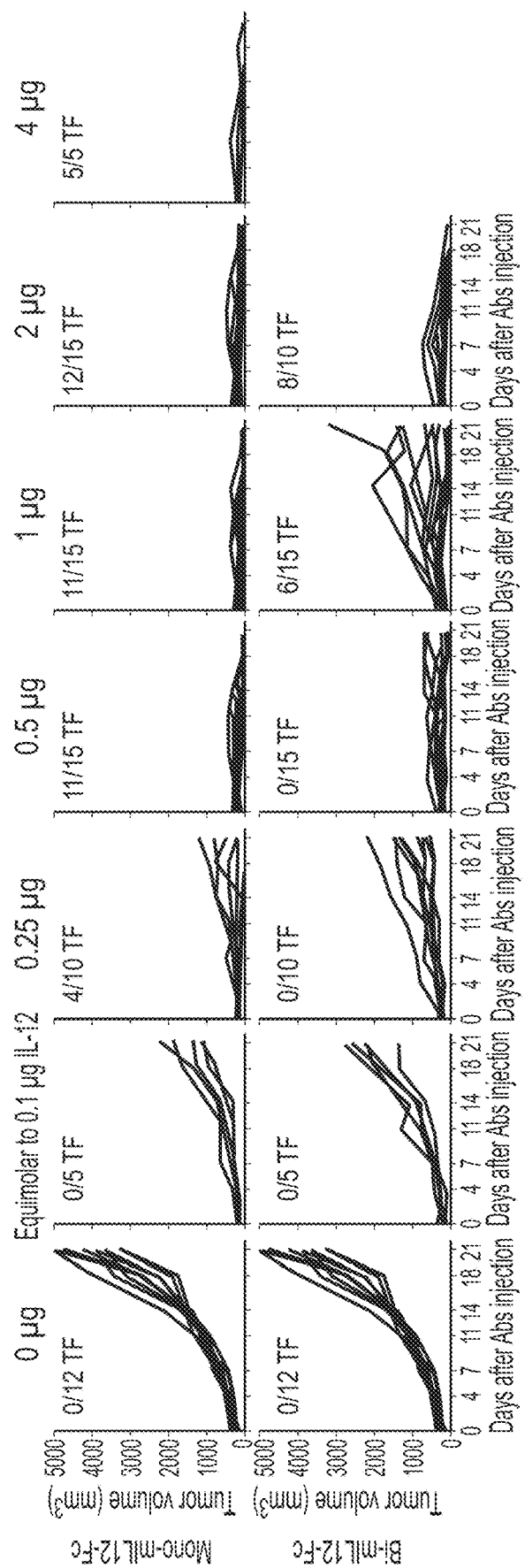
FIG. 21F-21L are graphs showing the changes of individual mouse tumor volume treated with various concentrations (0 μg (FIG. 21F), 0.1 μg (FIG. 21G), 0.25 μg (FIG. 21H), 0.5 μg (FIG. 21I), 1 μg (FIG. 21J), 2 μg (FIG. 21K), or 4 μg (FIG. 21L)) of mIL12-Fc proteins at indicated time points in the experimental procedure shown in FIGS. 21A-21E.

FIGS. 21A-21N show the results of measuring the tumor growth inhibitory activity of various concentrations of mono-mIL-12-Fc on 300 mm³ tumors in living mice.

Specifically, 4-week-old female Balb/c mice (NARA Biotech, Korea) were shaved, and CT26$^{HERS/Neu}$ colorectal cancer cells ($1 \times 10^6$ cells/mouse) diluted in 150 µL of PBS were transplanted subcutaneously into the mice. Mice having similar tumor volumes (average volume: 300 mm³) were randomly grouped, and each of bi-mIL-12-Fc and mono-mIL-12-Fc was intraperitoneally injected a total of 6 times (twice a week) into each mouse at a concentration equimolar to 0.1-2 µg rmIL-12. The tumor was measured twice a week, and the tumor volume (V) was calculated using the following equation: V=length×width²/2.

As shown in FIGS. 21A-21N, at a dose corresponding to an equivalent molar amount of 1 µg IL-12 (FIG. 21D) or less, mono-mIL-12-Fc showed a high effect of inhibiting the growth of large tumors, compared to bi-IL-12-Fc. At a concentration corresponding to an equivalent molar amount of 0.25 µg IL-12 (FIG. 21B), bi-mIL-12-Fc showed the effect of inhibiting tumor growth, but did not remove the tumor. However, under the identical dosing regimen, mono-mIL-12-Fc showed the effect of removing the tumor in 40% of the mice. In addition, at a concentration corresponding to an equivalent molar amount of 0.5 µg IL-12 (FIG. 21C) at which bi-mIL-12-Fc failed to remove the tumor, mono-mIL-12-Fc removed the tumor in 73% of the mice even when it was administered only five times.

Example 15

Evaluation of In Vivo Toxicity of Mono-mIL-12-Fc

FIG. 21O shows the results of measuring body weight changes to determine the in vivo toxicity of mono-mIL-12-Fc administered at various concentrations.

Specifically, as shown in FIGS. 21A-21E, whether the body weight would be reduced was observed by measuring the body weight of mice, administered with mono-mIL-12-Fc, twice a week. It was shown that the body weight increased as the tumor volume increased in the control group, but the mice administered with all concentrations of bi-mIL-12-Fc (FIG. 21P) and mono-mIL-12-Fc (FIG. 21O) showed no decrease in the body weight compared to before administration. Thus, it was determined that mono-mIL-12-Fc does not induce a reduction in body weight, and thus has no significant in vivo toxicity.

FIG. 21Q shows the results of measuring alanine aminotransferase (ALT) that is a hepatotoxicity marker.

Specifically, blood was sampled from the facial veins of the mice of FIGS. 21M-21N at 24 hours after the last administration. The blood was allowed to stand at room temperature for 2 hours so as to induce blood coagulation, and then centrifuged at 8000 rpm for 10 minutes, and the supernatant serum was collected. To measure the concentration of ALT in serum, blood was sampled from the mouse facial veins at 24 hours after the last administration of the IL-12-Fc fusion protein. The blood was allowed to stand at room temperature for 2 hours so as to induce blood coagulation, and then centrifuged at 8000 rpm for 10 minutes, and the supernatant serum was collected. To measure the concentration of ALT in the serum, a substrate solution for ALT measurement (a mixture of alanine and a-ketoglutarate) was taken in a 15-ml test tube and incubated in a constant-temperature water bath at 37° C. for 5 minutes. Serum isolated from the blood of tumor-transplanted mice administered with each of bi-mIL-12-Fc and mono-mIL-12-Fc was diluted 10-fold, and 200 µl of the dilution was added to the substrate solution, shaken, and incubated in a constant-temperature water bath at 37° C. for 30 minutes. 1 ml of a color development reagent (2,4-dinitrophenyl-1-hydrazone) was added to the test tube taken out from the constant-temperature water bath, and the test tube was allowed to stand at room temperature for 20 minutes. Next, 10 ml of 0.4 N sodium hydroxide solution was added to the test tube and mixed, and then the test tube was allowed to stand at room temperature for 10 minutes. The absorbance at 505 nm was measured using a photoelectric spectrophotometer (GeneQuant100, GE Healthcare). Using a standard curve prepared by adding a standard curve reagent instead of serum, ALT was converted into units. It was shown that the serum from the blood sampled from mice administered with Bi-mIL-12-Fc or mono-mIL-12-Fc showed ALT activity similar to that of the serum separated from the blood sample of the control or normal Balb/c mice. This suggests that when bi-mIL-12-Fc or mono-mIL-12-Fc is administered to tumor-transplanted mice at a concentration equimolar to 0.5 µg or 1 µg IL-12, it induces no hepatotoxicity.

Example 16

Evaluation of the Ability of Mono-mIL-12-Fc to Induce Immune Cell Proliferation In Vivo As shown in Example 15, when bi-mIL-12-Fc and mono-mIL-12-Fc were administered at a concentration corresponding to an equivalent molar amount of 2 µg IL-12, bi-mIL-12-Fc and mono-mIL-12-Fc all removed the tumor, but when they were administered at a molar concentration lower than 1 µg IL-12, the tumor growth inhibitory effect of mono-mIL-12-Fc was significantly higher than that of bi-mIL-12-Fc. In fact, analysis was performed to determine whether the high tumor growth inhibitory effect of mono-mIL-12-Fc would be associated with an increase in the number of intrinsic effector cells such as NK cells, CD4$^+$ T cells and CD8$^+$ T cells, which have the IL-12 receptor.

FIGS. 22A-22C show the results of measuring increases in the number of CD4$^+$ T cells (FIG. 22A), CD8$^+$ T cells (FIG. 22B), and NK cells (FIG. 22C) in the spleen of mice sacrificed 3 days after the last administration in FIGS. 21A-21E.

Specifically, after treatment as shown in FIGS. 21A-21E, the mouse spleen was dissected 34 days after tumor transplantation, crushed using a wide mesh in a Petri dish, and then washed with 10 ml of 2% FBS-containing medium. Next, 1 ml of red blood cell lysis buffer was added thereto to lyse red blood cells, and the resulting cells were washed with PBS to prepare a spleen cell suspension, and the number of the cells was countered with a hemocytometer. APC, FITC, PE or PE-cy5-conjugated anti-CD45, anti-CD3, anti-CD4, anti-CD8 and anti-CD49b antibodies were added to the spleen lymphocytes which were then stained at 4° C. for 30 minutes, washed with cold PBS (pH 7.4), and then analyzed by flow cytometry (FACS Calibur, BD Bioscience) and Flow jo (Thermo Fisher Scientific). Each sample was analyzed by dot plots, and the CD45$^+$CD3$^+$CD4$^+$ cell population (FIG. 22A), the CD45$^+$CD3$^+$CD8$^+$ cell population (FIG. 22B) and the CD45$^+$CD3$^-$CD49b$^+$ cell population (FIG. 22C) were defined as CD4+ T cells, CD8$^+$ T cells and NK cells, respectively, and the proportions thereof relative to the total spleen cells were calculated and multiplied by the cell number counted with a hemocytometer, and the number of CD4$^+$ T cells, CD8$^+$ T cells and NK cells which increased after administration of mono-mIL-12-Fc was analyzed.

As a result, it could be seen that, in comparison with the control, mono-mIL-12-Fc increased the number of CD4+ T cells (FIG. 22A) and CD8$^+$ T cells (FIG. 22B) in the tumor-transplanted mice in a concentration-dependent manner. However, bi-mIL-12-Fc increased the number of CD8$^+$ T cells only in the group administered with the same at a concentration corresponding to an equivalent molar amount of 0.5 µg IL-12 (FIG. 22B), and it did not increase the number of CD4$^+$ T cells (FIG. 22A) and CD8$^+$ T cells (FIG. 22B) in the group administered with the same at a concentration corresponding to an equivalent molar amount of 1 µg IL-12. Consistent with the previous study results (Cerwenka and Lanier, 2016; Schreiber et al., 2011) that NK cells do not form memory cells in tumor-transplanted mice, it was observed that on 34 days after tumor transplantation, the number of NK cells in the groups administered with mono-mIL-12-Fc and bi-mIL-12-Fc was similar to that in the control group. As a result, it was shown that mono-mIL-12-Fc caused greater expansion of CD4+ T cells and CD8$^+$ T cells, accounting for the stronger tumor growth inhibition, compared to bi-mIL12-Fc.

Based on the report (Schreiber et al., 2011) that an increase in the number of adaptive immune dells (CD4+ T cells and CD8$^+$ T cells) that infiltrated tumors is important in inhibiting tumor growth, whether mono-mIL-12-Fc would increase the number of adaptive immune cells that infiltrated tumors was analyzed. When mono-mIL-12-Fc was administered 6 times, there were many mice having no tumor. For this reason, mono-mIL-12-Fc was administered 3 times, and then the number of immune cells that infiltrated the mouse tumor was analyzed.

FIGS. 22D-22F show the results of measuring the number of total immune cells (FIG. 22D), CD4$^+$ T cells (FIG. 22E), and CD8$^+$ T (FIG. 22F) cells that infiltrated the tumor in the mice sacrificed 3 days after the third administration in FIGS. 21A-21E.

Specifically, after treatment as shown in FIGS. 21A-21E, the mouse tumor was dissected 24 days after tumor transplantation and weighed. Then, the tumor was crushed using a wire mesh and collagenase (100 µg/ml) in a Petri dish and centrifuged in 10 ml of 2% FBS-containing medium at 50 g for 5 minutes to remove the parenchymal tissue. Next, 1 ml of red blood cell lysis buffer was added thereto to lyse red blood cells, and the resulting cells were washed with PBS to prepare a cell suspension, and the number of the cells was countered with a hemocytometer. APC, FITC, or PE-cy5-conjugated anti-CD45, anti-CD3, anti-CD4, and anti-CD8 antibodies were added to the cells isolated from tumor which were then stained at 4° C. for 30 minutes, washed with cold PBS (pH 7.4), and then analyzed by flow cytometry (FACS Calibur,BD Bioscience) and Flow jo (Thermo Fisher Scientific). Each sample was analyzed by dot plots, and then the CD45$^+$ cell population (FIG. 22D), the CD45$^+$CD3$^+$CD4$^+$ cell population (FIG. 22E) and the CD45$^+$CD3$^+$CD8$^+$ cell population (FIG. 22F) were defined as total tumor infiltrating immune cells, tumor infiltrating CD4$^+$ T cells and tumor infiltrating CD8$^+$ T cells, respectively. The proportions of these cells relative to the cells isolated from the whole tumor were calculated and multiplied by the cell number counted with a hemocytometer, and then the number of total tumor infiltrating immune cells, tumor infiltrating CD4$^+$ T cells and tumor infiltrating CD8$^+$ T cells that increased after administration of mono-mIL-12-Fc was analyzed.

As a result, it could be seen that, in comparison with the control, bi-mIL-12-Fc and mono-mIL-12-Fc concentration-dependently increased the number of total immune cells, $CD4^+$ T cells and $CD8^+$ T cells that infiltrated the tumor. At the equimolar concentration, mono-mIL-12-Fc significantly increased the total immune cells (FIG. 22D), $CD4^+$ T cells (FIG. 22E) and $CD8^+$ T cells (FIG. 22F) that infiltrated the tumor, compared to bi-mIL-12-Fc. As a result, it was shown that mono-mIL-12-Fc caused greater infiltration of CD4+ T cells (FIG. 22E) and $CD8^+$ T cells (FIG. 22F) in tumor, accounting for the stronger tumor growth inhibition, compared to bi-mIL12-Fc.

Example 17

Evaluation of the Effects of Mono-mIL-12-Fc on Cytokine Secretion from Immune Cells In Vivo and Increase in Cytotoxicity IL-12 is known to inhibit the growth of cancer cells by increasing the secretion of IFN-γ from T cells and NK cells (Trinchieri, 2003). In addition, IL-12 exhibits anticancer effects by enhancing the direct cytotoxic effects of cytotoxic T cells and natural killer cells against cancer cells. Thus, analysis was performed to determine whether the high anticancer effect of mono-IL-12-Fc would be attributable to an increase in the serum IFN-γ concentration of tumor-transplanted mice and to the enhancement of the direct cytotoxic effect of cytotoxic T cells and natural killer cells against cancer cells.

FIGS. 23A-23B show the results of an ELISA performed to measure the concentration of IFN-γ in the serum separated from the blood sampled from mouse facial veins at 24 hours after the last administration in FIGS. 21A-21E.

Specifically, at 24 hours after the last administration of the mIL-12-Fc fusion protein in FIGS. 20A-20B, blood was sampled from the facial veins of the mice. The blood was allowed to stand at room temperature for 2 hours so as to induce blood coagulation, and then centrifuged at 8000 rpm for 10 minutes, and the supernatant serum was collected. In order to measure the concentration of IFN-γ in the serum, a 96-well plate (Thermo Fisher Scientific) for ELISA was coated with mouse IFN-γ capture antibody for 12 hours, washed with PBST (PBS with 0.1% Tween-20), and then blocked with 1% BSA (PBS with 1% bovine serum albumin) at room temperature for 1 hour. After washing with PBST (PBS with 0.1% Tween-20), the serum was diluted 10-fold with 1% BSA, and incubated at room temperature for 2 hour. After washing with PBST (PBS with 0.1% Tween-20), each well was incubated with biotin-conjugated mouse IFN-γ detection antibody (Thermo Fisher Scientific) at room temperature for 1 hour. After washing with PBST (PBS with 0.1% Tween-20), each well was incubated with avidin-conjugated horseradish peroxidase (HRP) (Thermo Fisher Scientific) at room temperature for 30 minutes, washed with PBST (PBS with 0.1% Tween-20), and then treated with 3,3',5,5'-tetramethylbenzidine substrate (TMB, sigma-aldrich). The absorbance at 450 nm was measured using a microplate reader. As shown in FIG. 23B, the serum IFN-γ concentration of the mice administered with bi-mIL-12-Fc did not increase compared to that of the control group. However, it was observed that the serum IFN-γ levels were increased in the mice receiving the mono-mIL12-Fc treatment in proportion to the dose up to an equivalent molar amount of 1 mg rmIL12 compared to that of the control group (FIG. 23A). In addition, it was shown that the tumor formation inhibitory effect of mono-mIL-12-Fc was because mono-mIL-12-Fc increased the secretion of IFN-γ known to have the effect of inhibiting the proliferation of some cancer cells.

In the tumor-transplanted mice treated with bi-mIL12-Fc, serum levels of IFN-γ were low (FIG. 23B). Thus, in order to determine whether bi-mIL-12-Fc had a low ability to induce IFN-γ secretion from NK cells and T cells, the serum IFN-γ concentration was measured at indicated time points after single administration of mono-mIL-12-Fc and bi-mIL-12-Fc.

Figure 23C:
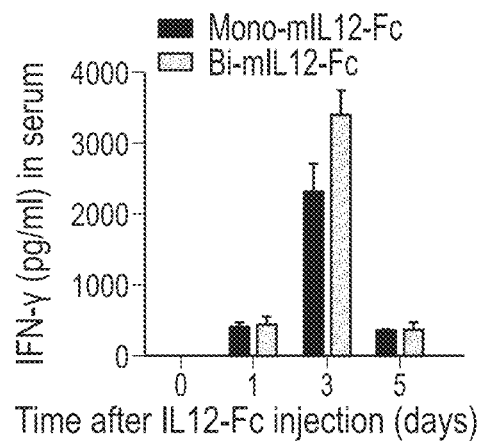
FIG. 23C is a graph showing the results of an ELISA performed to measure the concentration of IFN-γ in serum separated from blood collected from mouse facial veins on 1, 3 and 5 days after intraperitoneally administering bi-mIL-12-Fc and mono-mIL-12-Fc at a concentration equimolar to 1 μg rmIL-12 when the tumor volume in Balb/c mice transplanted with CT26$^{HER2/Neu}$ cancer cells reached 300 mm$^3$.

FIG. 23C shows the results of an ELISA performed to measure the concentration of IFN-γ in serum at various indicated time points after single intraperitoneal administration of bi-mIL-12-Fc and mono-mIL-12-Fc to Balb/c mice transplanted with $CT26^{HERS/Neu}$ colorectal cancer cells.

Specifically, when the tumor volume in the Balb/c mice transplanted with $CT26^{HERS/Neu}$ colorectal cancer cells reached 300 $mm^3$, bi-mIL-12-Fc and mono-mIL-12-Fc was administered intraperitoneally at a concentration equimolar to 1 μg rmIL-12. After 1, 3 and 5 days, blood was sampled from the facial veins of the mice. The blood was allowed to stand at room temperature for 2 hours so as to induce blood coagulation and centrifuged at 8000 rpm for 10 minutes, and the supernatant serum was collected. In order to measure the concentration of IFN-γ in the serum, a 96-well plate (Thermo Fisher Scientific) for ELISA was coated with mouse IFN-γ capture antibody for 12 hours, washed with PBST (PBS with 0.1% Tween-20), and then blocked with 1% BSA (PBS with 1% bovine serum albumin) at room temperature for 1 hour. After washing with PBST (PBS with 0.1% Tween-20), the serum was diluted 10-fold with 1% BSA, and incubated at room temperature for 2 hour. After washing with PBST (PBS with 0.1% Tween-20), each well was incubated with biotin-conjugated mouse IFN-γ detection antibody (Thermo Fisher Scientific) at room temperature for 1 hour. After washing with PBST (PBS with 0.1% Tween-20), each well was incubated with avidin-conjugated horseradish peroxidase (HRP) (Thermo Fisher Scientific) at room temperature for 30 minutes, washed with PBST (PBS with 0.1% Tween-20), and then treated with 3,3',5,5'-tetramethylbenzidine substrate (TMB, sigma-aldrich). The absorbance at 450 nm was measured using a microplate reader. As shown in FIG. 23C, in the tumor-transplanted mice, the group administered with bi-mIL-12-Fc showed a serum IFN-γ concentration similar to that of the mono-mIL-12-Fc group up to 5 days, suggesting that bi-mIL-12-Fc has no intrinsic defect in the ability to induce IFN-γ secretion from effector cells.

Figure 23D:
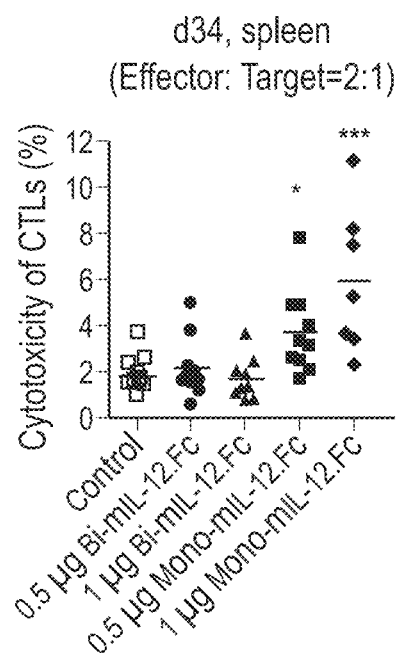
FIG. 23D is a graph showing the results of measuring the cytotoxic effect of cytotoxic T cells, isolated from the spleen of mice sacrificed 3 days after the last administration in FIGS. 21A-21E, against CT26$^{HERS/Neu}$ cancer cells.

FIG. 23D is a graph showing the results of measuring the cytotoxic effect of cytotoxic T cells, isolated from the spleen of mice sacrificed 3 days after the last administration in FIGS. 21A-21E, against $CT26^{HERS/Neu}$ cancer cells.

Specifically, 72 hours after the last administration of the cytokine in FIGS. 21A-21E, the mice were sacrificed, and the spleen was dissected therefrom and crushed in a 60 mm dish containing a 70-micron mesh and PBS. To the cells obtained by centrifugation, red blood cell lysis buffer was added to lyse red blood cells. Next, the cells were washed with PBS and incubated with APC-conjugated anti-CD3 antibody (Thermo Fisher Scientific) and PE-conjugated anti-CD8 antibody at 4° C. for 30 minutes. After the cells were washed with PBS, cytotoxic T cells ($CD3^+CD8^+$) were isolated using FACS Aria III (BD biosciences, Korea). To measure the cytotoxic effect of the cytotoxic T cells against target $CT26^{HER2/Neu}$ cancer cells, the $CT26^{HER2/Neu}$ cancer cells were stained with calcein AM (Thermo Fisher Scientific Inc., 10 μM). $CT26^{HER2/Neu}$ cancer cells ($2 \times 10^6$) were suspended in 2 ml of DPBS, and mixed with 2 μl of calcein AM (10 mM), and then incubated at 37° C. under 5% $CO_2$ for 45 minutes. After washing with 10 ml of 10% FBS-containing RPMI1640, the cells were added to each well of a 96-well plate at a density of $2\times10^4$ cells per well, and cytotoxic T cells ($1\times10^5$/100 μl/well) were added to each well and incubated at 37° C. under 5% $CO_2$ for 4 hours. Living $CT26^{HER2/Neu}$ cancer cells showing green fluorescence and dead $CT26^{HER2/Neu}$ cancer cells showing no green fluorescence were analyzed by flow cytometry, and the cytotoxic effect of the cytotoxic T cells was expressed as percentage. It was shown that the cytotoxic T cells isolated from the tumor-transplanted mice administered with mono-mIL-12-Fc showed a higher cytotoxic effect against target $CT26^{HER2/Neu}$ cancer cells compared to the cytotoxic T cells isolated from the tumor-transplanted mice administered with bi-mIL-12-Fc or the cytotoxic T cells isolated from the control group (FIG. 23D). In addition, it was shown that the tumor formation inhibitory effect of mono-mIL-12-Fc was attributed to the direct cytotoxic effect of some cytotoxic T cells against cancer cells.

FIGS. 23E-23G show the results of measuring the cytotoxic effect of cytotoxic T cells, isolated from the spleen of mice sacrificed 3 days after the third administration in FIGS. 21A-21E, using $CT26^{HER2/Neu}$ cancer cells expressing tumor antigen and 4T1 cells expressing no tumor antigen, in order to determine whether the cytotoxic effect of cytotoxic T cells that was enhanced by administration of mono-IL-12-Fc to the tumor-transplanted mice would be tumor antigen-specific.

Specifically, 72 hours after the third administration of mono-IL-12-Fc in FIGS. 20A-20B, the mice were sacrificed, and the spleen was dissected therefrom and crushed in a 60-mm dish containing a 70-micron mesh and PBS. In order to measure the cytotoxic effect of cytotoxic T cells against target $CT26^{HERS/Neu}$ cancer cells (FIG. 23E) and non-target 4T1 cells (FIG. 23F), the $CT26^{HERS/Neu}$ cancer cells and the 4T1 cancer cells were stained with calcein AM (Thermo Fisher Scientific Inc., 10 μM) according to the method used for FIGS. 21M-21N. After washing three times with 10 ml of 10% FBS-containing RPMI1640, the cells were added to each well of a 96-well plate at a density of $2\times10^4$ cells per well, and cytotoxic T cells ($1\times10^5$/100 μl/well) were added to each well and incubated in a 37° C. incubator under 5% $CO_2$ for 4 hours. Living $CT26^{HERS/Neu}$ cancer cells showing green fluorescence and dead $CT26^{HERS/Neu}$ cancer cells showing no green fluorescence or 4T1 cancer cells were analyzed by flow cytometry, and the cytotoxic effect of the cytotoxic T cells was expressed as percentage. As a result, it was shown that the cytotoxic effect of cytotoxic T cells that was enhanced by administration of mono-mIL-12-Fc was target cell-specific (FIG. 23G).

FIG. 23H shows the results of measuring the cytotoxic effect of natural killer cells, isolated from the spleen of mice sacrificed 3 days after the third administration in FIGS. 21A-21E, against $CT26^{HERS/Neu}$ cancer cells.

Specifically, 3 days after the third administration of the cytokine in FIGS. 21A-21E, the mice were sacrificed, and the spleen was dissected therefrom and crushed in a 70-mm dish containing a 70-micron mesh and PBS. To the cells obtained by centrifugation, red blood cell lysis buffer was added to lyse red blood cells. Next, the cells were washed with PBS and incubated with APC-conjugated anti-CD3 antibody (Thermo Fisher Scientific) and PE-conjugated anti-CD49b antibody at 4° C. for 30 minutes. After the cells were washed with PBS, natural killer cells ($CD3^-CD49b^+$) were isolated using FACS Aria III (BD biosciences, Korea). To measure the cytotoxic effect of the natural killer cells against target $CT26^{HER2/Neu}$ cancer cells, the $CT26^{HER2/Neu}$ cancer cells were stained with calcein AM (Thermo Fisher Scientific Inc., 10 μM). $CT26^{HER2/Neu}$ cancer cells ($2\times10^6$) were suspended in 2 ml of DPBS, and mixed with 2 μl of calcein AM (10 mM), and then incubated at 37° C. under 5% $CO_2$ for 45 minutes. After washing with 10 ml of 10% FBS-containing RPMI1640, the cells were added to each well of a 96-well plate at a density of $2\times10^4$ cells per well, and natural killer cells ($1\times10^5$/100 μl/well) were added to each well and incubated at 37° C. under 5% $CO_2$ for 4 hours. Living $CT26^{HERS/Neu}$ cancer cells showing green fluorescence and dead $CT26^{HERS/Neu}$ cancer cells showing no green fluorescence were analyzed by flow cytometry, and the cytotoxic effect of the natural killer cells was expressed as percentage. It was shown that the natural killer cells isolated from the tumor-transplanted mice administered with mono-mIL-12-Fc showed a higher cytotoxic effect against target $CT26^{HERS/Neu}$ cancer cells compared to the natural killer cells isolated from the tumor-transplanted mice administered with bi-mIL-12-Fc or the cytotoxic T cells isolated from the control group. In addition, it was shown that the tumor formation inhibitory effect of mono-mIL-12-Fc was attributed to the direct cytotoxic effect of some natural killer cells against cancer cells.

Example 18

Evaluation of the Ability of Mono-mIL-12-Fc to Form Effector $CD8^+$ T Cells and Memory $CD8^+$ T Cells In Vivo The production of adaptive immunity in tumor-transplanted mice is evaluated by whether effector memory $CD8^+$ T cells and memory $CD8^+$ T cells are generated. Whether the tumor removal effect of mono-mIL-12-Fc would be attributable to the generation of effector memory $CD8^+$ T cells and memory $CD8^+$ T cells was measured.

Figure 24A:
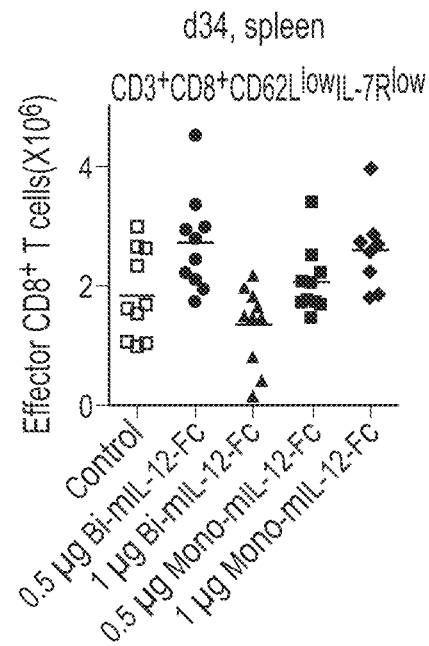
FIG. 24A is a graph showing the results of measuring the number of CD8$^+$ effector T cells isolated from in the spleen isolated from tumor-bearing mice sacrificed 3 days after the last administration in FIGS. 21A-21E.
Figure 24B:
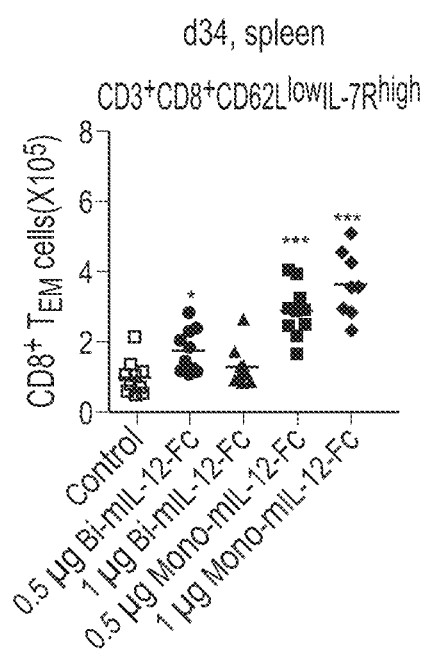
FIG. 24B is a graph showing the results of measuring the number of CD8$^+$ effector memory T cells in the spleen isolated from tumor-bearing mice sacrificed 3 days after the last administration in FIGS. 21A-21E.
Figure 24C:
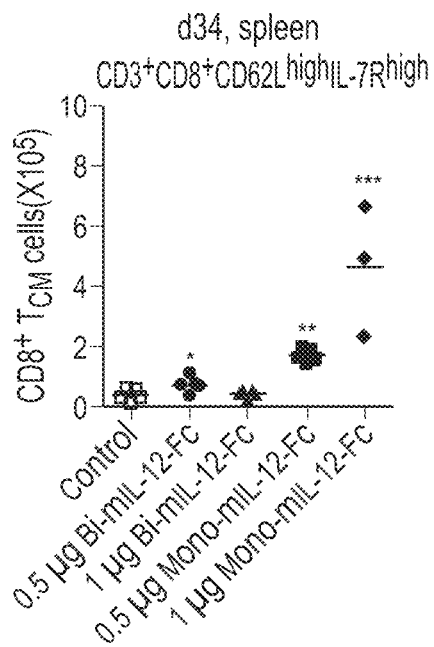
FIG. 24C is a graph showing the results of measuring the number of CD8$^+$ central memory T cells in the spleen isolated from tumor-bearing mice sacrificed 3 days after the last administration in FIGS. 21A-21E.

FIGS. 24A, 24B and 24C show the results of measuring the number of effector $CD8^+$ T cells (FIG. 24A), effector memory $CD8^+$ T cells (FIG. 24B) and memory $CD8^+$ T cells (FIG. 24C) produced when mono-mIL-12-Fc was administered to tumor-bearing mice.

Specifically, after treatment as shown in FIGS. 21A-21E, the mouse spleen was dissected 34 days after tumor transplantation, crushed using a wide mesh in a Petri dish, and then washed with 10 ml of 2% FBS-containing medium. Next, 1 ml of red blood cell lysis buffer was added thereto to lyse red blood cells, and the resulting cells were washed with PBS to prepare a spleen cell suspension, and the number of the cells was countered with a hemocytometer. APC, FITC, PE or PE-cy5-conjugated anti-CD3, anti-CD8, anti-CD62L, and anti-IL-7 receptor (IL-7R) antibodies were added to the spleen cells which were then stained at 4° C. for 30 minutes, washed with cold PBS (pH 7.4), and then analyzed by flow cytometry (FACS Calibur, BD Bioscience) and Flow jo (Thermo Fisher Scientific). Each sample was analyzed by dot plots, and the $CD3^+CD8^+CD62L^{hi}IL-7R^{hi}$ cell population, the $CD3^+CD8^+CD62L^{low}IL-7R^{hi}$ cell population and the $CD3^+CD8^+CD62L^{hi}IL-7R^{hi}$ cell population were defined as effector $CD8^+$ T cells, effector memory $CD8^+$ T cells and memory $CD8^+$ T cells, respectively, and the proportions thereof relative to the total spleen cells were calculated and multiplied by the cell number counted with a hemocytometer, and the number of effector $CD8^+$ T cells, effector memory CD8$^+$ T cells and memory CD8$^+$ T cells which increased after administration of mono-mIL-12-Fc was analyzed.

As a result, it could be seen that, in comparison with the control, mono-mIL-12-Fc concentration-dependently increased the number of effector memory CD8$^+$ T cells and memory CD8$^+$ T cells in tumor-transplanted mice. However, bi-mIL-12-Fc increased the number of effector memory CD8$^+$ T cells and memory CD8$^+$ T cells only in the group administered at a concentration corresponding to an equivalent molar amount of 0.5 μg IL-12, and did not increase the number of effector memory CD8$^+$ T cells and memory CD8$^+$ T cells in the group administered with the same at a concentration corresponding to an equivalent molar amount of 1 μg IL-12. Thus, it was found that the higher tumor formation inhibitory effect of mono-mIL-12-Fc was attributed to the increased number of effector memory CD8$^+$ T cells and memory CD8$^+$ T cells, compared to bi-mIL-12-Fc.

Figure 24D:
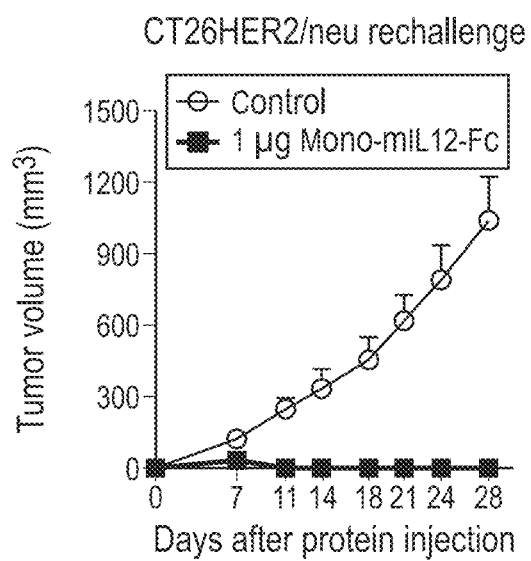
FIG. 24D shows the results obtained by re-transplanting CT26$^{HER2/Neu}$ cancer cells into survived Balb/c mice 120 days after administration of 1 μg mono-IL-12-Fc in FIGS. 21A-21E, and measuring tumor volume changes in the mice.

FIG. 24D shows the results obtained by re-transplanting CT26$^{HER2/Neu}$ cancer cells into the survived mice 120 days after administration of 1 μg mono-IL-12-Fc in FIGS. 21A-21E and measuring tumor volume changes in the mice.

Specifically, 120 days after the last administration of 1 μg mono-IL-12-Fc to the female Balb/c mice (NARA Biotech, Korea) in FIGS. 21A-21E, the survived mice were shaved, and CT26$^{HER2/Neu}$ cells (1×10$^6$ cells/mouse) diluted in 150 μL of PBS were transplanted subcutaneously into the mice. Next, the tumor was measured twice a week without additional administration of 1 μg mono-IL-12-Fc, and the tumor volume (V) was calculated using the following equation: V=length×width/2. As a result, it could be seen that, in comparison with the control group, the tumor in the mice that survived after administration of 1 μg mono-mIL-12-Fc started to decrease from 11 days. Thus, it was found that when mono-mIL-12-Fc was administered to the tumor-transplanted mice, it produced effector memory CD8$^+$ T cells and memory CD8$^+$ T cells, and thus even when a tumor was transplanted again into the mice, it would be removed.

Example 19

Evaluation of the Ability of Mono-mIL-12-Fc to Form Memory Precursor Effector CD8$^+$ T Cells In Vivo In Examples 16 and 18, it was observed that the effect of bi-mIL-12-Fc on increasing the number of CD8$^+$ T cells, effector memory CD8$^+$ T cells and central memory CD8$^+$ T cells in tumor-transplanted mice was lower than that of mono-mIL-12-Fc. It was reported that after the effector phase in which activated CD8$^+$ T cells directly destroy tumor cells, effector CD8$^+$ T cells partially differentiate into memory precursor effector cells (MPECs) and then into memory CD8$^+$ T cells, and mostly differentiate into short-lived effector cells (SLECs). Thus, analysis was performed to determine whether CD8$^+$ T cells activated by administration of bi-mIL-12-Fc would differentiate into short-lived effector cells, and thus the number of memory CD8$^+$ T cells produced was small so that they could not remove tumors.

Figure 24E:
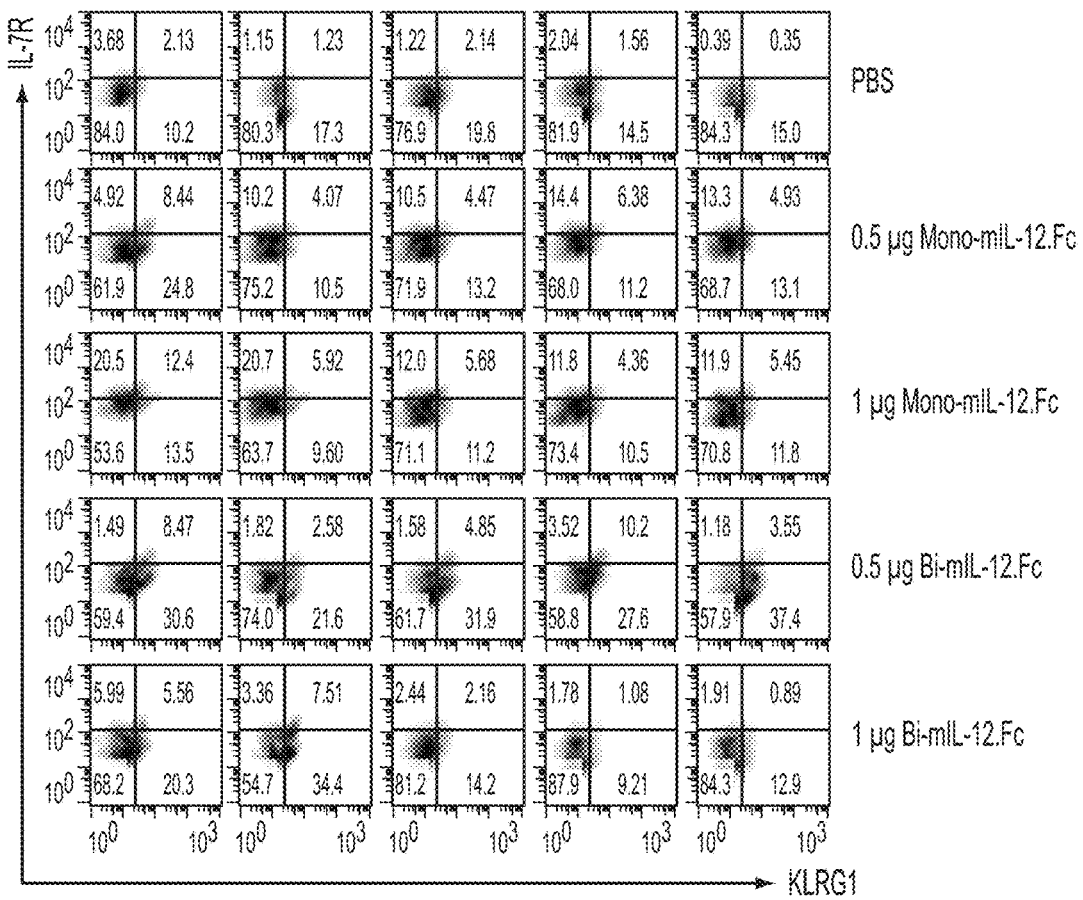
FIG. 24E are flow cytometry dot plots showing the proportion of memory precursor effector cells (KLRG1$^-$IL-7R$^+$) and short-lived effector cells (KLRG1$^+$IL-7R$^+$) among CD8$^+$ T cells in the spleen isolated from tumor-bearing mice sacrificed 3 days after the third administration in FIGS. 21A-21E.
Figure 24F:
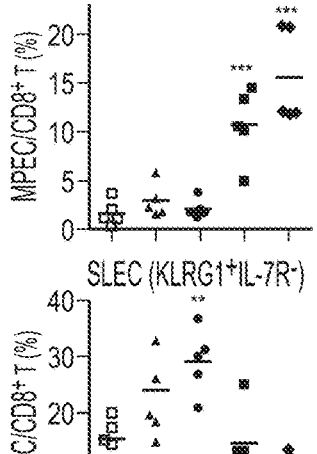
FIGS. 24F-24G are graphs showing the results of flow cytometry performed to analyze the proportion of memory precursor effector cells (KLRG1$^+$IL-7R$^-$) (FIG. 24F) and short-lived effector cells (KLRG1$^+$IL-7R$^-$) (FIG. 24G) among CD8$^+$ T cells in the spleen isolated from tumor-bearing mice sacrificed 3 days after the third administration in FIGS. 21A-21E.
Figure 24G:
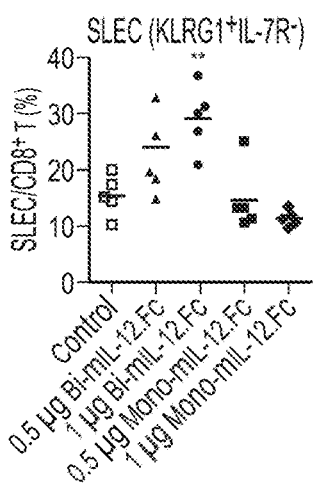

FIGS. 24E-24G show the results of analyzing the proportions of memory precursor effector cells (KLRG1$^-$IL-7R$^+$) and short-lived effector cells (KLRG1$^+$IL-7R$^-$) in the CD8$^+$ T cells present in the spleen of mice sacrificed 3 days after the third administration in FIGS. 21A-21E. FIG. 24E are flow cytometry dot plots showing the proportion of memory precursor effector cells (KLRG1$^-$IL-7R$^+$) and short-lived effector cells (KLRG1$^+$IL-7R$^-$) among CD8$^+$ T cells in the spleen isolated from tumor-bearing mice sacrificed 3 days after the third administration in FIGS. 21A-21E. FIGS. 24F-24G are graphs showing the results of flow cytometry performed to analyze the proportion of memory precursor effector cells (KLRG1$^-$IL-7R$^+$) (FIG. 24F) and short-lived effector cells (KLRG1$^+$IL-7R$^-$) (FIG. 24G) among CD8$^+$ T cells in the spleen isolated from tumor-bearing mice sacrificed 3 days after the third administration in FIGS. 21A-21E.

Specifically, after treatment as shown in FIGS. 21A-21E, the mouse spleen was dissected 24 days after tumor transplantation, crushed using a wide mesh in a Petri dish, and then washed with 10 ml of 2% FBS-containing medium. Next, 1 ml of red blood cell lysis buffer was added thereto to lyse red blood cells, and the resulting cells were washed with PBS to prepare a cell suspension. APC, FITC, PE or PE-cy5-conjugated anti-CD3, anti-CD8, anti-KLRG1, and anti-IL-7 receptor (IL-7R) antibodies were added to the spleen cells which were then stained at 4° C. for 30 minutes, washed with cold PBS (pH 7.4), and then analyzed by flow cytometry (FACS Calibur, BD Bioscience) and Flow jo (Thermo Fisher Scientific). Each sample was analyzed by dot plots, and the CD3$^+$CD8$^+$KLRG1$^-$IL-7R$^+$ cell population and the CD3$^+$CD8$^+$KLRG1$^+$IL-7R$^-$ cell population were defined as memory precursor effector cells and short-lived effector cells, respectively, and the proportions thereof relative to the total spleen cells were analyzed.

As a result, it could be seen that, in comparison with the control, mono-mIL-12-Fc concentration-dependently increased the proportion of memory precursor effector cells in the tumor-transplanted mice. However, administration of bi-mIL-12-Fc did not increase the proportion of memory precursor effector cells compared to control, but rather increase the number of short-lived effector cells. Thus, it was found that mono-mIL-12-Fc significantly increased the number of effector memory CD8$^+$ T cells and memory CD8$^+$ T cells, compared to bi-mIL-12-Fc by promoting production of memory precursor effector cells, indicating that it has a higher effect on tumor removal.

Example 20

Evaluation of the Effect of mono-mIL-12-Fc on Expression of Transcription Factors Involved in Induction of Memory Cell Differentiation It was reported that when CD8$^+$ T cells were administered with high concentrations of IL-12 or were activated by administering IL-12 frequently for 2 days or more, expression of the transcription factor T-bet that allows CD8$^+$ T cells to differentiate into short-lived effector cells increases and expression of the transcription factor eomesodermin (Eomes) that allows CD8$^+$ T cells to differentiate into memory precursor effector cells decreases. Thus, analysis was performed to determine whether mono-mIL-12-Fc and bi-mIL-12-Fc would differentially regulate the expression of T-bet and Eomes in CD8$^+$ T cells so as to change the proportion of CD8$^+$ T cells that differentiate into short-lived effector cells.

Figure 25A:
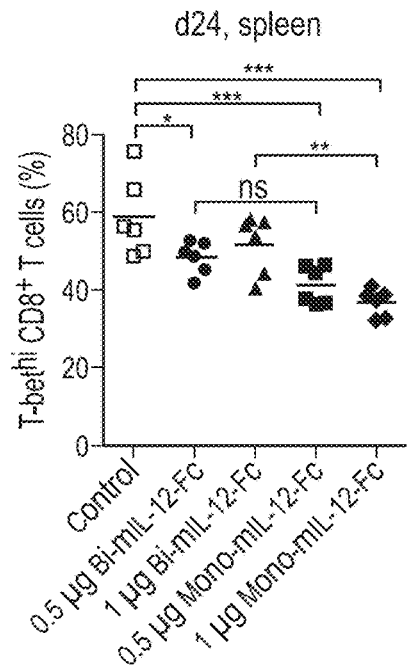
FIG. 25A is a graph showing the results of flow cytometry analysis performed to measure the proportion of CD8$^+$ T cells (which showed high expression of the transcription factor T-bet that inhibits memory cell differentiation) in spleen cells isolated from mice sacrificed 3 days after the third administration in FIGS. 21A-21E.
Figure 25B:
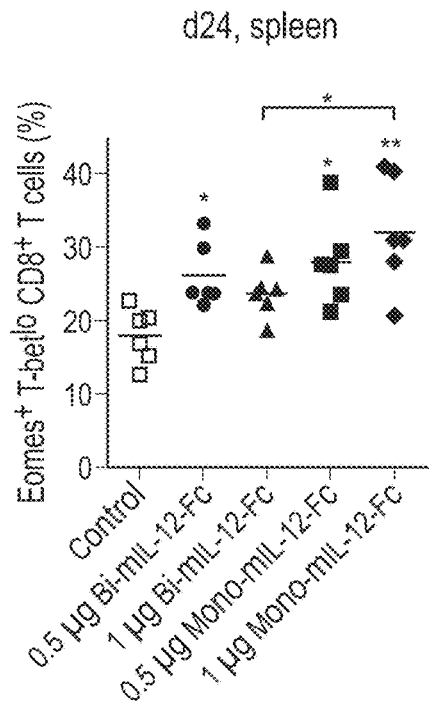
FIG. 25B is a graph showing the results of flow cytometry analysis performed to measure the proportion of CD8$^+$ T cells (which showed high expression of Eomes and low expression of T-bet) in spleen cells isolated from mice sacrificed 3 days after the third administration in FIGS. 21A-21E.

FIGS. 25A and 25B show the results of flow cytometry analysis performed to measure the proportions of CD8$^+$ T cells (which show high expression of T-bet (FIG. 25A) that inhibits memory cell differentiation) and CD8$^+$ T cells (which show low expression of Eomes (FIG. 25B) that promotes memory cell differentiation) in the spleen of mice sacrificed 3 days after the third administration in FIGS. 21A-21E.

Specifically, after treatment as shown in FIGS. 21A-21E, the mouse spleen was dissected 24 days after tumor transplantation, crushed using a wire mesh in a Petri dish, and then washed with 10 ml of 2% FBS-containing medium. Next, 1 ml of red blood cell lysis buffer was added thereto to lyse red blood cells, and the resulting cells were washed with PBS to prepare a cell suspension. The spleen cells were stained with PE-cy5- or FITC-conjugated anti-CD3 and anti-CD8 antibodies at 4° C. for 30 minutes and washed with cold PBS (pH 7.4). Then, the cells were fixed with Foxp3/ Transcription Factor Staining Buffer Set (Thermo Fisher Scientific) (which is an intranuclear transcription factor staining reagent), and permeabilized. Next, the cells were stained with PE- or efluor 660-conjugated anti-T-bet or anti-Eomes antibody at 4° C. for 30 minutes, and then analyzed by flow cytometry (FACS Calibur, BD Bioscience) in permeabilization buffer and Flow jo (Thermo Fisher Scientific) for flow cytometry data analysis. Each sample was analyzed by dot plots, and the proportions of the $CD3^+CD8^+T$-$bet^{high}$ cell population (FIG. 25A) and the $CD3^+CD8^+Eomes+T$-$bet^{low}$ cell population (FIG. 25B) were analyzed. As a result, it could be seen that, in comparison with the control, mono-mIL-12-Fc concentration-dependently reduced the proportion of the $CD3^+CD8^+T$-$bet^{high}$ cell population and increased the proportion of the $CD3^+CD8^+$ Eomes+T-$bet^{low}$ cell population. However, bi-mIL-12-Fc reduced the proportion of the $CD3^+CD8^+T$-$bet^{high}$ cell population only in the group administered with the same at a concentration corresponding to an equivalent molar amount of 0.5 μg IL-12 and increased the proportion of the $CD3^+$ $CD8^+Eomes^+T$-$bet^{low}$ cell population in the group. In addition, in the group administered with bi-mIL-12-Fc at a concentration corresponding to an equivalent molar amount of 1 μg IL-12, bi-mIL-12-Fc did not show the effect of reducing the proportion of the $CD3^+CD8^+T$-$bet^{high}$ cell population or increasing the proportion of the $CD3^+CD8^+$ $Eomes^+T$-$bet^{low}$ cell population. Thus, it was found that, in comparison with bi-mIL-12-Fc, mono-mIL-12-Fc had a higher effect of removing tumors by reducing the proportion of the $CD3^+CD8^+T$-$bet^{high}$ cell population and increasing the proportion of the $CD3^+CD8^+Eomes^+T$-$bet^{low}$ cell population so as to significantly increase the number of effector memory $CD8^+$ T cells and memory $CD8^+$ T cells.

It is known that when $CD8^+$ T cells are stimulated with inflammatory cytokines such as IL-12 in the presence of a T cell receptor signal and a co-stimulatory signal, the phosphorylation of STAT4 increases and the phosphorylated STAT4 (pSTAT4) migrates into the nucleus and binds to the T-bet enhancer, thereby increasing the expression of T-bet. Thus, analysis was performed to determine whether the differentiation of $CD8^+$ T cells into short-lived effector cells, which occurred when bi-mIL-12-Fc was administered at a concentration corresponding to an equivalent molar amount of 1 μg IL-12, would be because administration of bi-mIL-12-Fc at a concentration corresponding to an equivalent molar amount of 1 μg IL-12 increased the expression of pSTAT4 and T-bet when T cells were activated in the tumor draining lymph nodes of the tumor-transplanted mice, compared to mono-mIL-12-Fc.

Figure 25C:
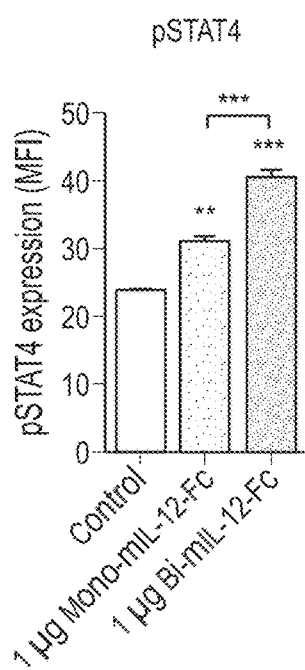
FIG. 25C is a graph showing the results of flow cytometry analysis performed to measure the expression level of phosphorylated STAT4 in CD8$^+$ T cells isolated from tumor draining (inguinal) lymph nodes at 24 hours after intraperitoneally administering bi-mIL-12-Fc and mono-mIL-12-Fc once at a concentration equimolar to 1 μg rmIL-12 when the tumor volume in Balb/c mice transplanted with CT26$^{HER2/Neu}$ cancer cells reached 300 mm$^3$.

FIG. 25C shows the results of flow cytometry analysis performed to measure the expression level of phosphorylated STAT4 in $CD8^+$ T cells isolated from the tumor draining lymph node on 24 hours after intraperitoneally administrating bi-mIL-12-Fc and mono-mIL-12-Fc once at a concentration corresponding to equivalent molar amount of 1 μg rmIL-12 when the tumor volume in the Balb/c mice transplanted with $CT26^{HERS/Neu}$ reached 300 mm³.

Specifically, as described with respect to FIG. 23C, when the tumor volume in the Balb/c mice transplanted with $CT26^{HERS/Neu}$ colorectal cancer cells reached 300 mm³, bi-mIL-12-Fc and mono-mIL-12-Fc were administered intraperitoneally into the mice at a concentration equimolar to 1 μg rmIL-12. After 24 hours, the tumor draining lymph node of the mice was dissected, crushed using a wire mesh in a Petri dish, and then washed with 10 ml of 2% FBS-containing medium. Next, 1 ml of red blood cell lysis buffer was added thereto to lyse red blood cells, and the resulting cells were washed with PBS, thus preparing a cell suspension. The draining lymph node cells were stained with PE-cy5- or FITC-conjugated anti-CD3 and anti-CD8 antibodies at 4° C. for 30 minutes, washed with PBS (pH 7.4), and then fixed in cold methanol. Next, the draining lymph node cells were washed with cold PBS (pH 7.4), stained with APC-conjugated anti-pSTAT4 antibody at 4° C. for 30 minutes, washed with cold PBS (pH 7.4), and then analyzed by flow cytometry (FACS Calibur, BD Bioscience) and Flow jo (Thermo Fisher Scientific). Each sample was analyzed by dot plots, and the expression levels of pSTAT4 in $CD3^+CD8^+T$ cells were compared. As a result, in comparison with mono-mIL-12-Fc, bi-mIL-12-Fc showed the effect of increasing the expression of pSTAT4 when $CD8^+T$ cells were activated in the tumor draining lymph nodes of the tumor-transplanted mice.

Figure 25D:
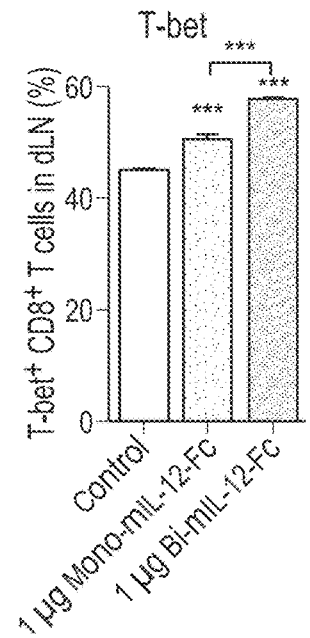
FIG. 25D is a graph showing the results of flow cytometry analysis performed to measure the proportion of CD8$^+$ T cells (which expressed T-bet that inhibits memory cell differentiation) in tumor draining (inguinal) lymph nodes at 72 hours after the single intraperitoneal administration in FIG. 25C.
Figure 25E:
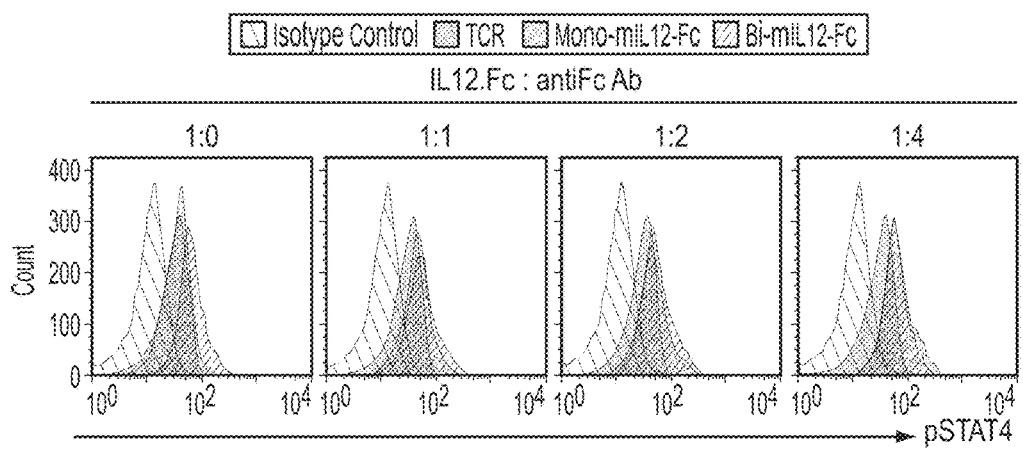
FIG. 25E are histograms from flow cytometry analysis performed to measure the expression level of pSTAT4 when CD8$^+$ T cells isolated from the spleen and inguinal lymph node of normal Balb/c mice were stimulated with the mono-mIL-12-Fc and bi-mIL-12-Fc that cross-reacted with anti-Fc antibody.
Figure 25F:
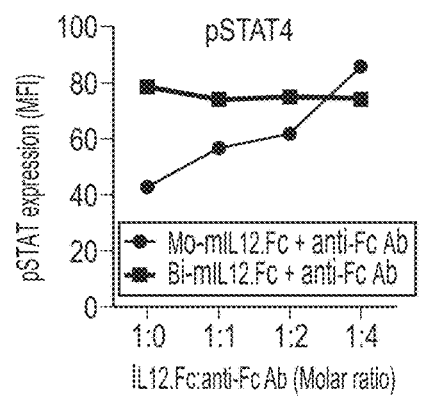
FIG. 25F is a graph showing the results of flow cytometry analysis performed to measure the expression level of pSTAT4 when CD8$^+$ T cells isolated from the spleen and inguinal lymph node of normal Balb/c mice were stimulated with the mono-mIL-12-Fc and bi-mIL-12-Fc that cross-reacted with anti-Fc antibody.
Figure 25G:
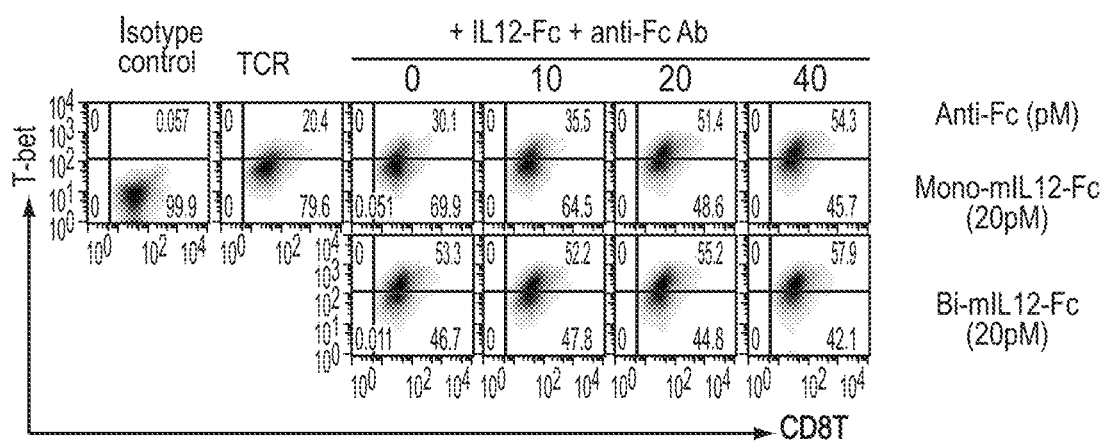
FIG. 25G are flow cytometry dot plots showing the proportion of T-bet-expressing CD8$^+$ T cells when CD8$^+$ T cells isolated from the spleen and groin lymph node of normal Balb/c mice were stimulated with the mono-mIL-12-Fc and bi-mIL-12-Fc that cross-reacted with anti-Fc antibody.
Figure 25H:
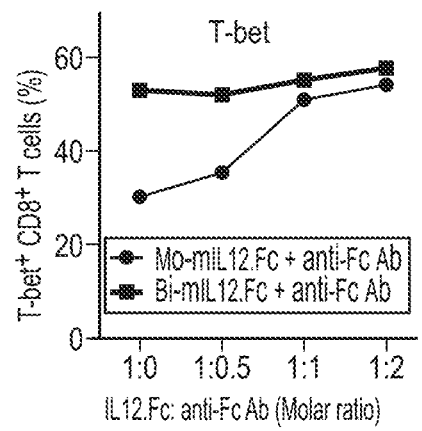
FIG. 25H is a graph showing the results of flow cytometry analysis performed to measure the proportion of T-bet-expressing CD8$^+$ T cells when CD8$^+$ T cells isolated from the spleen and groin lymph node of normal Balb/c mice were stimulated with the mono-mIL-12-Fc and bi-mIL-12-Fc that cross-reacted with anti-Fc antibody.

FIG. 25D shows the results of flow cytometry performed to measure the proportion of $CD8^+$ T cells (which express T-bet that inhibits memory cell differentiation) in the tumor draining lymph node on 72 hours after single intraperitoneal administration in FIG. 25C.

Specifically, as described with respect to FIG. 23C, when the tumor volume in the Balb/c mice transplanted with $CT26^{HERS/Neu}$ colorectal cancer cells reached 300 mm³, bi-mIL-12-Fc and mono-mIL-12-Fc were administered intraperitoneally into the mice at a concentration corresponding to equivalent molar amount of 1 μg rmIL-12. After 72 hours, the tumor draining lymph node of the mice was dissected, crushed using a wire mesh in a Petri dish, and then washed with 10 ml of 2% FBS-containing medium. Next, 1 ml of red blood cell lysis buffer was added thereto to lyse red blood cells, and the resulting cells were washed with PBS, thus preparing a cell suspension. The draining lymph node cells were stained with PE-cy5- or FITC-conjugated anti-CD3 and anti-CD8 antibodies at 4° C. for 30 minutes, washed with PBS (pH 7.4), fixed using Foxp3/Transcription Factor Staining Buffer Set (Thermo Fisher Scientific) (which is an intranuclear transcription factor staining reagent), and then permeabilized. Next, the cells were stained with PE- or APC-conjugated anti-T-bet antibody at 4° C. for 30 minutes, and then analyzed by flow cytometry (FACS Calibur (BD Bioscience) in permeabilization buffer and Flow jo (Thermo Fisher Scientific) analysis. Each sample was analyzed by dot plots, and the proportion of $CD3^+CD8^+$ T cells expressing T-bet was compared. As a result, in comparison with mono-mIL-12-Fc, bi-mIL-12-Fc showed the effect of increasing the expression of T-bet when $CD8^+T$ cells were activated in the draining lymph lodes of the tumor-transplanted mice. Thus, it was found that the differentiation of $CD8^+$ T cells into short-lived effector cells, which occurred when bi-mIL-12-Fc was administered at a concentration corresponding to equivalent molar amount 1 μg IL-12, was because administration of bi-mIL-12-Fc increased the expression of pSTAT4 and T-bet, compared to mono-mIL-12-Fc, when T cells in the tumor draining lymph nodes of the tumor-transplanted mice were activated.

FIGS. 25E-25H show the result of measuring whether when mono-mIL-12-Fc was cross-reacted with anti-Fc antibody, like bi-mIL-12-Fc expressing two L-12 molecules, so that CD8$^+$ T cells could be stimulated by two L-12 molecules, the expression of pSTAT4 and T-bet in the cells would be increased to a level similar to the level shown when the cells were treated with bi-mIL-12-Fc.

Specifically, spleens and tumor draining lymph nodes were dissected from normal Balb/c mice, crushed using a wire mesh in a Petri dish, and then washed with 10 ml of 2% FBS-containing medium. Next, 1 ml of red blood cell lysis buffer was added thereto to lyse red blood cells, and the resulting cells were washed with PBS, thus preparing a cell suspension. The lymph node cells were stained with PE-conjugated anti-CD8 antibody at 4° C. for 30 minutes, washed with cold PBS (pH 7.4), and incubated with anti-PE microbeads (Miltenyi Biotec) for 15 minutes, and CD8$^+$ T cells were separated therefrom using a MACS separator and an LS column (Miltenyi Biotec). 100 ∝l of 0.5 µg/ml of anti-CD3 antibody was added to each well of a 96-well round bottom plate which was then incubated at 4° C. for 12 hours and washed with PBS to remove anti-CD3 antibody not attached to the plate, and 50 µl of 2 µg/ml of anti-CD28 antibody was added to each well. Next, mono-mIL-12-Fc and bi-mIL-12-Fc were reacted with various concentrations of anti-Fc antibody at 4° C. for 30 minutes, and then added to each well at a concentration equimolar to 20 pM IL-12. Next, CD8$^+$ T cells (4×10$^4$/well) were added to each well and incubated in a 37° C. incubator for 3 hours in order to measure the expression of pSTAT4 and for 3 days in order to measure the expression of T-bet. To measure the expression of pSTAT4 and T-bet, the cells were stained according to the method described with respect to FIGS. 25C and 25D, and were then analyzed by flow cytometry. Each sample was analyzed by dot plots, and the expression levels of pSTAT4 (FIG. 25E and FIG. 25F) or T-bet in the CD8$^+$ T cells (FIG. 25G and FIG. 25H) were compared. As a result, it was shown that when mono-mIL-12-Fc was cross-reacted with anti-Fc antibody so that CD8$^+$ T cells could be stimulated by two IL-12 molecules, the expression levels of pSTAT4 and T-bet in the cells increased to the levels shown when the cells were treated with bi-mIL-12-Fc.

Figure 26:
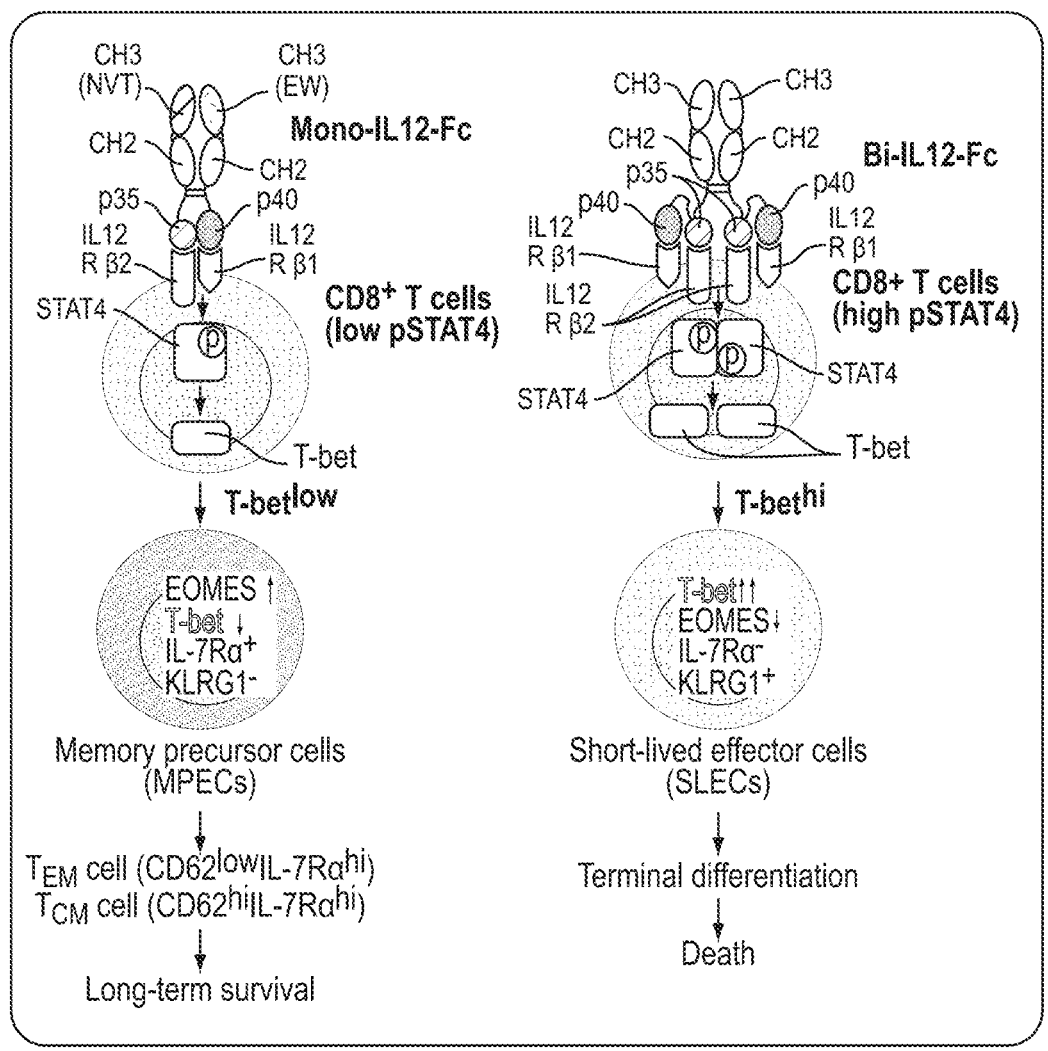
FIG. 26 is an overall schematic view showing a mechanism that induces differentiation of memory precursor effector cells by mono-mIL-12-Fe and a mechanism that induces differentiation of short-lived effector cells by bi-mIL-12-Fe.

In conclusion, as shown in FIG. 26, in comparison with bi-mIL-12-Fc, mono-mIL-12-Fc induces low expression of pSTAT4 and T-bet in CD8$^+$ T cells so that the CD8$^+$ T cells can differentiate into memory precursor effector cells and then into effector memory cells and central memory cells. Thus, mono-mIL-12-Fc can remove tumors from tumor-transplanted mice even at low concentration (corresponding to equivalent molar amount 0.5 µg IL-12), thus prolonging the life-span of the mice. However, bi-mIL-12-Fc induces high expression of pSTAT4 and T-bet in CD8$^+$ T cells so that the cells can differentiate into short-livered effector cells precluding the development of memory cells. Thus, when bi-mIL-12-Fc is administered at the same molar concentration as that of mono-mIL-12-Fc, it cannot completely remove tumors from tumor-transplanted mice. Thus, only when bi-mIL-12-Fc is administered at higher concentration (corresponding to equivalent molar amount of 2 µg IL-12) and cytotoxic CD8$^+$ T cells are expanded in the effector phase that directly destroys tumor cells, bi-mIL-12-Fc can remove tumors.

INDUSTRIAL APPLICABILITY

The heterodimeric Fc-fused protein according to the present invention has an advantage in that it can retain the activity of a naturally occurring physiologically active protein, which is composed of two or more different subunit proteins and thereby exhibit the physiological activity by forming an assembled protein, because each subunit of the protein can be separately fused to each chain of heterodimeric Fc of immunoglobulin such that the fused protein can maintain the naturally occurring form and structure to the highest possible degree. In addition, the in vivo half-life of the physiologically active protein contained in the heterodimeric Fc-fused protein can be significantly increased due to the heterodimeric Fc-mediated long half-life such that the physiological activities thereof in vivo can be long-lasting.

Further, the heterodimeric Fc-fused protein according to the present invention has an advantage in that it is possible to easily produce a heterodimeric Fc-fused protein in the native configuration without need to optimize an additional purification process.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of producing a heterodimeric Fc-fused protein, the method comprising:
   (a) introducing one or more than one polynucleotide encoding a heterodimeric Fc-fused protein comprising a first Fc region and a second Fc region of an immunoglobulin Fc (fragment crystallizable) pair and the p40 and p35 subunits of IL-12 into a cell,
   wherein the p40 and p35 subunits of IL-12 are linked separately to the first Fc region and the second Fc region, or to the second Fc region and the first Fc region, respectively,
   wherein the p40 and p35 subunits are each linked to the N-terminus or C-terminus of the Fc regions, and
   wherein CH3 domains of the first Fc region and the second Fc region each comprise one or more mutations selected from the group consisting of:
   (i) glutamic acid (E), arginine (R), methionine (M), aspartic acid (D), or histidine (H) substitution of the amino acid residue at position 370 in the CH3 domain of the first Fc region;
   (ii) glutamic acid (E) substitution of the amino acid residue at position 360 in the CH3 domain of the first Fc region;
   (iii) tryptophan (W) substitution of the amino acid residue at position 409 in the CH3 domain of the first Fc region;
   (iv) asparagine (N), aspartic acid (D), alanine (A), isoleucine (I), glycine (G), or methionine (M) substitution of the amino acid residue at position 357 in the CH3 domain of the second Fc region, and threonine (T) or tryptophan (W) substitution of the amino acid residue at position 364 in the CH3 domain of the second Fc region; and
   (v) threonine (T) substitution of the amino acid residue at position 405 in the CH3 domain of the second Fc region, and valine (V) substitution of the amino acid residue at position 399 in the CH3 domain of the second Fc region,
   and wherein mutation positions are numbered according to the EU index, and
   (b) culturing the cell for a sufficient period of time to express the heterodimeric Fc-fused protein.

2. The method according to claim 1, wherein the p40 and p35 subunits are each linked to the N-terminus of the Fc regions.

3. The method according to claim 1, wherein the p40 or p35 subunit is linked to its corresponding Fc region by a linker.

4. The method according to claim 2, wherein the p35 subunit is linked to its corresponding Fc region by a linker.

5. The method according to claim 3, wherein the linker comprises a $(G_4S)_3$ linker.

6. The method according to claim 1, wherein each of the first Fc region and the second Fc region is from an Fc region selected from the group consisting of human IgG1, IgG2, IgG3, and IgG4.

7. The method according to claim 1, wherein the first Fc region and the second Fc region are comprised in a whole antibody form selected from the group consisting of human IgG1, IgG2, IgG3, and IgG4.

8. The method according to claim 1, wherein the CH3 domain of the second Fc region further comprises: arginine (R) substitution of the amino acid residue at position 347, wherein the positions are numbered according to the EU index.

9. The method according to claim 8, wherein the CH3 domains in the first Fc region and the second Fc region further comprise the following residues:
   (a) cysteine (C) substitution at position 349 in the CH3 domain of the first Fc region; and
   (b) cysteine (C) substitution at position 354 in the CH3 domain of the second Fc region, wherein the positions are numbered according to the EU index.

10. The method according to claim 9, wherein the IL-12 is human IL-12.

11. A cell comprising one or more than one polynucleotide encoding a heterodimeric Fc-fused protein comprising a first Fc region and a second Fc region of an immunoglobulin Fc (fragment crystallizable) pair and the p40 and p35 subunits of IL-12,
    wherein the p40 and p35 subunits of IL-12 are linked separately to the first Fc region and the second Fc region, or to the second Fc region and the first Fc region, respectively,
    wherein the p40 and p35 subunits are each linked to the N-terminus or C-terminus of the Fc regions, and
    wherein CH3 domains of the first Fc region and the second Fc region each comprise one or more mutations selected from the group consisting of:
    (a) glutamic acid (E), arginine (R), methionine (M), aspartic acid (D), or histidine (H) substitution of the amino acid residue at position 370 in the CH3 domain of the first Fc region;
    (b) glutamic acid (E) substitution of the amino acid residue at position 360 in the CH3 domain of the first Fc region;
    (c) tryptophan (W) substitution of the amino acid residue at position 409 in the CH3 domain of the first Fc region;
    (d) asparagine (N), aspartic acid (D), alanine (A), isoleucine (I), glycine (G), or methionine (M) substitution of the amino acid residue at position 357 in the CH3 domain of the second Fc region, and threonine (T) or tryptophan (W) substitution of the amino acid residue at position 364 in the CH3 domain of the second Fc region; and
    (e) threonine (T) substitution of the amino acid residue at position 405 in the CH3 domain of the second Fc region, and valine (V) substitution of the amino acid residue at position 399 in the CH3 domain of the second Fc region,
    wherein mutation positions are numbered according to the EU index.

12. The cell according to claim 11, wherein the p40 and p35 subunits are each linked to the N-terminus of the Fc regions.

13. The cell according to claim 12, wherein the p40 or p35 subunit is linked to its corresponding Fc region by a linker.

14. The cell according to claim 13, wherein the p35 subunit is linked to its corresponding Fc region by a linker.

15. The cell according to claim 14, wherein the linker comprises a $(G_4S)_3$ linker.

16. The cell according to claim 11, wherein each of the first Fc region and the second Fc region is from an Fc region selected from the group consisting of human IgG1, IgG2, IgG3, and IgG4.

17. The cell according to claim 11, wherein the first Fc region and the second Fc region are comprised in a whole antibody form selected from the group consisting of human IgG1, IgG2, IgG3, and IgG4.

18. The cell according to claim 11, wherein the CH3 domain of the second Fc region further comprises: arginine (R) substitution of the amino acid residue at position 347, wherein the positions are numbered according to the EU index.

19. The cell according to claim 18, wherein the CH3 domains in the first Fc region and the second Fc region further comprise the following residues:
   (i) cysteine (C) substitution at position 349 in the CH3 domain of the first Fc region; and
   (ii) cysteine (C) substitution at position 354 in the CH3 domain of the second Fc region, wherein the positions are numbered according to the EU index.

20. The cell according to claim 19, wherein the IL-12 is human IL-12.

* * * * *